United States Patent [19]
Kaplan et al.

[11] Patent Number: 5,813,993
[45] Date of Patent: Sep. 29, 1998

[54] ALERTNESS AND DROWSINESS DETECTION AND TRACKING SYSTEM

[75] Inventors: Richard Frederic Kaplan, Richmond Heights; Kenneth Alan Loparo, Chesterland, both of Ohio

[73] Assignee: Consolidated Research of Richmond, Inc., Richmond Heights, Ohio

[21] Appl. No.: 628,474

[22] Filed: Apr. 5, 1996

[51] Int. Cl.$^6$ .................................................... A61B 5/04
[52] U.S. Cl. ......................... 600/544; 600/26; 600/545; 600/300
[58] Field of Search ................................. 128/731, 732, 128/630; 600/26, 544, 545, 300

[56] References Cited

U.S. PATENT DOCUMENTS

| | | | |
|---|---|---|---|
| 3,953,831 | 4/1976 | Estrada | 340/53 |
| 4,272,764 | 6/1981 | Herr et al. | 340/575 |
| 4,502,122 | 2/1985 | Yanaghishima et al. | 364/424 |
| 4,564,833 | 1/1986 | Seko et al. | 340/576 |
| 4,602,247 | 7/1986 | Seko et al. | 340/575 |
| 4,604,611 | 8/1986 | Seko et al. | 340/576 |
| 4,617,559 | 10/1986 | Slansky | 340/576 |
| 4,862,359 | 8/1989 | Trivedi et al. | 128/731 |
| 4,875,020 | 10/1989 | Chiu | 340/575 |
| 4,928,090 | 5/1990 | Yoshimi et al. | 340/575 |
| 5,311,876 | 5/1994 | Olsen et al. | 128/731 |
| 5,311,877 | 5/1994 | Kishi | 128/732 |
| 5,447,166 | 9/1995 | Gevins | 128/731 |

OTHER PUBLICATIONS

Carskadon, M. A., and Rechtschaffen, A., "Chapter 73: Monitoring and Staging Human Sleep," Principles and Practice of Sleep Medicine, Section 7 Methodology (W.B. Saunders, Philadelphia, PA), pp. 665–683, 1987.

Clenney, S. L., and Johnson, S. M., "Back to Basics: A Handbook of EEG Technology," Beckman Instruments, Inc., 1983.

Gaillard, J. M., "EEG Fitting: A New Method for Numerical Analysis of EEG," Neuropsychobiology, vol. 17, pp. 9–14, 1987.

(List continued on next page.)

*Primary Examiner*—John P. Lacyk
*Assistant Examiner*—Stephen Huang
*Attorney, Agent, or Firm*—Laff, Whitesel, Conte & Saret, Ltd.

[57] ABSTRACT

A drowsiness detection system constructed according to the invention provides improved performance by preserving and analyzing newly discovered information contained in rhythmic signal components above 30 Hz which the prior art has universally ignored or discarded as "noise." In the first and second embodiments of the invention, one or more analog EEG signals are collected from a subject, appropriately filtered, converted into digital form, and subjected to frequency analysis. Selected signal components from the frequencies above 30 Hz (such as the frequency range 80–420 Hz), which have a high correlation with subject drowsiness, are isolated, and their amplitude, energy, or power contribution to the EEG signal is used to produce a continuous output measure reflecting the subject's alertness or drowsiness. The output measure may be compared with a threshold to provide an indication of whether the subject is excessively drowsy. In a third embodiment, the analog EEG signal is supplied to a plurality of analog signal processing channels corresponding to respective predefined frequency ranges. Selected signal components in frequencies above 30 Hz are isolated (in a manner analogous to that of the first and second embodiments), and their amplitude, energy, or power contribution to the EEG signal is used to produce a continuous output measure reflecting the subject's alertness or drowsiness.

67 Claims, 22 Drawing Sheets

OTHER PUBLICATIONS

Galambos, R., and Makeig, S., "Physiological Studies of Central Masking in Man. I: The Effects of Noise on the 40–Hz Steady–State Response," Journal of the Acoustical Society of America, vol. 92, No. 5, pp. 2683–2690, Nov. 1992.

Galambos, R., and Makeig, S., "Physiological Studies of Central Masking in Man. II: Tonepip SSRs and the Masking Level Difference," Journal of the Acoustical Society of America, vol. 92, No. 5, pp. 2691–2697, Nov. 1992.

Johnson, L., Lubin, A., Naitoh, P., Nute, C., and Austin, M., "Spectral Analysis of the EEG of Dominant and Non–Dominant Alpha Subjects During Walking and Sleeping," Electroencephalography and clinical Neurophysiology (Elsevier Scientific Publishing Co., Amsterdam), vol. 26, pp. 361–370, 1969.

Jokeit, H., and Makeig, S., "Differing Event–Related Patterns of Gamma Band Power in Brain Waves of Fast and Slow Reacting Subjects," Proceedings of the National Academy of Sciences, USA, vol. 91, pp. 6339–6343 (available from Navy Web Site http://128.49.52.9/~scott/jokeit94.html), 1994.

Kramer, A. F., "Physiological Metrics of Mental Workload: A Review of Recent Progress," Navy Personnel Research and Development Center Report NPRDC–TN–90–23, Jun. 1990.

Lesser, R. P., Webber, W. R. S., and Fisher, R. S., "Design Principles for Computerized EEG Monitoring," Electroencephalography and clinical Neurophysiology (Elsevier Scientific Publishing Co., Ireland) vol. 82, pp. 239–247, 1992.

Loring, D. W., and Sheer, D. E., "Laterality of 40 Hz EEG and EMG During Cognitive Performance," Psychophysiology, vol. 21, No. 1, pp. 34–37, Jan. 1984.

Makeig, S., and Inlow, M., "Lapses in Alertness: Coherence of Fluctuations in Performance and EEG Spectrum," Electroencephalography and clinical Neurophysiology (Elsivier Scientific Publishers Ireland), vol. 86, pp. 23–35, 1993.

Makeig, S., and Jung, T., "Changes in Alertness Are a Principal Component of Variance in the EEG Spectrum," (available from Navy Web Site http://128.49.52.9/~scott/pca95.html), Oct. 1995.

Makeig, S., and Jung, T., "Tonic, Phasic, and Transient EEG Correlates of Auditory Awareness in Drowsiness," (available from Navy Web Site http://128.49.52.9/~scott/cbr95.html), Sep. 1995.

Makeig, S., "Auditory Event–Related Dynamics of the EEG Spectrum and Efects of Exposure to Tones," Electroencephalography and Clinical Neurophysiology, vol. 86, pp. 283–293, (available from Navy Web Site http://128.49.52.9/~scott/~ersp93.html), 1993.

Myslobodsky, M. S., Coppola, R., Bar–Ziv, J., and Weinberger, D. R., "Adequacy of the International 10–20 Electrode System for Computed Neurophysiologic Topography," Journal of Clinical Neurophysiology (Raven Press, Ltd., New York), vol. 7, No. 4, pp. 507–518, 1990.

O'Hanlon, J. F., and Beatty, J., "Concurrence of Electroencephalographic and Performance Changes During a Simulated Radar Watch and Some Implications for the Arousal Theory of Vigilance," in Vigilance (R. R. Mackie, ed., Plenum Press, New York), pp. 189–201, 1977.

Pritchard, W. S., and Duke, D. W., "Measuring Chaos in the Brain: A Tutorial Review of Nonlinear Dynamical EEG Analysis," International Journal of Neuroscience, vol. 67, pp. 31–80, 1992.

Pritchard, W. S., and Duke, D. W., "Measuring 'Chaos' in the Brain: A Tutorial Review of EEG Dimension Estimation," Brain and Cognition, vol. 27, pp. 353–397, 1995.

Taheri, B. A., Knight, R. T., and Smith, R. L., "A Dry Electrode for EEG Recording," Electroencephalography and clinical Neurophysiology (Elsevier Science Ireland Ltd.), vol. 90, pp. 376–383, 1994.

Åkerstedt, T., Hume, K., Minors, D., and Waterhouse, J., "Regulation of Sleep and Naps on an Irregular Schedule," Sleep, vol. 16, No. 8, pp. 736–743, 1993.

Åkerstedt, T., Kecklund, G., and Knutsson, A., "Manifest Sleepiness and the Spectral Content of the EEG during Shift Work," Sleep, vol. 14, No. 3, pp. 221–225, 1991.

Åkerstedt, T., and Gillberg, M., "Subjective and Objective Sleepiness in the Active Individual," International Journal of Neuroscience, vol. 52, pp. 29–37, 1990.

Åkerstedt, T., and Kecklund, G., "Stability of Day and Night Sleep—A Two–Year Follow–Up of EEG Parameters in Three–Shift Workers," Sleep, vol. 14, No. 6, pp. 507–510, 1991.

Allen, R. W., Parseghian, Z., Kelly, S. and Rosenthal, T.J., "An Experimental Study of Driver Alertness Monitoring," Systems Technology, Inc., Paper No. 508 (Prepared for National Highway Traffic Safety Administration, Office of Crash Avoidance Research), Sep. 1994.

Apple, H. P., and Burgess, R. C., "An Analysis of the Use of Active Electrodes in Electroencephalogram Ambulatory Monitoring," Postgraduate Medical Journal, vol. 52 (Suppl. 7), pp. 79–85, 1976.

Beatty, J., Greenberg, A., Deibler, W. P., and O'Hanlon, J. F., "Operant Control of Occipital Theta Rhythm Affects Performance in a Radar Monitoring Task," Science, vol. 183, Mar. 1, 1974, pp. 871–873.

Belyavin, A., and Wright, N. A., "Changes in Electrical Activity of the Brain with Vigilance," Electroencephalography and clinical Neurophysiology, vol. 66, pp. 137–144, 1987.

Bender, R., Schultz, B., Schultz A., and Pichlmayr, I., "Identification of EEG Patterns Occuring in Anesthesia by Means of Autoregressive Parameters," Biomedizinische Technik, vol. 36, pp. 236–240, Oct. 1991.

Binnie, C. D., Dekker, E., Smit, A., and Van Der Linden, G., "Practical Considerations in the Positioning of EEG Electrodes," Electroencephalography and Clinical Neurophysiology, vol. 53, pp. 453–458, 1982.

Bonnet, M. H., and Moore, S. E., "The Threshold of Sleep: Perception of Sleep as a Function of Time Asleep and Auditory Threshold," Sleep, vol. 5, No. 3, pp. 267–276, 1982.

Burgess, R. C. (ed.), "Technology and Equipment Review: Portable Sleep Screening Systems," Journal of Clinical Neurophysiology (Raven Press Ltd., New York), vol. 9, No. 1, pp. 154–159, 1992.

Carskadon, M.A., Dement, W. C., "Cumulative Effects of Sleep Restriction on Daytime Sleepiness,"Psychophysiology, vol. 18, No. 2, pp. 107–113, Mar. 1981.

Collura, T.F., Jacobs, E. C., Burgess, R. C., and Turnbull, J. P., "The Epilog System. Automated Long–Term EEG Monitoring for Epilepsy," IEEE Computer, Sep. 1992, pp. 5–14.

Corsi–Cabrera, M., et al., "Chaos in the Walking EEG as a Consequence of Sleep and Sleep Deprivation" Sleep, vol. 15, No. 6, pp. 550–555, 1992.

Daniel, R. S., "Alpha and Theta EEG in Vigilance," Perceptual and Motor Skills (Southern Universities Press), vol. 25, pp. 697–703, 1967.

Dasheiff, R., and Major–Vincent, D. (course directors), "Continuous Waveform Analysis," Frontier Science in EEG Symposium, University of Pittsburgh Medical Center, Oct. 9, 1993, Symposium Handout Book.

Declerck, A. C., Martens, W. L. J., and Schiltz, A. M., "Evaluation of Ambulatory EEG Cassette Recording," EEG Monitoring (Stefan, H., and Burr, W., eds., Gustav Fisher, New York), pp. 29–35, 1982.

Dinges, D. F., Orne, M. T., Orne, E. C., and Evans, F. J., "Voluntary Self–Control of Sleep to Facilitate Quasi–Continuous Performance" Final Summary Report, U.S. Army Medical Research and Development Command Report No. 80, NTIS No. AD–A102264, (Contributors to the Pennsylvania Hospital and U.S. Army Medical Research and Development Command), Mar. 31, 1980.

Dingus, T. A., Hardee, H. L., and Wierwille, W. W., "Development of Models for On–Board Detection of Driver Impairment," Accident Analysis & Prevention, vol. 19, No. 4, pp. 271–283, 1987.

Fagerström, K. O., and Lisper, H. O., "Effects of Listening to Car Radio, Experience, and Personality of the Driver on Subsidiary Reaction Time and Heart Rate in a Long–term Driving Task," in Vigilance (R. R. Mackie, ed., Plenum Press, New York), pp. 73–85, 1977.

Findley, L. J., Levinson M. P., and Bonnie, R. J., "Driving Performance and Automobile Accidents in Patients with Sleep Apnea," Clinics in Chest Medicine, vol. 13, No. 3, pp. 427–435, Sep. 1992.

Fruhstorfer, H., Langanke, P., Meinzer, K., Peter, J. H., and Pfaff, U., "Neurophysiological Vigilance Indicators and Operational Analysis of a Train Vigilance Monitoring Device: A Laboratory and Field Study," in Vigilance (R. R. Mackie, ed., Plenum Press, New York), pp. 147–162, 1977.

Fruhstorfer, H., Partanen, J., and Lumio, J., "Vertex Sharp Waves and Heart Action During The Onset of Sleep," Electroencephalography and Clinical Neurophysiology, vol. 31, pp. 614–617, 1971.

Gale, Anthony, "Some EEG Correlates of Sustained Attention," in Vigilance (R. R. Mackie, ed., Plenum Press, New York), pp. 263–283, 1977.

Gander, P. H., De Nguyen, B. E., Rosekind, M. R., and Connell, L. J., "Age, Circadian Rhythms, and Sleep Loss in Flight Crews," Aviation, Space and Environmental Medicine, vol. 64, No. 3, Sec. 1, pp. 189–195, Mar. 1993.

Gander, P. H., Graeber, R. C., Connell, L. J., and Gregory, K. B., "Crew Factors in Flight Operations: VIII. Factors Influencing Sleep Timing and Subjective Sleep Quality in Commercial Long–Haul Flight Crews," NASA Technical Memorandum 103852, Dec. 1991.

Gander, P. H., Graeber, R. C., Foushee, H. C., Lauber, J. K., and Connell, L. J., "Crew Factors in Flight Operations II: Psychophysiological Responses to Short–Haul Air Transport Operations" NASA Technical Memorandum 108856, Nov. 1994.

Garneski, T. M., and Steelman, H. F., "Equalizing Ear Reference Resistance in Monopolar Recording to Eliminate Artifactual Temporal Lobe Asymmetry," Electroencephalography and Clinical Neurophysiology, vol. 10, pp. 736–738, 1958.

Gillberg, M. Kecklund, G., and Åkerstedt, T., "Relations Between Performance and Subjective Ratings of Sleepiness During a Night Awake," Sleep, vol. 17, No. 3, pp. 236–241, 1994.

Gillberg, M., and Åkerstedt, T., "The Dynamics of the First Sleep Cycle," Sleep, vol. 14, No. 2, pp. 147–154, 1991.

Goldstein, R., Bauer, L. O., and Stern, J. A., "Effect of Task Difficulty and Interstimulus Interval on Blink Parameters," International Journal of Psychophysiology, vol. 13, pp. 111–117, 1992.

Gregg, K. M., Varvel, J. R., and Shafer, S. L., "Application of Semilinear Canonical Correlation to the Measurement of Opioid Drug Effect" Journal of Pharmacokinetics and Biopharmaceutics, vol. 20, No. 6, pp. 611–635, 1992.

Gusev, E. I., Pokrovskii, A. V., Volynskii, Y. D., Pyshkina, L. I., Erokhin, O. Y., Goloma, V. V., Gekht, A. B., Levtova, V. B., and Mal'tsev, P. V., "Compression Spectral Analysis of the EEG in Patients with Occlusive [sic: Occulsive] Lesions of the Carotid and Vertebral Arteries," Zhurnal Nevropatologii i Psikhiatrii imeni S. S. Korsakova, vol. 87, No. 8, pp. 1121–1126 (English translation (1989) available.), Aug. 1987.

Hartman, B. O., and Cantrell, G. K., "Sustained Pilot Performance Requires More Than Skill," Aerospace Medicine, Aug. 1967, pp. 800–803, Aug. 1967.

Hauri, P., and Orr, W. C., "The Sleep Disorders" (published by The Upjohn Company), pp. 6–8, 15, 17, and 53, 1982.

Hinrichs, H., and Machleidt, W., "Basic Emotions Reflected in EEG–Coherences," International Journal of Psychophysiology, vol. 13, pp. 225–232, 1992.

Hinrichs, H., "EEG Data Compression with Source Coding Techniques," Journal of Biomedical Engineering, vol. 13, Sep. 1991, pp. 417–423.

Hori, T., "Spatiotemporal Changes of EEG Activity During Waking–Sleeping Transition Period," International Journal of Neuroscience, vol. 27, pp. 101–114, 1985.

Horne, J. A., Donlon, J., and Arendt, J., "Green Light Attenuates Melatonin Output and Sleepiness during Sleep Deprivation," Sleep, vol. 14, No. 3, pp. 233–240, 1991.

Horváth, M., Frantík, E., Kopřiva, K., and Meissner, J., "EEG Theta Activity Increase Coinciding with Performance Decrement in a Monotonous Task," Activitas Nervosa Sup. (Praha), Mar. 18, 1976, pp. 207–210.

Humphrey, D., Sirevaag, E., Kramer, A. F., and Mecklinger, A., "Real–time Measurement of Mental Workload Using Psychophysiological Measures," Navy Personnel Research and Development Center Report NPRDC–TN–90–18, Apr. 1990.

Johnson, L. C., Slye, E. S., and Dement, W., "Electroencephalographic and Autonomic Activity During and After Prolonged Sleep Deprivation," Psychosomatic Medicine, vol. 27, No. 5, pp. 415–423, 1965.

Johnson, L. C., "Are Stages of Sleep Related to Waking Behavior?", American Scientist, vol. 61, May–Jun. 1973, pp. 326–338, May 1973.

Johnson, L. C., "Psychological and Physiological Changes Following Total Sleep Deprivation," in Sleep, Physiology and Pathology (Kales, A. ed., J. B. Lippincott Co., Philadelphia, PA), Ch. 16: Selective and Total Sleep Deprivation, pp. 206–220, 1969.

Keefe, F. B., Johnson, L. C., and Hunter, E. J., "EEG and Autonomic Response Pattern During Waking and Sleep Stages," Psychophysiology, vol. 8, No. 2, pp. 198–212, Mar. 1971.

Knipling, R. R., and Wang, J. S., "Crashes and Fatalities Related to Driver Drowsiness/Fatigue," Research Note, U.S. Department of Transportation, National Highway Traffic Safety Administration, Office of Crash Avoidance Research, Nov. 1994.

Knipling, R. R., and Wierwille, W. W., "U.S. IVHS Research: Vehicle–Based Drowsy Driver Detection," presented at Vigilance and Transport Conference, Lyon, France, Dec. 9–10, 1983.

Knipling, R. R., "IVHS Technologies Applied to Collision Avoidance: Perspectives on Six Target Crash Types and Countermeasures," presented at 1993 Annual IVHS America Annual Meeting, Safety & Human Factors Session, Apr. 14–17, 1993.

Kollar, E. J., Namerow, N., Pasnau, R. O., and Naitoh, P., "Neurological Findings During Prolonged Sleep Deprivation," Neurology, vol. 18, pp. 836–840, Sep. 1968.

Kryger, M. H., "Management of Obstructive Sleep Apnea," Clinics in Chest Medicine, vol. 13, No. 3, pp. 481–492, Sep. 1992.

Langlois, P. H., Smolensky, M. H., Hsi, B. P., and Weir, F. W., "Temporal Patterns of Reported Single–Vehicle Car and Truck Accidents in Texas, U.S.A. During 1980–1983," Chronobiology International, vol. 2, No. 2, pp. 131–140, 1985.

Lavie, P., Wollman, M., and Pollack, I., Abstract: "Frequency of Sleep Related Traffic Accidents and Hour of the Day," Authors' affiliation: Sleep Laboratory, Faculty of Medicine, Technion –Israel Institute of Technology), unknown.

Lawton, W. M., "Multidimensional Chirp Algorithms for Computing Fourier Transforms," Aware, Inc., Report No. AD900616, 1990.

Lille, F., and Chéliout, F., "Variations in Diurnal and Nocturnal Waking State in Air Traffic Controllers," European Journal of Applied Physiology, vol. 49, pp. 319–328, 1982.

Lubin, A., "Performance under Sleep Loss and Fatigue," in Sleep and Altered States of Consciousness (Ch. XXII), (Kety, S. S., Evarts, E. V., and Williams, H. L., eds.), Proceedings of the Association for Research in Nervous and Mental Disease (New York, Apr. 3–4, 1965), vol. XLV (The Williams and Wilkins Company, Baltimore), pp. 506–513, 1967.

Mackie, R. R. (ed.), "Vigilance. Theory, Operational Performance, and Physiological Correlates," NATO Scientific Affairs Division (Plenum Press, New York and London), 1977.

Mackie, R. R., and Wylie, C. D., "Countermeasures to Loss of Alertness in Motor Vehicle Drivers: A Taxonomy and Evaluation," Proceedings of the Human Factors Society 35th Annual Meeting, pp. 1149–1153, 1991.

Mallat, S. G., "A Theory for Multiresolution Signal Decomposition: The Wavelet Representation," IEEE Transactions on Pattern Analysis and Machine Intelligence, vol. 11, No. 7, pp. 674–693, Jul. 1989.

Malmo, R. B., and Surwillo, W. W., "Sleep Deprivation: Changes in Performance and Physiological Indicants of Activation," Psychological Monographs: General and Applied, vol. 74, No. 15, pp. 1–24, 1960.

Martikainen, K., Hasan, J., Urponen, H., Vuori, I., and Partinen, M., "Daytime Sleepiness: A Risk Factor in Community Life," Acta Neurol. Scand. (Finland), vol. 86, pp. 337–341, 1992.

Mathew, R., and Dutt, D. N., "Waveshaping Filters for Spectral Estimation of Short Segments of EEG Signals," Electronic Letters, vol. 29, No. 17, pp. 1534–1536, Aug. 19, 1993.

Matousek, M., and Petersén, I., "A Method for Assessing Alertness Fluctuations from EEG Spectra," Electroencephalography and clinical Neurophysiology (Elsevier Scientific Publishers Ireland), vol. 55, pp. 108–113, 1983.

McFarland, D. J., Neat, G. W., Read, R. F., and Wolpaw, J. R., "An EEG–Based Method for Graded Cursor Control," Psychobiology, vol. 21, No. 1, pp. 77–81, 1993.

Merica, H., and Gaillard, J., "The EEG of the Sleep Onset Period in Insomnia: A Discriminant Analysis," Physiology & Behavior, vol. 52, pp. 199–204, 1992.

Mirsky, A. F., and Pragay, E. B., "The Relation of EEG and Performance in Altered States of Consciousness," Sleep and Altered States of Consciousness (Chapter XXIII) (Williams and Wilkins, Baltimore, MD), pp. 514–534, 1967.

Mitler, M. M., Carskadon, M. A., Czeisler, C. A., Dement, W. C., Dinges, D. F., and Graeber, R. C., "Catastrophes, Sleep, and Public Policy: Consensus Report," Sleep (Raven Press, New York), vol. 11, No. 1, pp. 100–109, 1988.

Moldofsky, H., "Evaluation of Daytime Sleepiness," Clinics in Chest Medicine, vol. 13, No. 3, pp. 417–425, Sep. 1992.

Morrell, F., and Morrell, L., Abstract: "Spatial Distribution of Averaged Evoked Potentials in Man," abstracted in Society Proceedings, Electroencephalography and clinical Neurophysiology, vol. 18, pp. 522–523, 1965.

Murdoch, B. D., "The EEG in Pilot Selection," Aviation, Space and Environmental Medicine, vol. 62, pp. 1096–1098, Nov. 1991.

Murray, E. J., "Sleep, Dreams, and Arousal," (Appleton–Century–Crofts, New York), pp. 185–233, 337, 1965.

Naitoh, Paul, "Sleep Loss and Its Effects on Performance," Navy Medical Neuropsychiatric Research Unit (San Diego, CA), Report No. 68–3, Aug. 1969.

Nakasato, N., Kado, H., Nakanishi, M., Koyanagi, M., Kasai, N., Niizuma, H., and Yoshimoto, T., "Magnetic detection of sleep spindles in normal subjects," Electroencephalography and clinical Neurophysiology, vol. 76, pp. 123–130, 1990.

National Commission on Sleep Disorders Research, "Wake Up America: A National Sleep Alert; vol. 1: Executive Summary and Executive Report," Report of the National Commission on Sleep Disorders Research, U.S. Department of Health and Human Services (Washington DC, Supt. of Docs., U.S. Govt. Printing Office), Sep. 1992.

Niestroj, E., Spieweg, I., and Herrmann, W. M., "On the Dimensionality of Sleep–EEG Data," Neuropsychobiology, vol. 31, pp. 166–172, 1995.

Nunez, P. L., Reid, L., and Bickford, R. G., "The Relationship of Head Size to Alpha Frequency with Implications to a Brain Wave Model," Electroencephalography and Clinical Neurophysuology, vol. 44, pp. 344–352, 1978.

O'Hanlon, J.F., and Kelley, G.R., "Comparison of Performance and Physiological Changes Between Drivers Who Perform Well and Poorly During Prolonged Vehicular Operation," in Vigilance (R. R. Mackie, ed., Plenum Press, New York), pp. 87–109, 1977.

O'Hanlon, J.F., and Kelley, G.R., "A Psychophysiological Evaluation of Devices for Preventing Lane Drift and Run–Off–Road Accidents," Human Factors Research, Incorporated (Santa Barbara Research Park, 6780 Cortona Drive, Goleta, California 93017), Technical Report No. 1736–F, (prepared for Traffic Branch, Division of Highways, California Department of Transportation and United States Federal Highway Administration), Sep. 1974.

Ogilvie, R. D., Wilkinson, R. T., and Allison, S., "Detection of Sleep Onset: Behavioral, Physiological, and Subjective Convergence," Sleep, vol. 12, No. 5, pp. 458–474, 1989.

Ogilvie, R. D., and Wilkinson, R. T., "The Detection of Sleep Onset: Behavioral and Physiological Convergence," Psychophysiology, vol. 21, No. 5, pp. 510–520, Sep. 1984.

Olmstead, E., Hauri, P., Percy, L., Hellekson, C., Absract: "Subjective Versus Objective Estimation of Sleep Onset in Normal Sleepers and in Insomniacs," (Authors's affiliation: Dartmouth Medical School, Hanover, NH), abstracted in Sleep Research, vol. 9, 1980, p. 216.

Orr, W. C., and Hoffman, H. J., "A 90–Min Cardiac Biorhythm: Methodology and Data Analysis Using Modified Periodograms and Complex Demodulation," IEEE Transactions on Biomedical Engineering, vol. BME–21, No. 2, pp. 130–143, Mar. 1974.

Pijn, J. P., Van Neerven J., Noest, A., and Lopes da Silva, F. H., "Chaos or Noise in EEG Signals; Dependence on State and Brain Site," Electroencephalography and clinical Neurophysiology (Elsevier Scientific Publishers Ireland), vol. 79, pp. 371–381, 1991.

Röschke, J., and Aldenhoff, J. B., "A Nonlinear Approach to Brain Function: Deterministic Chaos and Sleep EEG," Sleep, vol. 15, No. 2, pp. 95–101, 1992.

Reingold, L., "Fighting off Fatigue," Air Transport World, Mar. 1995, pp. 80–82.

Resnikoff, H. L., and Burrus, C. S., "Interpretations of the Wavelet Transform," Aware, Inc., Report No. AD901105 (note: also to appear in proceedings of the Twenty–Fourth Asilomar Conference on Signals, Systems & Computers), 1990.

Resnikoff, H. L., "A Guide to Wavelets and their Application," Aware, Inc., Report No. AD920908, 1992.

Resnikoff, H. L., "Wavelets and Adaptive Signal Processing," Optical Engineering (ISSN 0091–3286), Jun. 1992.

Riemersma, J. B. J., Sanders, A. F., Wildervanck, C., and Gaillard, A. W., "Performance Decrement During Prolonged Night Driving" in Vigilance (R. R. Mackie, ed., Plenum Press, New York), pp. 41–58, 1977.

Rioul, O., and Vetterli, M., "Wavelets and Signal Processing," IEEE Signal Processing Magazine, Oct. 1991, pp. 14–38.

Roehrs, T., Beare, D., Zorick, F., and Roth, T., "Sleepiness and Ethanol Effects on Simulated Driving," Alcoholism: Clinical and Experimental Research, vol. 18, No. 1, pp. 154–158, Jan. 1994.

Rosekind, M. R., Gander, P. H., Connell, L. J., and Co, E. L., "Crew Factors in Flight Operations X: Alertness Management in Flight Operations," NASA Technical Memorandum No. DOT/FAA/RD–93/18, 1994.

Rosekind, M. R., Gander, P. H., Miller, D. L., Gregory, K. B., Smith, R. M., Weldon, K. J., Co, E. L., McNally, K. L., and Lebacqz, J. V., "Fatigue in Operational Settings: Examples from the Aviation Environment," Human Factors, vol. 36, No. 2, pp. 327–338, 1994.

Rosekind, M. R., Gander, P. H., and Dinges, D. F., "Alertness Management in Flight Operations: Strategic Napping," Aerospace Technology Conference and Exhibition, Sep. 23–26, 1991, Long Beach, CA (SAE International, Warrendale, PA), SAE Technical Paper Series 912138, pp. 1–12.

Rosekind, M. R., Graeber, R. C., Dinges, D. F., Connell, L. J., Rountree, M. S., Spinweber, C. L., Gillen, K. A., "Crew Factors in Flight Operations IX: Effects of Planned Cockpit Rest on Crew Performance and Alertness in Long–Haul Operations," NASA Technical Memorandum 108839, FAA Report DOT/FAA/92/24, Sep. 1994.

Santamaria, J., and Chiappa, K. H., "The EGG of Drowsiness in Normal Adults," Journal of Clinical Neurophysiology, vol. 4, No. 4, pp. 327–382, 1987.

Schiff, S. J., Aldroubi, A., Unser, M., and Sato, S., "Fast wavelet transformation of EEG," Electroencephalography and clinical Neurophysiology, vol. 91, pp. 442–455, 1994.

Sewitch, D. E., "NREM Sleep Continuity and the Sense of Having Slept in Normal Sleepers," Sleep (Raven Press, New York), vol. 7, No. 2, pp. 147–154, 1984.

Spencer, E. M., Green, J. L., and Willatts, S. M., "Continuous Monitoring of Depth of Sedation by EEG Spectral Analysis in Patients Requiring Mechanical Ventilation," British Journal of Anaesthesia, vol. 73, pp. 649–654 1994.

Standards of Practice Committee of the American Sleep Disorders Association, "Portable Recording in the Assessment of Obstructive Sleep Apnea," Unpublished position paper of American Sleep Disorders Association (Rochester, MN), unknown.

Stanford Sleep Disorders Clinic and Research Center, "Why Should We Care About Sleep? The Toll of Daytime Sleepiness and Sleep Disorders on Society," 1991.

Stoohs, R., and Guilleminault, C., "MESAM 4: An Ambulatory Device for the Detection of Patients at Risk for Obstructive Sleep Apnea Syndrome (OSAS)," Chest, vol. 101, No. 5, pp. 1221–1227m May 1992.

Strang, G., "Wavelet Transforms Versus Fourier Transforms," Bulletin (New Series) of the American Mathematical Society, vol. 28, No. 2, pp. 288–305, Apr. 1993.

Strang, G., "Wavelets and Dilation Equations: A Brief Introduction," SIAM Review, vol. 31, No. 4, pp. 614–627, Dec. 1989.

Taoka, G. T., "Driver Drowsiness and Falling Asleep at the Wheel," Transportation Quarterly, vol. 47, No. 4, pp. 583–595, Oct. 1993.

Timmons, B., Salamy, J., Kamiya, J., and Girton, D., "Abdominal–thoracic Respiratory Movements and Levels of Arousal," Psychon. Sci., vol. 27, No. 3, pp. 173–175, 1972.

Torsvall, L., Åkerstedt, T., Gillander, K., and Knutsson, A., "Sleep on the Night Shift: 24–Hour EEG Monitoring of Spontaneous Sleep/Wake Behavior," Psychophysuology, vol. 26, No. 3, pp. 352–358, May 1989.

Torsvall, L., and Åkerstedt, T., "Extreme Sleepiness: Quantification of EOG and Spectral EEG Parameters," International Journal of Neuroscience, vol. 38, pp. 435–441, 1988.

Torsvall, L., and Åkerstedt, T., "Sleepiness on the Job: Continuously Measured EEG Changes in Train Drivers," Electroencephalography and clinical Neurophysiology, vol. 66, pp. 502–511, 1987.

Trejo, L. J., and Shensa, M. J., "Linear and Neural Network Models for Predicting Human Signal Detection Performance from Event–Related Potentials: A Comparison of the Wavelet Transform with Other Feature Extraction Methods," Proceedings of WNN '93, Nov. 7–10, 1993 (Society for Computer Simulation, ISBN 1–56555–059–5), pp. 153–161.

Wierwille, W. W., "Overview of Research on Driver Drowsiness Definition and Driver Drowsiness Detection," presented at 14th International Conference on the Enhanced Safety of Vehicles (ESV), Munich, Germany, May 23–26, 1994.

Wierwille, W. W., Wreggit, S. S., Kirn, C. L., Ellsworth, L. A., and Fairbanks, R. J., "Research on Vehicle–Based Driver Status/Performance Monitoring; Development, Validation, and Refinement of Algorithms for Detection of Driver Drowsiness," U.S. Department of Transportation, National Highway Traffic Safety Administration, Final Report, No. DOT HS 808 247, pp. 12–18, Dec. 23, 1994.

Wierwille, W. W., Wreggit, S. S., and Knipling, R. R., "Development of Improved Algorithms for On–Line Detection of Driver Drowsiness," presented at Convergence Ninety–Four Conference, SAE International, Detroit, Oct. 1994.

Wierwille, W. W., and Eggemeier, F. T., "Recommendations for Mental Workload Measurement in a Test and Evaluation Environment," Human Factors, vol. 35, No. 2, pp. 263–281, Jun. 1993.

Wierwille, W. W., "Demands on Driver Resources Associated with Introducing Advanced Technology into the Vehicle," Transportation Research–C., (Pergamon Press Ltd.), vol. 1, No. 2, pp. 133–142, 1993.

Wikswo, Jr., J. P., Gevins, A., and Williamson, S. J., "The future of the EEG and MEG," Electroencephalography and clinical Neurophysiology, vol. 87, pp. 1–9, 1993.

Wilkinson, R. T., "Effects of up to 60 Hours' Sleep Deprivation on Different Types of Work," Medical Research Council Applied Psychology Research Unit, Cambridge, England, pp. 175–186, approx. 1963.

Williams, C. E., and Gluckman, P. D., "Real–Time Spectral Intensity Analysis of the EEG on a Common Microcomputer," Journal of Neuroscience Methods, vol. 32, pp. 9–13, 1990.

Williams, H. L., Lubin, A., and Goodnow, J. J., "Impaired Performance with Acute Sleep Loss," Psychological Monographs: General and Applied, vol. 73, No. 14, pp. 1–26, 1959.

Wolpaw, J. R., McFarland, D. J., Neat, G. W., and Forneris, C. A., "An EEG–Based Brain–Computer Interface for Cursor Control," Electroencephalography and clinical Neurophysiology, (Elsevier Scientific Publishers Ireland), vol. 78, pp. 252–259, 1991.

Yamamoto, Y., and Isshiki, H., "Instrument for Controlling Drowsiness Using Galvanic Skin Reflex," Medical and Biological Engineering & Comput., vol. 30, pp. 562–564, 1992.

Naitoh, P., Kollar, E. J., and Kales, A., Abstract: "The EEG Changes After a Prolonged Sleep Loss," abstracted in Society Proceedings (misc.), Electroencephalography and clinical Neurophysiology, vol. 26, p. 238, 1969.

"Symposium on Sleep Disorders," Mayo Clinic Proceedings, vol. 65, pp. 857–860, 1990.

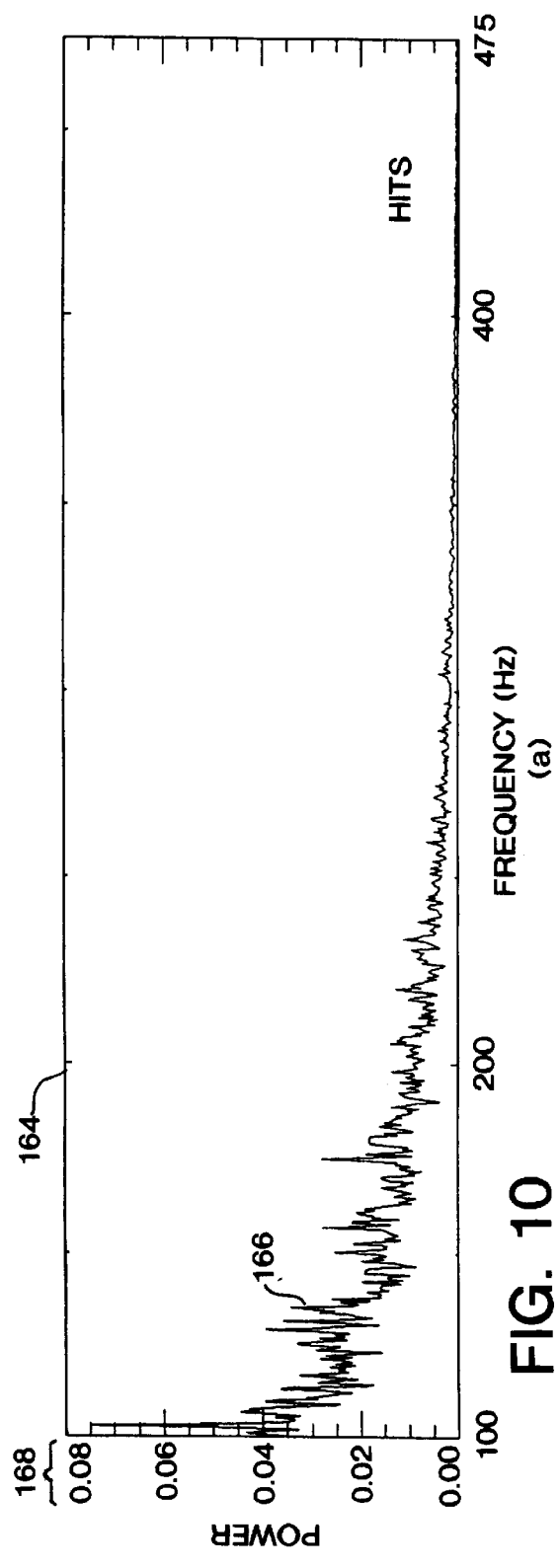
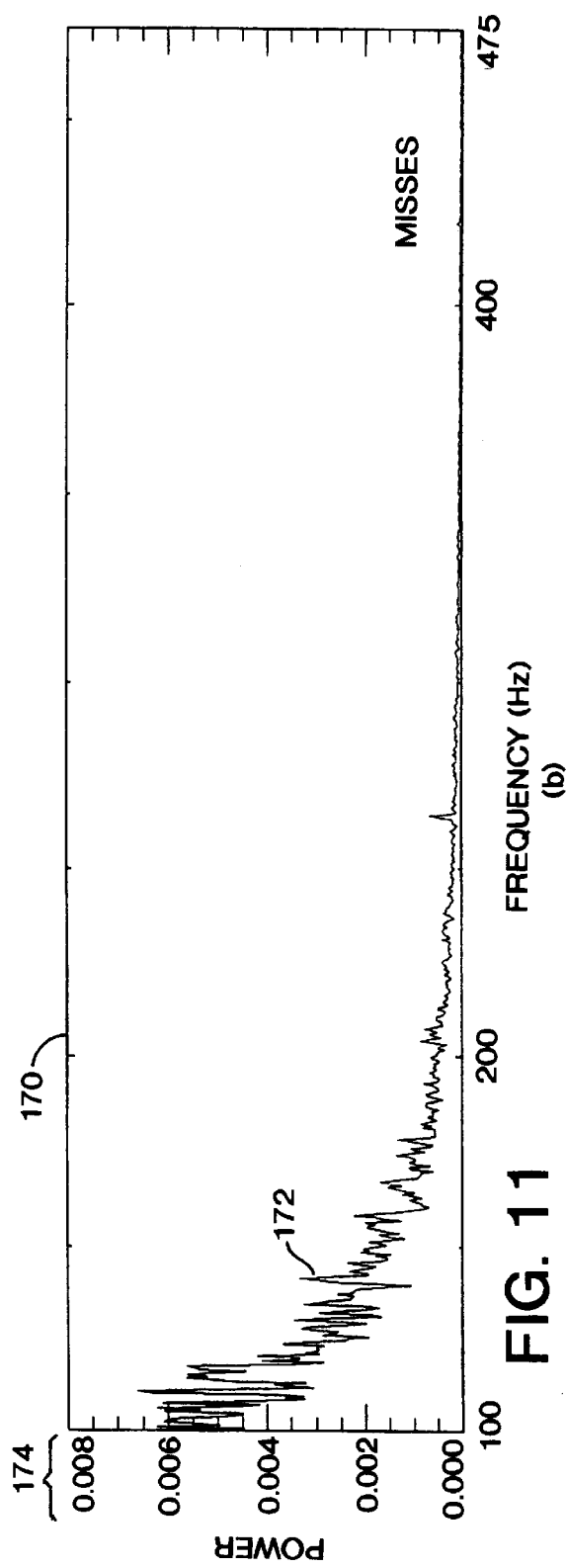

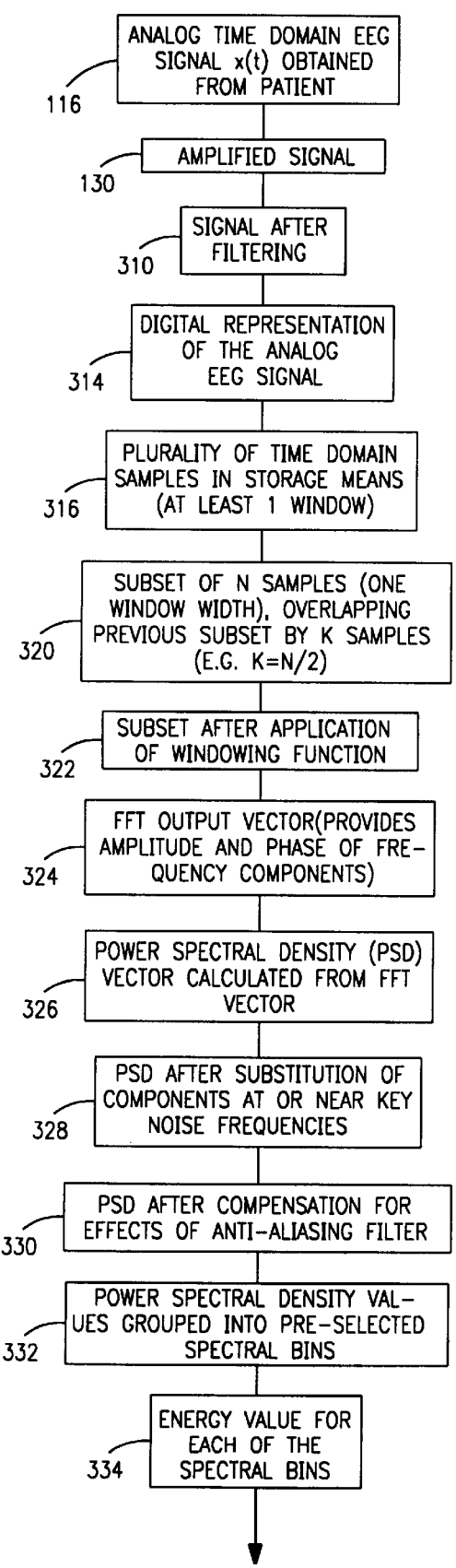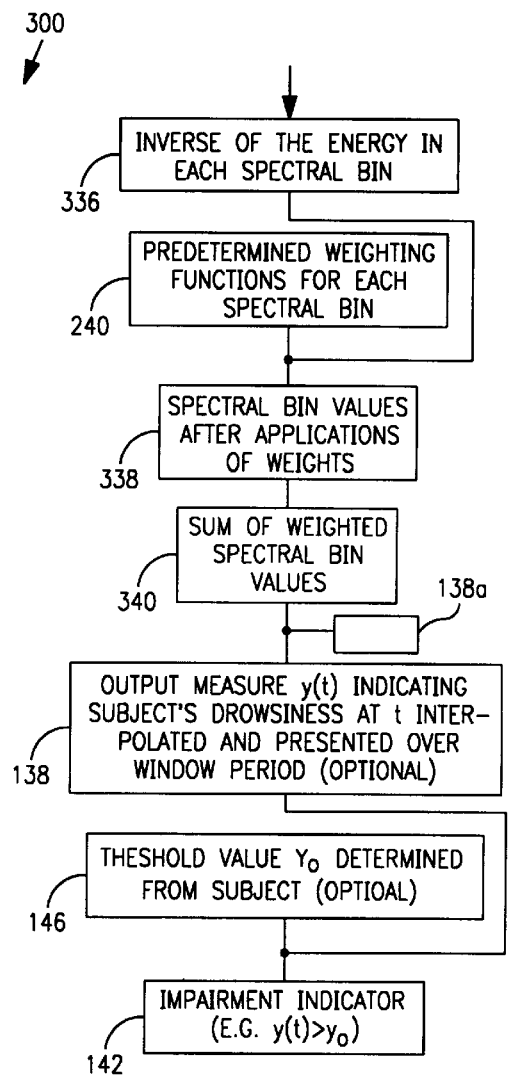
FIG. 16

ALERTNESS AND DROWSINESS DETECTION AND TRACKING SYSTEM

BACKGROUND OF THE INVENTION

This invention relates to systems for determining a subject's state of alertness and drowsiness, and more particularly to apparatus and methods for analyzing EEG signals acquired from a subject to definitively determine the subject's state of alertness, drowsiness, or his or her sleep stage, and to determine whether the subject's performance is impaired thereby.

The Need For Alertness Monitoring, Drowsiness Detection, And Sleep Staging

Sleep deprivation has become one of the most significant causes of error and accident throughout our society. The United States Department of Transportation estimates that 200,000 traffic accidents each year may be fatigue- or sleep-related. In transportation alone, sleep-related accidents annually claim over 5,000 lives, and cause hundreds of thousands of injuries, with an accumulated cost for health care, death, lost productivity, and damage to property in the billions of dollars. U.S. Department of Health and Human Services (1992).

Pilots say their schedules often force them to snooze in the cockpit in order to get enough sleep. Industry insiders report that flight attendants need to periodically check to ensure that the crew is awake. The National Transportation Safety Board (NTSB) cited pilot fatigue as either the cause or a contributing factor in 69 airplane accidents from 1983 through 1986 Stanford Sleep Disorders Clinic and Research Center (1991).

Recent analyses of spectacular accidents and catastrophes suggest that sleepiness may have played an important role in such events, including the Three Mile Island nuclear disaster and the Exxon Valdez oil spill. Mitler et al. (1988). Such accidents endangered large segments of the population and the environment.

The presidential Commission on the Space Shuttle Challenger accident ruled that ground crew fatigue was a contributing cause of the 1986 disaster. In the near catastrophic launch of the shuttle Columbia only three weeks before, operator fatigue was reported as one of the major factors contributing to this incident. Stanford Sleep Disorders Clinic and Research Center (1991). Thus the importance of human vigilance or attention is critical to the performance of individuals in various types of occupations.

Each human being requires a specific amount of sleep in each 24-hour period to maintain a functional level of alertness. If an individual obtains less sleep, he/she will be less alert the following day. Moreover, sleep loss accumulates from one night to the next as a "sleep debt." Therefore, only a modest loss of sleep per night may produce a serious sleep debt when sustained over several nights. The more sleep lost each day, the greater the sleep debt and the larger the impairment. Because individuals often do not recognize that they are sleepy, they seldom guard against involuntary sleep episodes. Much like intoxicated drivers, sleepy drivers do not realize that they are incapable of adequate performance, and may therefore deny drowsiness and impairment U.S. Department. of Health and Human Services (1992).

The effects of sleep loss can be amplified by the bi-modal circadian rhythm. Evidence of this can be found in the temporal patterns of accidents attributed to "falling asleep" or even to mere lapses in operator attention. Studies of single-vehicle truck accidents in Israel, Texas, and New York all reveal two distinct peaks in the time of day when these accidents occurred. Lavie et al. (1986); Langlois et al. (1985); G. W. Duff (unpublished observations). One peak occurs in the early morning hours from 1 a.m. to 7 a.m. and a lower peak occurs during the mid-afternoon from 1 p.m. to 4 p.m.

Another factor which raises risk of accidents is the increasing level of automation. For example, drivers using cruise control and pilots using automatic flight control systems are more susceptible to drowsiness due to the removal of stimulating influences. The Exxon Valdez was on automatic pilot during the critical minutes leading to its grounding as it hit Bligh Reef at 12:04 a.m. Stanford Sleep Disorders Clinic and Research Center (1991). The NTSB's investigation of the accident indicated that the third mate was asleep on his feet and failed to respond to the warning light and alarm identifying the reef U.S. Department. of Health and Human Services (1992). Although automation has provided tremendous benefits, it tends to limit operator activity to vigilant monitoring of the system. Over a period of time, this can reduce the awareness level of the operators and impair their ability to react properly to an external stimulus. In addition, vigilance is further degraded by sleep loss-and fatigue.

Thus, it would be highly desirable to produce an automated real-time system to track the changes in levels of alertness, such as the transition from alertness to drowsiness, or the onset of sleep. In addition, there are a number of other applications in which an automated system for measuring an individual's alertness, drowsiness, or stage of sleep would be highly useful. For example, sleep staging—i.e., the identification of a subject's stage or condition of sleep based on physiological indicators—is used clinically for diagnosing and treating sleep disorders. Sleep staging is also of interest in medical research. Normally, sleep staging is performed by a highly trained physician or technician by studying voluminous EEG records collected while a subject sleeps. A totally automated system for sleep staging could improve consistency and reduce research and treatment costs. Although the sleep scoring field is well established, the greatest disagreement among sleep scorers analyzing identical segments of sleep data occurs when scoring the transition from "stage W" (a state of wakefulness) to "stage 1" sleep (an initial stage of sleep sometimes referred to as the sleep onset period).

No system is currently available which can effectively use the EEG signal for continuous drowsiness tracking and detection. A recent report to the United States Department of Transportation (DOT) surveying methods of drowsiness detection acknowledged that automated processing of the EEG signal has proved very difficult to implement. Wierwille (1994). Various phases or stages of sleep are identifiable using automated methods. However, drowsiness and the onset of sleep are much less distinguishable in the EEG waveform, and therefore, much more difficult to identify using automated methods, than are sleep stages. Research surveyed in the DOT report suggests using a manual method of analyzing EEG and EOG signals. Wierwille (1994), citing Planque (1991).

It should be noted that in many real-world applications, it is insufficient to detect sleep, as normally understood, because it is often essential to provide a warning before an individual's performance is impaired. In particular, for critical applications in which a lack of vigilance could affect health and safety it is necessary to detect extreme sleepiness. "Extreme sleepiness" is used herein to refer to the state during which sleep is perceived as difficult to resist, the individual struggles against sleep, performance lapses occur, and sleep will eventually ensue but has not yet occurred. By detecting the onset of extreme sleepiness in an individual, the individual may be alerted, or disqualified from service, before they reach a state in which they are incapable of safely performing a task.

Prior-Art Approaches To Alertness Monitoring

A variety of methods have previously been used or proposed for detecting or evaluating sleep or drowsiness in a subject. Although some prior-art methods have been reasonably successful at automated detection of actual sleep, there has heretofore been no automated system capable of consistently and definitively detecting the onset of extreme sleepiness before an individual becomes unable to safely perform a task.

Alertness Monitoring Using External Manifestations Of Drowsiness

Several prior-art approaches to the automated sleep detection problem have relied on externally observable manifestations of sleep. For example, Chiu U.S. Pat. No. 4,875,030 discloses a system which observes the state of a subject's eyelids while performing a task, such as driving. If the subject's eyelids remain closed for a period greater than a normal blink interval, the subject is determined to be succumbing to sleep, and an alarm is given. This system could be extended to sound an alarm when some other blink-related characteristic, such as blink duty cycle or blink frequency, deviates from established norms. Kishi U.S. Pat. No. 5,311,877 discloses a system for estimating a "waking degree" (which might be a measure of alertness) using an individual's eye blink frequency or the time required for the individual to react to a visual stimulus. Estrada U.S. Pat. No. 3,953,831, discloses a system which attempts to monitor the attitude of the subject's head; if the head is observed to droop, then the subject is determined to be succumbing to sleep, and an alarm is given. Slansky U.S. Pat. No. 4,617,559, discloses a fatigue alarm system which employs a pressure-operated switch disposed in a wrapper for a steering wheel or the like; when the grip of the user becomes relaxed, the switch operates and the alarm is given.

These prior-art approaches suffer from a number of important disadvantages, especially in real-time applications involving health or safety. A primary disadvantage is that these approaches do not detect drowsiness or lack of vigilance early enough. If a subject closes his or her eyes, or allows his or her head to droop, and that behavior is the result of drowsiness, then the subject may already be at the far end of the drowsiness spectrum, and performance may already be impaired. In certain applications, eye closure or head drooping is meaningless in a drowsiness detection system, because such behavior is neither necessary nor sufficient for a conclusion of drowsiness or sleep. For example, there are some environments in which the subject is permitted to rest his or her eyes for brief intervals, provided that he or she remains awake and vigilant. Furthermore, detection of eye closure or head drooping produces a binary output, which has no further sensitivity once the targeted behavior has been detected. Thus, in the aforementioned example, once the subject closes his or her eyes, the system cannot distinguish among wakefulness, drowsiness, or sleep.

Another disadvantage of these approaches is that it is relatively difficult in practice to usefully monitor a subject's physical activity, such as the state of a subject's eyes or head position. This disadvantage is further compounded by the difficulty in using information about physical activity to distinguish fatigue from transient, but normal, variations in behavior. Estrada, for example, discloses using a mercury switch to monitor the position of the subject's head. Such a switch provides a discrete-valued output, is difficult to adjust, and may produce false indications during normal subject and vehicle movement. Although imaging systems have been proposed for capturing and interpreting an image of the subject's eye or eyes, such systems require expensive image and signal processing components. Further, any imaging system must contend with: various eyewear and clothing which the subject may employ (e.g., prescription glasses, sunglasses, contact lenses, hats); large variations in normal lighting conditions; contamination of the vehicle environment by high-amplitude spurious lighting (e.g., illumination by the headlights of another vehicle); and normal movement by the subject.

Seko et al. U.S. Pat. Nos. 4,564,833 and 4,604,611 disclose drowsiness detection systems for motor vehicles which detect the onset of sleep in a driver by observing a change in the number, rate, or amplitude of certain steering inputs. When a vehicle is being driven along a linear path, the driver typically makes frequent steering corrections by performing a series of small displacements of the steering wheel in either direction. Because these displacements typically are small in magnitude and frequently are in the direction opposite that of the previous displacement, they are sometimes referred to as "micro-reversals." As a driver falls asleep, the resolution of the driver's steering control degrades. This is detectable as a change in the frequency and amplitude of steering inputs. As a driver becomes sleepy and loses attentiveness, or if the driver falls asleep for a brief instant and then awakens, the driver will have failed to provide appropriate steering inputs during that interval. Upon awakening or regaining attentiveness, the driver attempts to rapidly supply steering inputs which correct the entire steering error that accumulated during the sleep interval. Thus, changes in the pattern of steering reversals may indicate that the driver has fallen asleep or is about to do so.

This method of detecting drowsiness or sleep also has a number of disadvantages. It is difficult to distinguish between abnormal changes in steering patterns caused by the onset of sleep and normal steering pattern changes required by road or traffic conditions which may mimic drowsiness- or sleep-induced changes. As a result, systems which rely on this method are prone to false alarms. The method also fails to take into account characteristics of individual drivers. In addition, because this method relies on measurement of the subject's actual task performance, it does not detect the onset of sleep until the subject's performance is already noticeably impaired. Such detection may not provide sufficient warning to avoid an accident. Furthermore, many tasks which require vigilance do not employ any user inputs under normal conditions; other tasks require some user inputs, but such inputs may not form recognizable patterns from which abnormal user behavior may be distinguished.

Alertness Monitoring Using Internal Manifestations Of Drowsiness

Other prior-art automated sleep detection approaches have attempted to measure directly one or more of a subject's internal physiological characteristics which may indicate alertness or drowsiness. Yoshimi et al. U.S. Pat. No. 4,928,090 discloses a system for judging "arousal level" based on a measurement of skin potential level. A disadvantage of this system is that skin potential level may be affected by many factors other than arousal or drowsiness, and therefore it is difficult to distinguish drowsiness-related changes in skin potential level and changes caused by other factors.

EEG-Based Approaches

The electroencephalogram (EEG) is a recording of the low-voltage electrical activity produced in specific regions of the brain. The EEG provides a powerful tool for studying both normal and abnormal brain function, and has been commonly used to measure and define wakefulness and sleep. There is considerable evidence that physiological sleepiness is directly related to the rapidity of the onset of EEG-defined sleep. Torsvall et al. (1987); Torsvall et al. (1989); Akerstedt et al. (1990); Akerstedt et al. (1991); Wierwille et. al. (1992); Dinguset. al. (1987).

Sleep is regarded as an active and complex state, and has been characterized in terms of various stages and cycles. The term "sleep architecture" is used to describe these stages and cycles. The stages and cycles of sleep may be defined using both external manifestations and internal physiological processes which can be externally measured, such as EEG and electrooculogram signals.

The electrooculogram (EOG) is a recording of the low-voltage electrical activity associated with eye movement. It has been observed that the transition to sleep is also frequently accompanied by slow rolling eye movements (SEMs) that can be detected in EOG signals.

EEG signals include both periodically recurring or rhythmic features (waves), and transient features, such as "spindles," which do not recur on a periodic basis and are highly localized in time. One method of summarizing and evaluating the content of EEG records is through analysis of frequency components contained in the EEG signal. Traditional EEG doctrine states that the information content of an EEG signal is band-limited between roughly 0.5 and 30 Hz. Within this range, standardized names have been given to individual frequency bands. (See Table 1).

TABLE 1

TRADITIONAL EEG SIGNAL FREQUENCY BANDS

| Band Name | Lower Limit (Hz) | Upper Limit (Hz) |
|---|---|---|
| Delta | 0.5 | 2 |
| Theta | 3 | 7 |
| Alpha | 8 | 12 |
| Beta | 13 | 30 |

A substantial amount of research has been conducted in an attempt to characterize the relationships between a subject's EEG waveforms, the subject's state of alertness, drowsiness, or sleep, and the subject's ability to perform a task. The relationship between performance degradation (slower reaction rates and attention lapses) and increased sleepiness has been established by several researchers. Wilkinson and Houghton (1975); O'Hanlon and Kelley (1977); Dinges (1988); Molodofsky (1992); Trejo and Shensa (1993); Makeig and Inlow (1993). Similarly, a strong correlation has been noticed between performance degradation and particular patterns in the EEG waveform. Horvath et al. (1976); O'Hanlon and Beatty (1977); O'Hanlon and Kelley (1977); Makeig and Inlow (1993). In turn, the EEG waveform has also been correlated with vigilance and sleepiness of subjects in various studies. Gale (1977); Daniel (1967); Fruhstorfer et al. (1977); Santamaria and Chiappa (1987). Kishi U.S. Pat. No. 5,311,877 purports to employ "brain waves" and performance measurement in A system for estimating a "waking degree." Although the meaning of the term "waking degree" is unclear, it is treated as equivalent to reaction time (see FIG. 11), and it might be a measure of alertness. Kishi discloses the use of "brain waves" analyzed by a "brain wave processor" to supply inputs to the waking degree estimation unit. However, the particular analysis performed is unclear, and it is likewise unclear what relationship may exist between a subject's brain waves and his or her waking degree, or how any such relationship might be exploited.

Sleep researchers rely on the EEG in the classification of various phases or stages of sleep. However, compared to sleep stages, drowsiness and the onset of sleep are not as easily distinguishable in the EEG waveform. In particular, when drowsiness or sleep onset occur, the changes directly apparent in the EEG waveform are less profound, and may be masked by events or processes which affect the EEG but which are not directly related to drowsiness.

Alertness Monitoring Using EEG Frequency Analysis

One commonly applied method of analyzing EEG signals has been to study the frequency bands in which significant or predominant components of the signals reside. The term "predominant" is used herein to refer to the frequency bands or components which contain most of the energy in EEG signals. The research to date indicates that drowsiness is associated with a re-distribution of energy in the traditional frequency bands toward lower frequencies. However, it is difficult to use this general guideline in a drowsiness detection system because of the varied characteristics of EEG signals among subjects. For example, subject behavior and physiology unrelated to drowsiness can produce changes in the EEG which are similar to those correlated with drowsiness.

Additionally, whether the eyes are open or closed can make a substantial difference in the level of activity in particular frequency bands of interest in the EEG. Based on sleep stage classification studies, Smith claims that the EEG can be used to identify states of severe sleepiness if the subject's eyes are open. Smith (1987). In alert subjects with their eyes open, the predominant energy in the EEG signal appears in the beta frequency band (13–30 Hz). A shift of energy into the alpha band (8–12 Hz) occurs as the subjects become drowsy. O'Hanlon and Beatty (1977). For an individual with his or her eyes open, studies clearly indicate that increases in alpha and theta activity in the EEG may correlate with sleepiness as well as reduced performance. Fruhstorfer et al. (1977); O'Hanlon and Kelley (1977); Daniel (1967); Horvath et al. (1976); O'Hanlon and Beatty (1977). Thus, the appearance of alpha activity in the EEG may be an indicator of drowsiness (an incipient indicator of a loss of vigilance), if the subject has his or her eyes open. Santamaria and Chiappa (1987); Makeig and Inlow (1993).

If the subject's eyes are closed, however, it is much more difficult to differentiate between sleepy and alert states. Smith (1987). In individuals with eyes closed, EEG signal energy is predominantly located in the alpha frequency band even though they are wide awake. As sleepiness develops, a subject whose eyes are closed generally experiences a reduction in alpha band energy and an increase in theta band energy (and possibly delta band energy) present in the occipital channel of an EEG. Smith observed a pattern of SEMs during sleepiness with "open eyes" and reported that the studied subjects alternated between open and almost closed eyes. Smith (1987). This may be an explanation for the increased alpha activity observed during drowsiness. Thus, when the EEG of an initially-alert individual with eyes open displays a shift in predominant energy from the beta band to the alpha band, that shift might indicate that the individual has become drowsy, but it also might simply indicate that the individual has closed his or her eyes but otherwise remains alert. O'Hanlon and Beatty (1977); Makeig and Inlow (1993); Santamaria and Chiappa (1987).

A number of known techniques seek to characterize the subject's state of alertness or sleep by observing the re-distribution of energy in the subject's EEG signal among the traditional frequency bands. Some of these refinements are directed to examining ratios of the energies present in two or more frequency bands, or examining the ratio of the energy contained in a predefined frequency band to the total energy in the 0–30 Hz band.

Other techniques of EEG signal analysis, which do not principally rely on the frequency domain, have also been tried. Sleep spindles and K-complexes are perturbations in the EEG signal which are associated with stage 2 sleep and are generally recognizable in the time domain. But the presence of sleep spindles and K-complexes occurs too late to be useful in detecting drowsiness. Researchers have also tried to use SEMs, which are detectable in EOG signals, as an indicator of drowsiness. However, none of these have produced a reliable indicator of drowsiness.

Thus, although it is clear that there exists some information in EEG signals which indicates drowsiness, and although some prior-art methods have been reasonably successful at automated detection of actual sleep, heretofore there has been no automated system capable of consistently and definitively detecting the onset of extreme sleepiness (which functions as a precursor to sleep).

Inadequacies In Prior-Art Methods Of Acquiring, Recording, And Analyzing EEG Signals Although the acquisition and recording of EEG signals from human subjects has been practiced for many years, conventional acquisition and analysis techniques have not resulted in strong and consistent correlations between the EEG signal and alertness. FIG. 1 is a simplified block digram of a system 60 typical of those used for recording and analyzing EEG signals for the primary purpose of medical diagnostics.

At least one signal electrode 64 and at least one reference electrode 66 are coupled to a subject 62 from whom it is desired to receive EEG signals. Although only one signal electrode 64 is shown, it is common in clinical and research applications to place signal electrodes at several standard locations on the subject's head to obtain EEG information which correlates with various physiological and or cognitive processes that occur in different regions of the brain. The electrodes 64, 66 are typically mechanically secured to the subject's scalp to provide a relatively low impedance electrical connection therewith; often, a conductive gel or paste is used to enhance the conductivity of the connection.

Although one electrode 66 is designated as the "reference" electrode, such designation is arbitrary because the EEG signal is measured differentially. The electrodes 64 and 66 and certain related signal acquisition components (to be further described) may represent a plurality of duplicate sets of electrodes and related signal acquisition components.

In both clinical and research applications, the traditional means of displaying and recording EEG signals has been to supply the amplified signals to a "pen recorder" 74 as shown in FIG. 1. A pen recorder typically has a strip of paper or chart medium 76 which moves at a predetermined speed in a longitudinal direction corresponding to the time axis of the chart. One or more pens 88 are mounted to trace one or more continuous lines on the chart as the chart moves longitudinally. A suitable mechanism causes transverse displacement of the pen responsive to a corresponding electrical signal input, so that the pen traces a record of the amplitude of the signal input over time.

With respect to EEG signals, the human body is a relatively high-impedance source which produces very low voltage signals (in the microvolt range) at very low currents. In order to provide sufficient signal amplitude to drive the pen recorder 74, the EEG signals must be amplified. The electrodes 64, 66 are connected to an EEG amplifier 70 using suitable leads 68, which are selected to minimize noise contamination. Leads 68 may be provided with a shield 58 as an additional noise reduction step. The EEG amplifier 70 is typically a high-quality high-input-impedance linear amplifier having a several user-selectable gain settings in the range of $10^3$–$10^5$. A variety of EEG amplifiers are available as commercial products and in various configurations; one EEG amplifier popular in clinical applications is a component of a commercially available product sold under the name "Grass Instruments Model 12C Neurodata Acquisition System".

Traditional EEG doctrine states that the information content of an EEG signal is band-limited between roughly 0.5 and 30 Hz. In addition, pen recorders necessarily have limited bandwidth because they incorporate electromechanical transducers. Accordingly, conventional EEG acquisition systems include a suitable filter (shown in simplified form as filter 70 of FIG. 1) as part of the amplifier electronics. Typically, a first-order Butterworth type filter with a 50% amplitude response at approximately 30 Hz is used. FIG. 2 is a graph 88 showing the 1–500 Hz frequency response 90 experimentally derived from a commercial EEG filter of the first-order Butterworth type, which is available as a component of the aforementioned "Grass Instruments Model 12C Neurodata Acquisition System." As best seen in FIG. 2, such a filter has a −3 dB point at approximately 21–22 Hz, and a filter roll-off of approximately 20 dB per decade. Also, in many environments, there may be a large amount of electrical noise at the commercial power-line frequency (60 or 50 Hz). Substantial contamination of EEG signals can occur at these frequencies, and therefore, most commercial EEG equipment provides additional filtering to minimize the effect of this contamination.

The analysis of EEGs generally involves the opinions of expert clinicians in conjunction with an off-line data analysis procedure. In order to display and record the signal, the amplified and filtered EEG signal 78 is typically supplied to the pen recorder 74. In some applications, it may also be desirable to record or process the EEG signal in electronic form. The amplified and filtered EEG signal 78 may be supplied to an optional post-processing system 80 for storing and processing the signal. The post-processing system 80 may employ any of a wide variety of storage means 82, such as instrument tape recorders and digital storage systems. Any suitable post-processing functions 84 may be applied to the EEG data stored in storage means 82. The results of processing the EEG data may be provided on a lead or data path 86.

In some applications, the signal 78 may be converted using conventional techniques into digital form for storage on any suitable digital storage medium. When a band-limited analog signal is periodically sampled for conversion into digital form, according to Nyquist's theorem the sampling frequency must be at least two times the highest frequency in the analog signal. Accordingly, in applications where EEG signals have been recorded and processed digitally, sampling rates have generally been in the range of 90–275 Hz. EEG examinations may employ one or several electrodes. Because the examinations are conducted over periods of five minutes to several hours, a large amount of data must be collected, stored, and processed. Accordingly, it is highly desirable to minimize the sampling rate to the extent possible consistent with EEG signal bandwidth in order to minimize the amount of data storage and post-processing required.

FIG. 3 is a graph 92 showing an excerpt of a sampled EEG waveform 94 acquired from a human subject using conventional EEG recording techniques as generally shown in FIG. 1. This sample waveform was obtained from the occipital EEG channel of an awake subject during an alertness test in which the subject was presented with a time-separated series of visual stimuli and scored on their ability to promptly respond to each stimulus. This sampled waveform corresponds to a successful response. This waveform shows the amplitude of the EEG signal in microvolts over a 2-second interval and was acquired at a sampling rate of 256 Hz, resulting in 512 data samples.

FIG. 4 is a graph 96 showing the power spectral density 98 of the sampled waveform depicted in FIG. 3, over the frequency range 0–128 Hz. The energy within the 0–30 Hz range accounts for more than 99% of the total spectral energy. Although approximately 1% of the total spectral energy is contained in the frequency range above 30 Hz, it is not visible on the graph of FIG. 4, which is scaled for viewing the predominant frequency content in the 0–30 Hz range.

An interesting feature of graph 96 is the pair of prominent peaks 56 and 58 appearing in the power spectrum in the range of 9–11 Hz, which is within the alpha frequency band. These peaks account for approximately 50.5% of the total energy in the spectrum. Established EEG doctrine asserts that predominant alpha band energy in the EEG of a subject whose eyes are open is an indication of extreme drowsiness and is often associated with poor task performance. Surprisingly, although alpha band energy was present (and even predominant) in this sample, performance was not only acceptable, but corresponds to one of the fastest reaction times this subject achieved. (The fact that the subject responded to the visual stimulus, and corresponding data from a simultaneously acquired vertical electrooculogram (EOG) signal, verify that the subject's eyes were open.) This type of contradiction between a subject's alertness, as demonstrated by task performance, and that predicted from the subject's EEG signals according to traditional doctrine can be seen in other test samples. Therefore, an alertness monitoring system that relies heavily on the presence or shift of the predominant energy in rhythmic EEG signals among the frequency bands that have traditionally been of interest in EEG research is prone to error in the form of disagreement between predicted and actual behavior.

It is taught throughout the EEG literature and assumed in the design of prior-art alertness monitoring systems that all of the useful information in the EEG signal is contained in the 0–30 Hz frequency band. For example, Kishi U.S. Pat. No. 5,311,877 purports to employ "brain waves" and performance measurement in a system for estimating a "waking degree." However, Kishi's brain wave processor provides band-pass filters to select only the traditional EEG frequency bands, and is thus not directed to analysis of EEG signal components above 30 Hz.

It is believed that all methods, analyses, and systems built on the hypothesis that the useful information in the EEG signal is contained in the 0–30 Hz band share the following characteristics:

1. the analysis focuses on the frequency band of the EEG signal containing the predominant energy;
2. the analysis is directed to rhythmic signal activity at frequencies below approximately 30 Hz (i.e., exclusively in the standard frequency bands according to conventional EEG literature); and
3. the analysis treats as noise, or otherwise discards signal components above approximately 30 Hz (e.g., by low-pass filtering).

We have observed that higher-frequency components of EEG rhythms, although not the predominant components, nonetheless contain information useful for automated monitoring of alertness and drowsiness.

Although some research in the EEG field has employed wider filter bandwidths and higher sampling rates to preserve frequency components in the EEG signals above 30 Hz, such research has generally been directed to the detection of physiological conditions other than drowsiness or sleep or has primarily relied on analysis of transient or non-periodic events. There are several well-known transient events during which higher frequency components (above 30 Hz) are present in the EEG signal. Common sources of high frequency energy are most often associated with burst activity such as the neurological "spike" activity observed during an epileptic seizure, and muscle/movement artifact. Muscle/movement artifact is an extremely common source of high-frequency contamination found in nearly every EEG record. Sleep spindles are brief bursts of 12–14 Hz activity in the EEG signal which have been associated with Stage 2 sleep. Sleep spindles are events which are highly localized in time and are detectable primarily using time-domain analysis. Because they occur only late in a subject's sleep cycle, they are not generally useful in monitoring alertness or drowsiness.

Researchers trying to identify spike activity in the EEG (commonly required in epileptic research) have increased the bandwidth of their low pass (anti-aliasing) filters and have used faster sampling rates during digitization. Because the high frequency components in spike or burst activity are highly localized and sharply defined in the time domain, researchers use increased filter bandwidth and sampling rates to capture more of the frequency content of the spike, thereby improving identification, analysis, and reconstruction in the time domain.

Researchers interested in transient, time-domain events generally have not employed frequency analysis techniques to study them. For example, Olsen et al. U.S. Pat. No. 5,311,876, discloses a system for automatic seizure detection using EEG signals, and uses a sampling rate of 200 samples per second. However, Olsen is directed to detecting seizures, not drowsiness, and attempts to classify events or features in the signals using time-domain analysis techniques, such as counting the number of signal extrema which occur in an analysis epoch.

The transient time-domain events to which the aforementioned EEG research has been addressed should not be confused with the continuous appearance of high-frequency energy or "rhythms." We are unaware of any prior art establishing the presence of sustained high frequency rhythms in EEG signals or relating such rhythms to alertness, drowsiness, or sleep.

The current literature discourages those skilled in the art from exploring the usefulness of high frequency rhythmic activity in EEG signals. For example, Gaillard refers to frequencies above the beta band as "high frequency noise". Gaillard (1987), 9–11. Pritchard refers to the higher frequency signals as white or near-white noise. Pritchard (1995), 378. Carskadon and Rechtswchaffen state that an upper filter cut-off frequency in the range of 30 to 35 Hz will generally pass through the "essential" wave forms, while minimizing high frequency interference. Carskadon and Rechtswchaffen (1987), 668. O'Hanlon and Beatty also refer to "noise" greater than 30 Hz. O'Hanlon and Beatty (1977), 195. Thus, all of the prior art relating to EEG-based sleep detection has either ignored evidence of higher frequency rhythmic activity in the EEG, or has failed to recognize that such activity may be usefully correlated with alertness and drowsiness in a practical monitoring or detection system.

OBJECTS AND SUMMARY OF THE INVENTION

It is therefore an object of the present invention to provide an automated alertness and drowsiness monitoring system which avoids the disadvantages of prior-art systems.

It is another object of the invention to provide an automated alertness and drowsiness monitoring system which reliably provides an indication when a subject becomes excessively drowsy.

It is a further object of the invention to provide an automated alertness and drowsiness monitoring system which reliably provides an indication of drowsiness before a subject becomes incapable of safely performing a task.

It is another object of the invention to provide an automated alertness and drowsiness monitoring system which reliably provides as an output a continuous measure representing the alertness or drowsiness of a subject.

It is a further object of the invention to provide an automated alertness and drowsiness monitoring system which provides an indication of a subject's alertness or drowsiness based on information in a subject's EEG signal, including frequency components above 30 Hz.

It is another object of the invention to provide an automated alertness and drowsiness monitoring system which provides an indication of a subject's alertness or drowsiness based on information in a subject's EEG signal, including non-predominant components thereof.

It is a further object of the invention to provide an automated alertness and drowsiness monitoring system which provides a reliable indication of a subject's alertness or drowsiness from a subject's EEG signal, and which is suitable for use in real-time applications.

A drowsiness detection system constructed according to the present invention avoids the aforementioned disadvantages of the prior art by preserving and analyzing newly discovered rhythmic signal components in selected frequency bands which the prior art has universally ignored or discarded as "noise."

An EEG-based system for monitoring or detecting alertness, drowsiness, and sleep is provided which exhibits improved performance over prior-art systems in detecting the onset of drowsiness in a human subject before the subject actually succumbs to sleep or suffers a performance failure. The system is referred to herein as a drowsiness monitoring or drowsiness detection system, although the invention may also find application in alertness monitoring, sleep staging, state-of-consciousness monitoring, anesthesia monitoring, and other related applications. According to the invention, subject drowsiness is strongly correlated with the energy present in certain rhythmic components of the subject's EEG signal at frequencies above 30 Hz.

An EEG-based drowsiness monitoring system constructed according to the present invention includes: acquisition components, signal analysis components, artifact detection components, and threshold components. The signal acquisition components sense the subject's EEG signal, amplify the signal for further analysis, and filter certain signal components which apparently do not contain useful information and which degrade further processing and analysis steps. The signal analysis component receives the amplified and filtered EEG signal, determines the amplitudes or energies of the components located in several predefined frequency ranges, including at least a portion of the frequency range 30–500 Hz, and determines an output measure signal which represents the drowsiness of the subject. The artifact detection components examine the subject's EEG signal, and optionally examine secondary indicators of the subject's physical activity, and determine therefrom whether the subject's EEG signal acquired during a particular time interval is likely to be contaminated by artifact, and therefore should not be used in drowsiness detection. The threshold component establishes a threshold against which the output measure of the signal analysis component may be compared to determine whether the output measure indicates that the subject is excessively drowsy. The threshold may be determined for the subject under examination using EEG signals collected from the subject in a known state of alertness, or may be a universal threshold applicable to the population as a whole.

In first and second embodiments of an EEG signal analysis component constructed according to the invention, primarily digital signal processing techniques are used. The analog EEG signal is sensed, amplified, and low-pass filtered for anti-aliasing. Next, the analog signal is converted to a digital signal by an analog to digital converter system. The digital signal may be analyzed online in real time, or may be stored for off-line processing and analysis. During analysis, a series of small overlapping windows or batches of data corresponding to brief time intervals of the signal are sequentially selected. Frequency analysis (e.g. a Fast Fourier Transform (FFT)) is used to convert the time-domain signal into a frequency domain output vector. Because the EEG signal is non-stationary, a windowing function is applied prior to frequency analysis. The power spectral density (or "power spectrum") of the FFT output vector is determined, in order to obtain the power in each frequency component. The power spectrum components are grouped into a small number of pre-selected spectral bins which correspond to predefined frequency ranges. The spectral bin components are aggregated to determine the total energy in each bin, and each of the resulting spectral bin energy values is inverted. Weights are applied to the respective inverted spectral energy values. An "output measure" signal is determined as the sum of the weighted inverted energy values. The output measure is a continuous-valued signal indicating the drowsiness of the subject. The output measure may be compared with the aforementioned threshold to produce a simplified output signal indicating, for example, that the subject is approaching extreme drowsiness, or is asleep, or is likely to be incapable of safely performing a task.

In a third embodiment of an EEG signal analysis component constructed according to the invention, primarily analog signal processing techniques are used. The signal processing components are broadly analogous to the digital signal processing components provided in the first and second embodiments.

BRIEF DESCRIPTION OF THE DRAWINGS

These and other features of this invention will be best understood by reference to the following detailed description of a preferred embodiment of the invention, taken in conjunction with the accompanying drawings, in which:

FIG. 10 is a graph showing the power spectral density (PSD) calculated by averaging the PSDs over the frequency range 100–475 Hz from 25 EEG data segments collected during experimental trials in which a subject successfully responded to a presented stimulus;

FIG. 11 is a graph showing the power spectral density (PSD) calculated by averaging the PSDs over the frequency range 100–475 Hz from 20 EEG data segments collected during experimental trials in which a subject failed to respond to a presented stimulus;

FIG. 16 is a data-flow diagram depicting, in simplified form, the processing of EEG signal information acquired from a subject to produce a useful output measure indicating the drowsiness of the subject, as that information is operated upon by the processing means of the embodiments of FIGS. 5 and 14–15;

DETAILED DESCRIPTION OF THE PREFERRED EMBODIMENTS

According to one aspect of the present invention, an EEG-based alertness and drowsiness monitoring and detection system is provided which exhibits improved performance over prior-art systems in detecting the onset of drowsiness in a human subject before the subject actually succumbs to sleep or suffers a performance failure. The inventive system also provides improved performance in a variety of other applications requiring monitoring, detection, or continuous tracking of a subject's state of alertness, drowsiness, or sleep. The inventive system also may provide improvements in applications relating to other aspects of a subject's alertness, which may not necessarily relate to sleep, such as monitoring aspects of a subject's state of consciousness or response to anesthesia. Thus, although the system disclosed herein will generally be referred to henceforth as a "drowsiness monitoring system" or "drowsiness detection system," the scope of the present invention shall not be limited by the use of this shorthand terminology.

Broadly defined, an EEG-based drowsiness monitoring system constructed according to the present invention comprises: means for acquiring one or more EEG signals from a subject; means for filtering the acquired signals to eliminate signal components which are unimportant or spurious, while retaining signal components having a usable correlation with the subject's state of alertness or drowsiness; means for processing the signals to select particular components which are relevant to alertness and drowsiness and to measure characteristics of the selected signals; means for eliminating certain signal information which, based on analysis of the EEG signals or on external information, appears to be contaminated by events unrelated to the subject's alertness or drowsiness; and means for determining an output measure which indicates the subject's alertness or drowsiness. Optionally, the system may also comprise means for comparing the output measure to a threshold to produce a simplified output signal indicating, for example, that the subject is approaching extreme drowsiness, or is asleep, or is likely to be incapable of safely performing a task.

An EEG-based drowsiness monitoring system constructed according to the present invention may take several different forms. Therefore, this patent application discloses three preferred embodiments of the invention, from which an appropriate one may be selected depending on the particular environment in which the invention is to be applied and on the cost and availability of implementing technologies.

Figure 5:
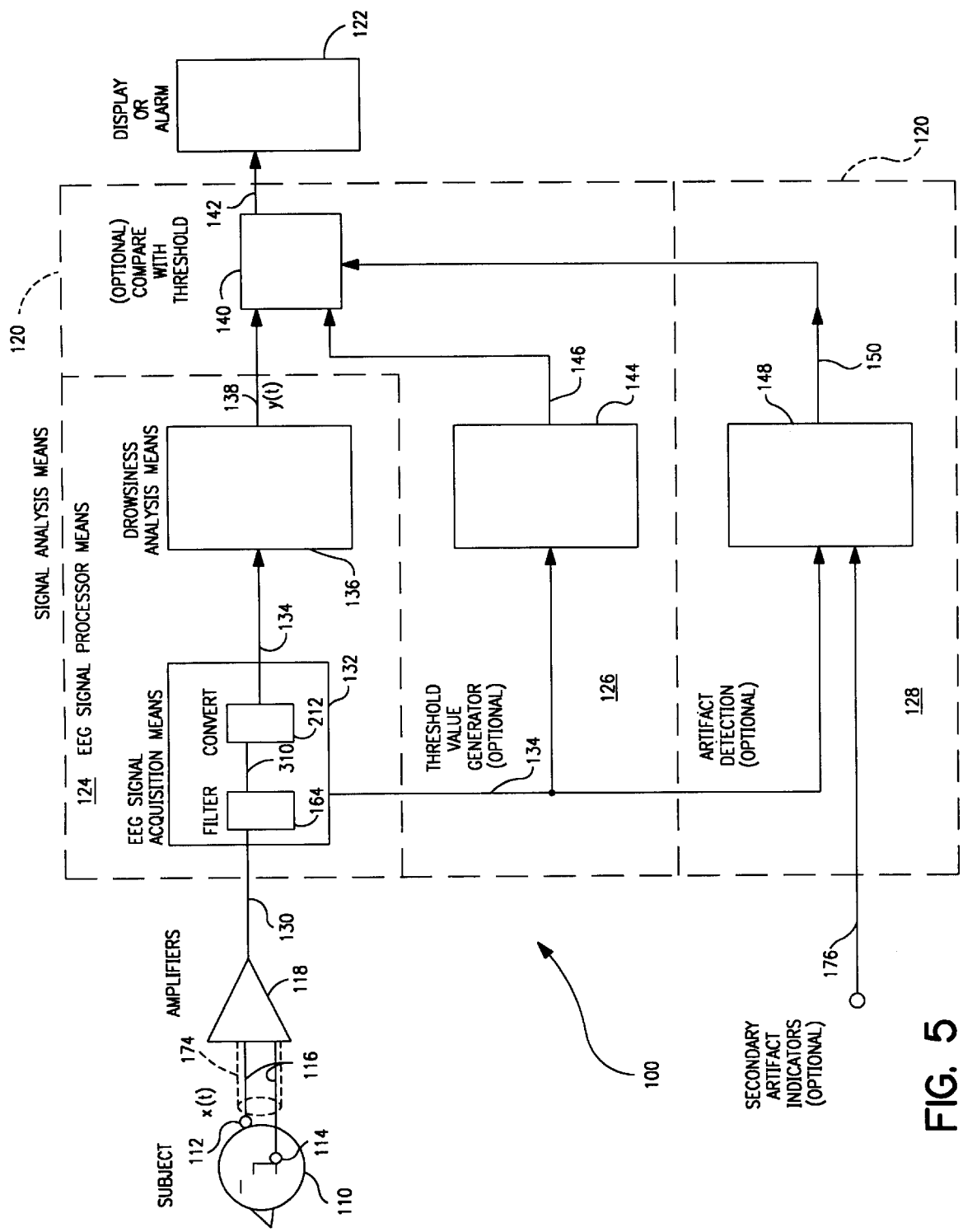
FIG. 5 is a simplified block diagram showing the general structure of first and second embodiments of an EEG-based drowsiness monitoring system which is constructed according to the present invention and which is adapted for use with digital signal processing and related techniques.
Figure 17:
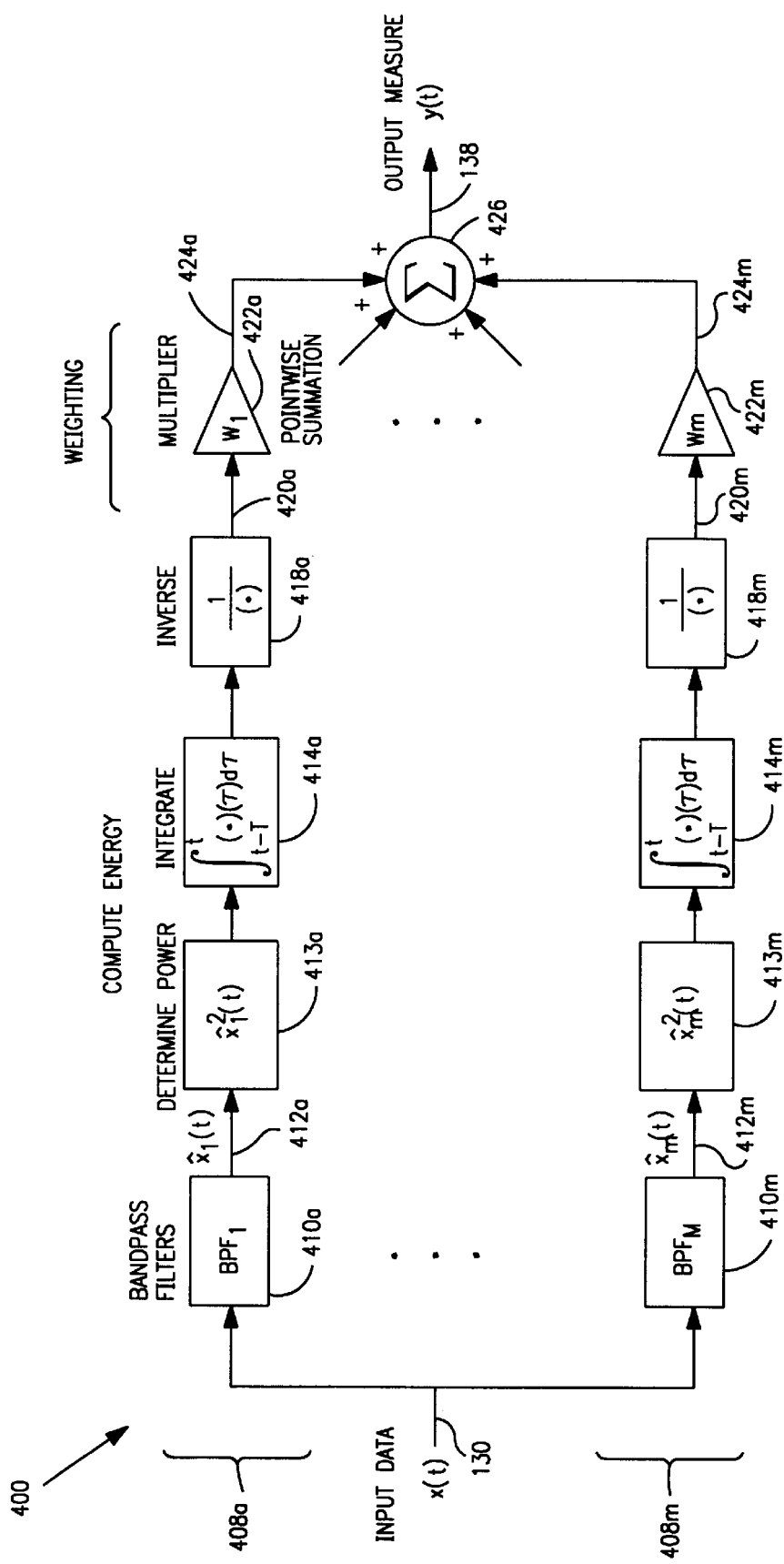
FIG. 17 is a block diagram of a third embodiment of an EEG-based drowsiness monitoring system which is constructed according to the present invention and which is adapted for use with analog signal processing and related techniques.

FIG. 5 is a simplified block diagram showing the general structure 100 of a drowsiness detection system constructed according to an aspect of the present invention. FIG. 5 is a generic drawing which is applicable to all three specific embodiments with the understanding that everything outside block 124 is optional and may or may not be present in the specific embodiments. FIGS. 12a, 12b, 14, and 16 show the structure of a first preferred embodiment 700 of the invention. FIGS. 13a, 13b, 15, and 16 show the structure of a second preferred embodiment 800 of the invention. The first and second preferred embodiments share many similarities in their methods of acquiring, processing, and analyzing EEG information, and may be primarily implemented using digital signal processing and related technologies. Thus, these two embodiments will often be discussed together in this application. FIG. 17 is a simplified block diagram showing the structure of the third preferred embodiment 400. The third preferred embodiment of the invention may be primarily implemented using analog signal processing and related technologies.

Although these three embodiments may be implemented using different technologies, according to one aspect of this invention, they all share the features of: including particular EEG signal components which have heretofore been discarded or ignored in accord with the teachings of the prior art; and exploiting the information contained in these components to provide a reliable measure of a subject's alertness or drowsiness. The analog signal processing functions of the third embodiment are analogous to those performed using digital signal processing in the first two embodiments. Accordingly, the first and second embodiments will be discussed first, and the third embodiment will be discussed subsequently with reference to analogous signal processing functions of the first and second embodiments.

Figure 12A:
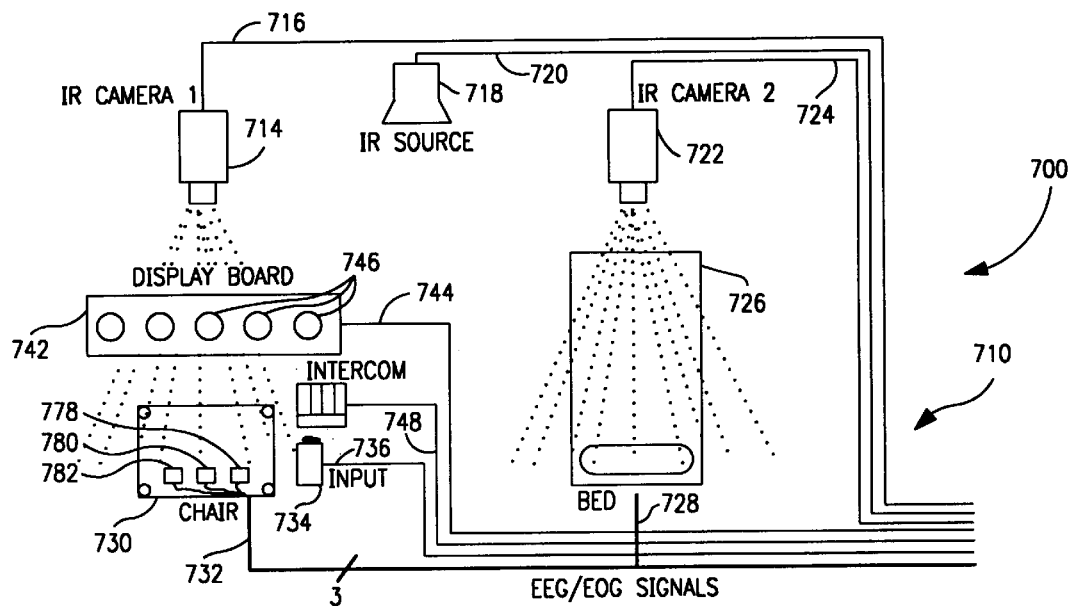
FIG. 12a is a block diagram showing the configuration of the subject interface portion of a first embodiment of the inventive drowsiness monitoring system shown generally in FIG. 5, the embodiment being adapted for collecting drowsiness-relate EEG data in a clinical or research environment.
Figure 12B:
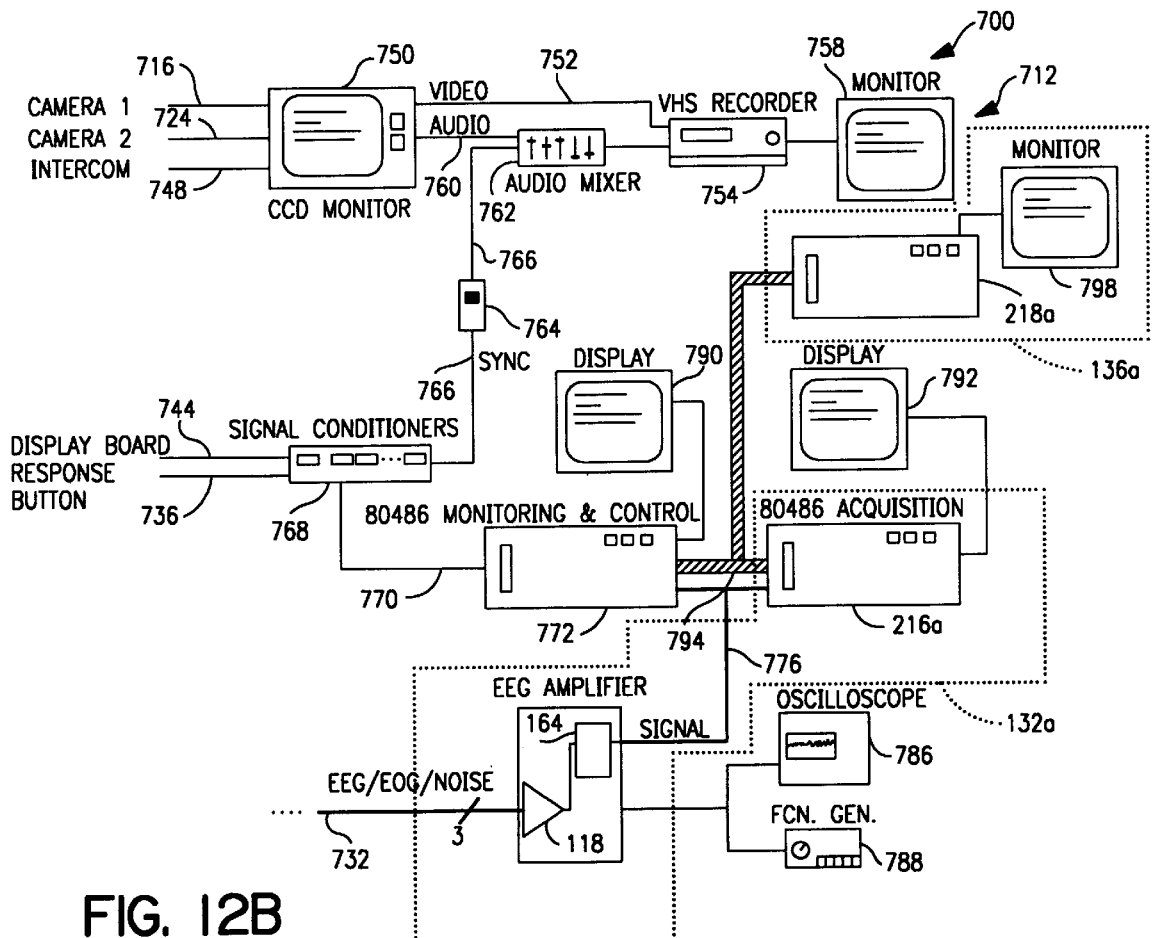
FIG. 12b is a block diagram showing the configuration of the information processing and control portion of a first embodiment of the inventive drowsiness monitoring system shown generally in FIG. 5, the embodiment being adapted for collecting drowsiness-related EEG data in a clinical or research environment.
Figure 13A:
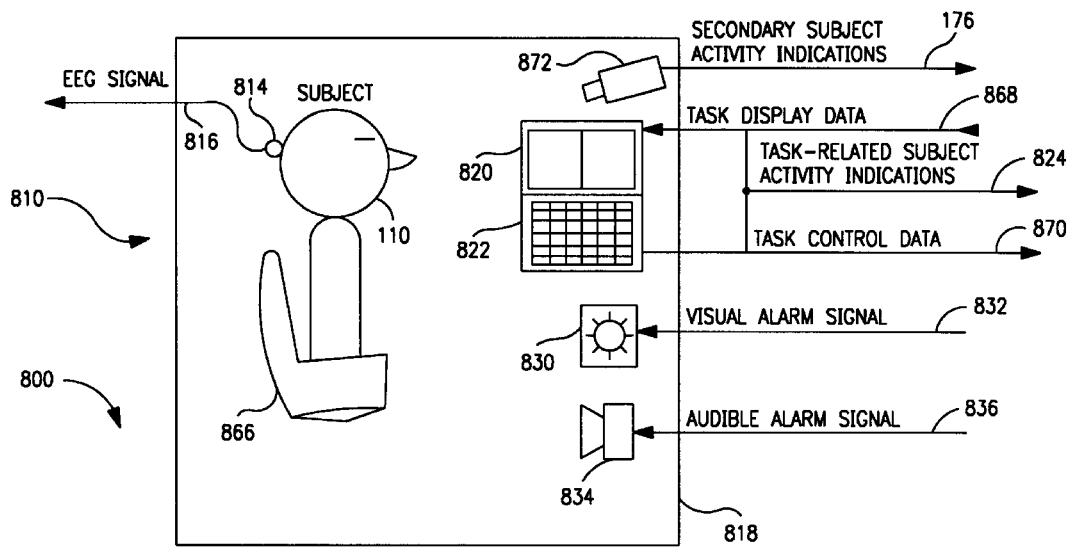
FIG. 13a is a block diagram showing the configuration of the subject interface portion of a second embodiment of the inventive drowsiness monitoring system shown generally in FIG. 5, the embodiment being adapted for collecting drowsiness-related EEG data in a stand-alone or task-based environment.
Figure 13B:
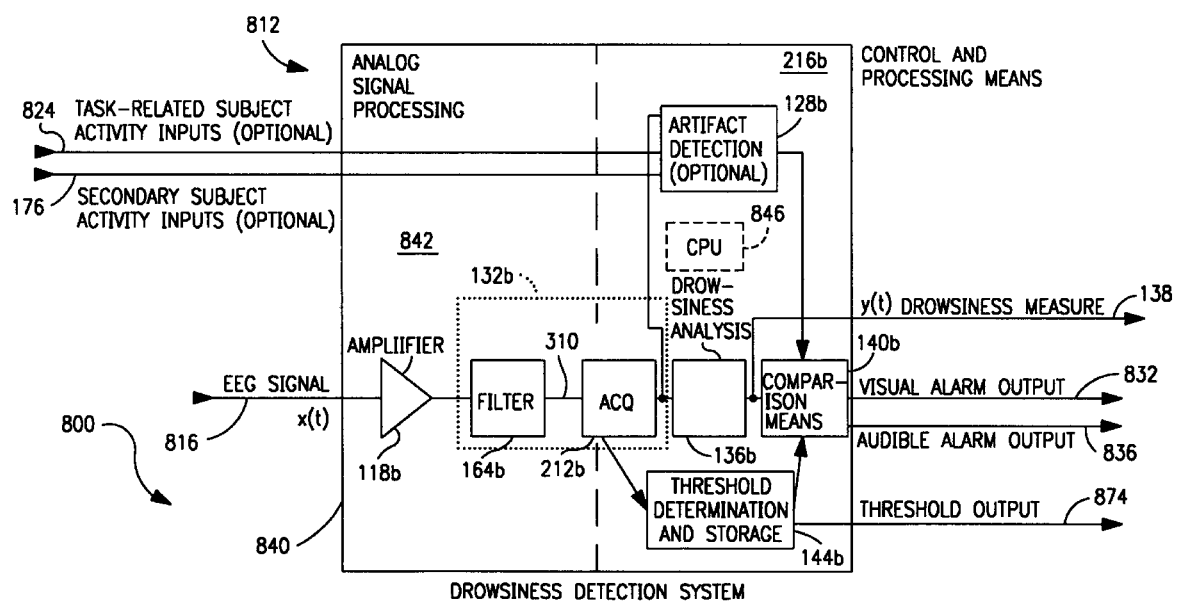
FIG. 13b is a block diagram showing the configuration of the information processing and control portion of a second embodiment of the inventive drowsiness monitoring system shown generally in FIG. 5, the embodiment being adapted for collecting drowsiness-related EEG data in a stand-alone or task-based environment.
Figure 14:
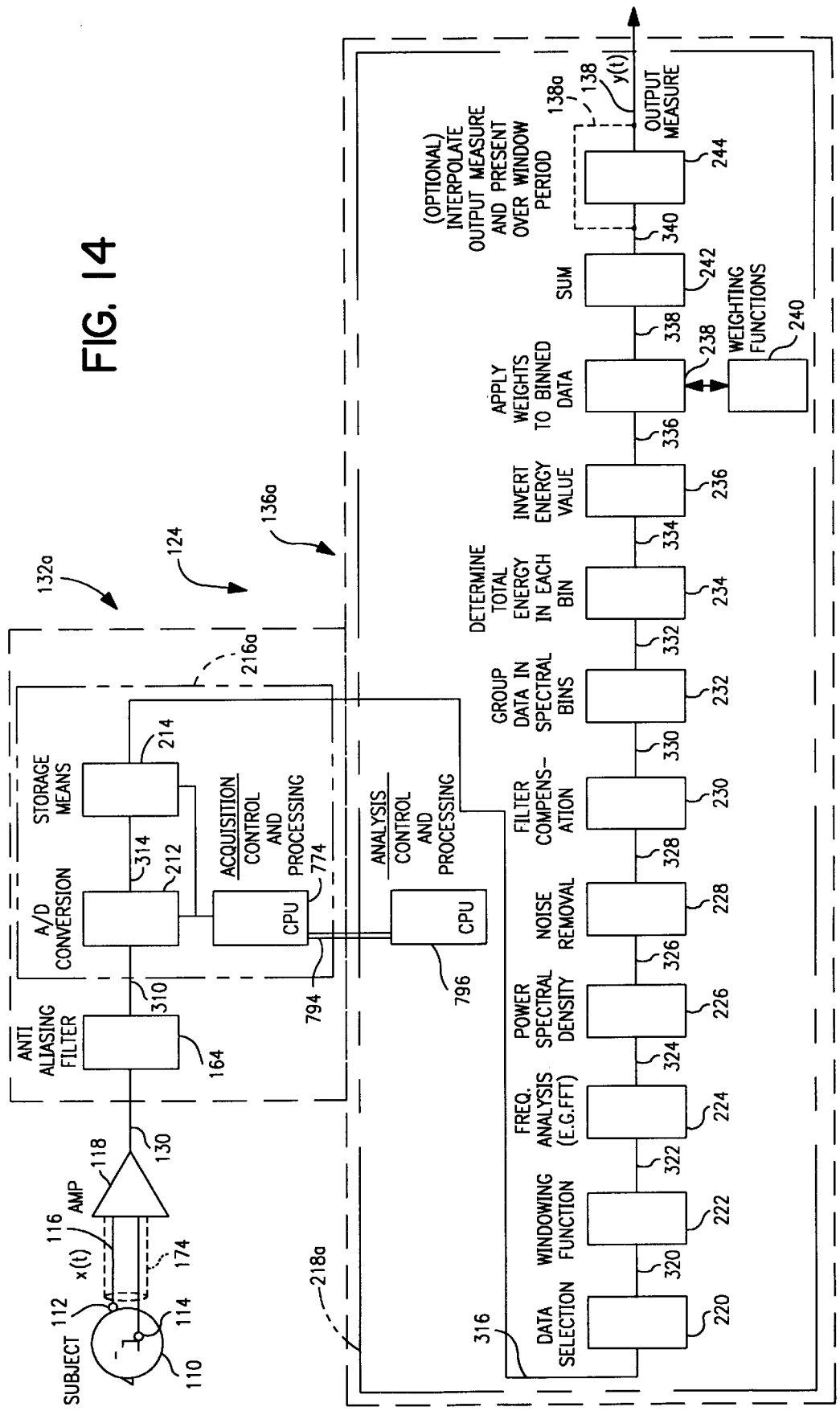
FIG. 14 is a block diagram of a first embodiment of an EEG signal processor component which may be used with the inventive drowsiness detection system of FIG. 5, the signal processor component being arranged to use digital signal processing techniques and in conjunction with the clinical or research environment of FIGS. 12a–12b.

The first embodiment, which is shown in greater detail in FIGS. 12a, 12b, and 14, may be most appropriate for use in a sleep laboratory, clinical sleep analysis, or other medical or laboratory applications, in which it may be desirable to acquire large amounts of EEG data for post-processing and/or on-line analysis which is not necessarily limited to the recognition of alertness, drowsiness or sleep. The second embodiment, which is shown in greater detail in FIGS. 13a, 13b, and 15, may be most appropriate in a stand-alone alertness/drowsiness monitoring and alarm application. For example, the second embodiment might be used as a self-contained, real-time device for on-line monitoring of the alertness/drowsiness of a sonar or radar operator, a nuclear power plant or industrial process control-room operator, or a vehicle operator.

In general, the variations between these two embodiments relate to the scale and structure of the data acquisition and processing components. These variations are the result of differences in the amount of information which may be feasibly collected and the uses to which the raw data and analyzed results are put in the respective application environments. FIG. 16 is a simplified data-flow-type diagram showing the transformation of signal information at various stages, and is common to both embodiments.

The simplified block diagram of FIG. 5 presents a basic platform for realizing an EEG-based drowsiness detection system 100 which is constructed in accordance with an aspect of the present invention. The system 100 of FIG. 5 may primarily employ either digital or analog signal processing and related technologies. FIG. 5 is applicable to all three preferred embodiments. The three embodiments discussed herein differ primarily in their respective application environments, and in the technology used to implement an EEG signal processor component 124. The signal processing components outside block 124, particularly the threshold means and the artifact detection means are optional and may or may not be present in the specific embodiments. Further, according to another aspect of the invention, a drowsiness analysis component 136 could be used independently to analyze EEG signals acquired and stored by other EEG examination systems.

The system 100 comprises suitable means (such as electrodes 112 and 114) for obtaining one or more EEG signals or "channels" 116 from a subject 110, amplifier means 118 for receiving and amplifying the EEG signals, signal analysis means 120 for receiving the amplified EEG signals on lead 130 and producing an output signal 142 indicating that the subject is excessively drowsy (or another suitable result of the analysis), and means 122 for presenting a display or alarm indicating the result of the analysis.

The signal analysis means 120 may be conceptually divided into three main functional components. EEG signal processor means 124 receives analog EEG signals on lead 130 from amplifier means 118, filters and converts the signals into a plurality of digital samples representing the EEG signals, analyzes the digital samples, and responsively produces an output measure 138 indicating the subject's state of alertness, drowsiness, or sleep. An optional artifact detection means 128 receives the digital samples from EEG signal processor means 124, and analyzes the samples, and possibly other information, to determine whether the samples are apparently contaminated by artifacts, and therefore cannot be reliably used. An optional threshold means 126 generates a suitable threshold value (on lead 146) which is compared with the output measure 138 produced by the EEG signal processor means 124. The result of the comparison may be a simplified output signal 142 indicating that the subject has reached or passed a threshold stage of drowsiness or sleep. The threshold means 126 may use as threshold value 146 a universal value believed to be generally applicable to the human population, or may optionally determine the threshold value 146 for an individual using baseline EEG signals acquired therefrom.

The conceptual division of signal processing and analysis means 120 into several functional components is useful in describing its operation, but when implemented, signal analysis means 120 need not have separate corresponding physical components. For example, depending on application requirements, all of the functions of signal analysis means 120 could be implemented using one or more high-performance computer-based systems, or a single-board signal processing system, or even a single-chip digital signal processor.

EEG signals may be obtained from a human subject 110 using any appropriate means, of which several methods are well known in the art. The most commonly used method of obtaining EEG signals is to apply suitable electrodes, such as electrodes 112 and 114 (FIG. 5), at various locations on the subject's scalp in order to detect particular rhythmic EEG signals known to carry desired information.

The "International 10–20 System" of electrode placement has become the standard instrument in research and clinical neurophysiology. The 10–20 System determines electrode locations based on the size of the subject's head and is therefore specific to individuals. Use of the 10–20 System of electrode placement assures accurate and repeatable placement of electrodes for an individual across multiple occasions and examination facilities, and allows the comparison of EEG signals between subjects. The detailed head measurements and electrode application techniques will not be described here, but are disclosed in many handbooks on EEG technology. Some commonly used location names are: frontal (F), central (C), parietal (P), occipital (O), and anterior (A). It is believed that among the standardized scalp locations, the location pairs $O_2$–$A_1$ and $O_1$–$A_2$ are good for use in detecting drowsiness.

Typical EEG electrode connections in clinical applications may have an impedance in the range of 5–10 K ohms. It is generally desirable to minimize the impedance of the connections between the electrode and the subject. Laboratory-grade electrodes may be used to form connections with impedances below 2 K ohms. A conductive paste or gel may be applied to the electrode to further improve the conductivity and mechanical stability of the connection. Commercially available "active electrodes," which provide an amplifier on or near the electrode, may also be used. Needle electrodes may be applied subcutaneously in laboratory applications.

In some other applications, the mechanical configuration or stability of the electrodes, or the ease of applying the electrodes to the subject, or the compatibility of the electrodes with the subject's mobility, are high priorities. Capacitively coupled electrodes may also be used. Additionally, a lightweight EEG sensor could be advantageously provided in a suitable headset (not shown) having a sufficient number of electrodes.

Because the electrical currents of the EEG signals produce associated magnetic fields, methods have been proposed for sensing these magnetic fields to acquire signals equivalent to conventional EEG measurements without electrical contact with the subject. Such signals are referred to as magnetoencephalogram (MEG) signals. One of ordinary skill in the art will appreciate that the present invention could be used with MEG signals with little or no modification.

To maximize clarity, the block diagram of FIG. 5 depicts collection and processing of a single EEG channel. However, one skilled in the art will appreciate that an inventive drowsiness detection system could advantageously collect and process multiple EEG channels. If desired, collection and processing of multiple EEG channels may be accomplished by simply replicating all of the components shown on a per-channel basis. Alternatively, one could use multiplexing, computer multi-tasking, and other techniques which are known in the art for processing multiple signals with a smaller number of processing means and signal paths.

The number of EEG signals to be processed depends on the environment in which the drowsiness monitoring system is to be used. In laboratory or clinical environments, it may be desirable and relatively convenient to collect and process EEG signals obtained at several locations on the subject's scalp. Skilled technicians are available to apply the electrodes, and portability of the signal acquisition and analysis equipment is not a high priority. In stand-alone environments, where a subject is to be monitored while performing a real-world task, technicians may not be available to apply the electrodes, and subject mobility requirements may limit the size and weight of the signal acquisition and analysis equipment. In such environments, it may be feasible to collect and process only a few channels, or only a single channel, of EEG data. When processed and analyzed according to the present invention, a single channel of EEG data is sufficient to reliably track or detect the onset of extreme drowsiness in a human subject.

The number of electrodes required depends on the number of EEG signals to be processed. At least two electrodes (one signal electrode, such as electrode 112 (FIG. 5), and one reference electrode, such as electrode 114) are required to obtain one EEG channel. The number of electrodes needed to obtain greater numbers of EEG signal channels depends on whether separate reference electrodes or a single reference electrode is used.

As noted previously, the EEG signals as measured are very low voltage signals (in the microvolt range). In order to provide sufficient voltage levels for further processing, the EEG signals must be amplified. Any suitable cables or wires 116 may be used to connect the electrodes 112 and 114 to an appropriate EEG amplifier means 118. Care should be taken to minimize interference from electrical noise sources. For example, cable 116 may include a shield conductor 174.

EEG amplifier means 118 may be implemented using a suitable high-quality amplifier having a high input impedance and sufficient gain to amplify the EEG signals for input to the signal analysis means 120. As will be discussed further, the signal analysis means 120 is nominally configured to receive an output signal on lead 130 in the ±2.5 volt range from amplifier means 118. However, another appropriate voltage range could be selected for the amplified signal, provided that both the output of amplifier means 118 and the input of the signal analysis means 120 are compatible. High linearity, low distortion, flat frequency response, and good common-mode rejection are desirable characteristics for amplifier means 118. EEG signal levels available at the input of amplifier means 118 may vary, depending on the subject, the type of electrode (or other probe device) used, and the quality of the connections obtained. Preferably, amplifier means 118 provides several operator-selectable gain settings to accommodate such variations. Because the amplifier means 118 will be electrically connected to a person, amplifier means 118 must be designed and constructed consistent with applicable safety standards for such equipment.

Several commercially available amplifiers, which have been specifically developed for use in collecting EEG signals and meet these requirements, could be used. One such amplifier popular in clinical EEG applications is a component of a commercially available product sold under the name "Grass Instruments Model 12C Neurodata Acquisition System." In stand-alone applications where low cost and subject mobility are high priorities, commercially available operational amplifiers ("op-amps") in single-chip or module form might be used in this application. One skilled in the art would appreciate how to select a suitable op-amp (and support components), or other suitable means, such as a portable EEG system, for use in this application.

As best seen in FIG. 5, an amplified EEG signal is provided on lead 130 to an EEG signal processor means 124 which is a component of the signal analysis means 120. The signal on lead 130 is an "analog" signal. The first and second preferred embodiments of this invention, are preferably implemented using digital signal processing and related technologies. Accordingly, in those embodiments, the analog EEG signal must first be digitized-that is, converted into a series of digital samples which represent the original EEG signal with sufficient accuracy. EEG signal processor means 124 comprises an EEG signal acquisition means 132 (including a filter 164 and an analog-to-digital (A/D) converter 212) and a drowsiness analysis means 136. The filter 164 filters the EEG signal, and the converter 212 samples and converts the EEG signal into digital form, and may store the converted samples. The drowsiness analysis means 136 analyzes the samples and produces therefrom an output signal on lead 138 which serves as a "measure" of a subject's state of alertness, drowsiness, or sleep.

Prior-art attempts at automated drowsiness detection using EEG signals have systematically discarded or ignored EEG signal components at frequencies greater than approximately 30 Hz, a factor which we believe has been a significant contributor to the failure of such systems. According to one aspect of the present invention, reliable and accurate information concerning a subject's state of alertness, drowsiness, or sleep is extracted from EEG signal components in frequency ranges well above those considered relevant by traditional EEG doctrine. Prior-art EEG recording systems have filtered out these frequencies as "noise." According to this invention, these frequencies are preserved and analyzed.

We have determined experimentally that particularly useful information resides in the frequency range of approximately 80–475 Hz. Accordingly, the frequency range of 80–475 Hz is discussed herein merely as an example of frequencies above 30 Hz which are of interest in the analysis of EEG signals for information concerning a subject's state of alertness, drowsiness, or sleep. Drowsiness detection systems which use this exemplary frequency range may be constructed consistent with the preferred embodiments of the invention disclosed herein, and would provide significantly improved performance over prior-art systems. However, it is believed that at least some of the advantages of the present invention may be obtained using any reasonably selected subranges of frequencies between approximately 30 Hz and 500 Hz. In addition, frequencies above 30 Hz which are outside the exemplary frequency range of 80–475 Hz may also be found useful upon further study, and if used might enable drowsiness detection systems to provide satisfactory or improved performance. Therefore, embodiments of the invention may be designed to acquire and analyze an expanded range of frequencies, even above 475 Hz.

In order to analyze such high frequency information, the EEG signal must be sampled at a sufficiently high rate during digitization, and a properly designed anti-aliasing filter must be used to condition the signal prior to sampling. It is known that a band-limited signal can be uniquely represented by a plurality of regularly spaced samples if the rate $f_s$ at which samples are taken is at least twice the highest frequency $f_{max}$ in the original sample. For example, in order to sample a signal containing components at frequencies up to an exemplary maximum frequency $f_{max}$ of 475 Hz, the minimum sampling rate $f_s$ would be 950 samples per second (SPS), but any sampling rate greater than 950 SPS could be used. In a prototype embodiment of the invention, a sampling rate $f_s$ of 950 Hz was used to collect data (discussed below in detail) concerning the performance of the invention in detecting drowsiness. Although the sampling rate may be increased to the limits of available technology, faster sampling increases the cost of equipment and the amount of signal data which must be processed. Inexpensive commercially available equipment could be advantageously employed in preferred embodiments of the invention to allow exploitation of EEG signal information at higher frequencies.

Figure 1:
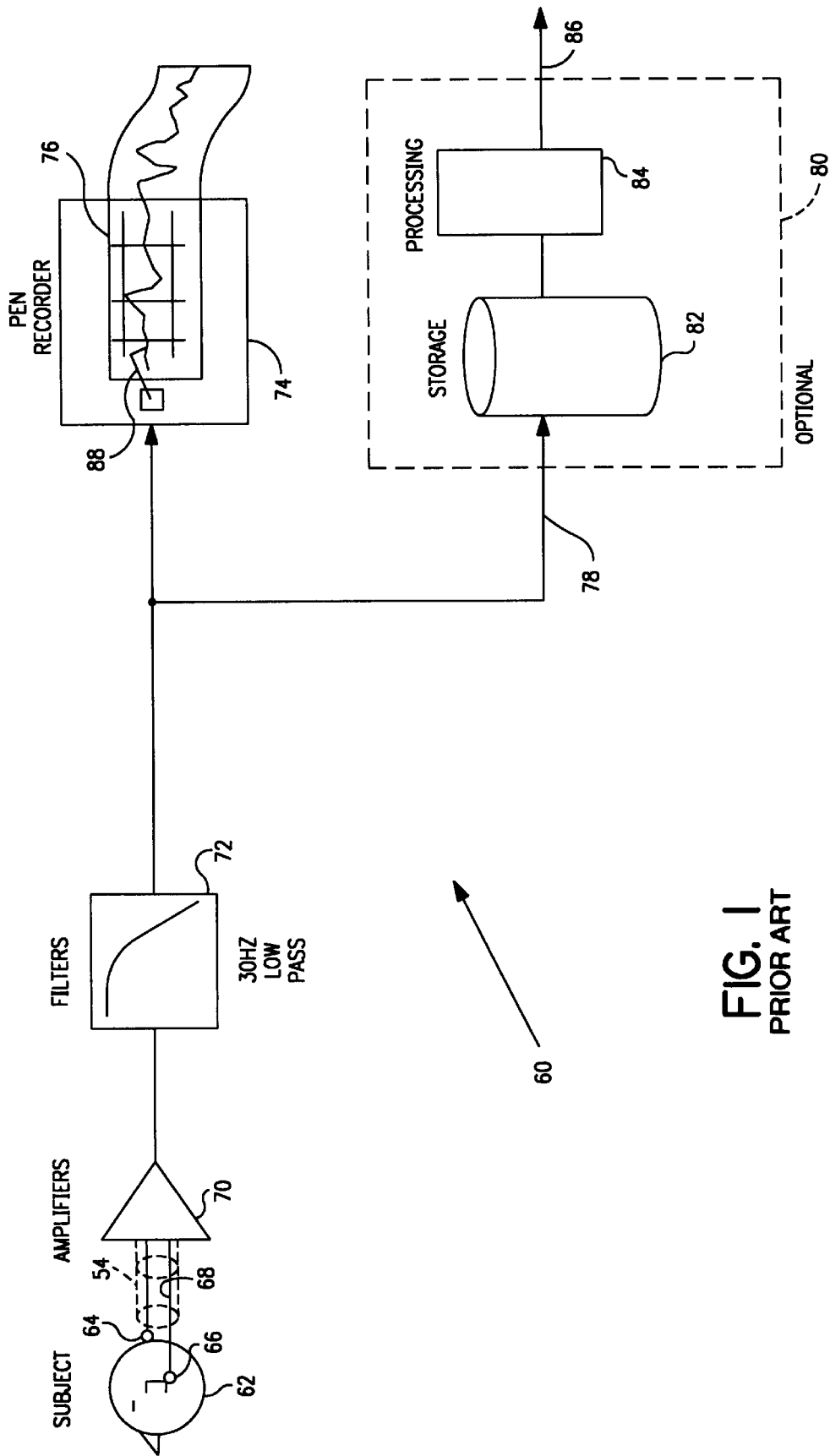
FIG. 1 is a block diagram of an EEG recording system typical of those used according to the prior art.
Figure 2:
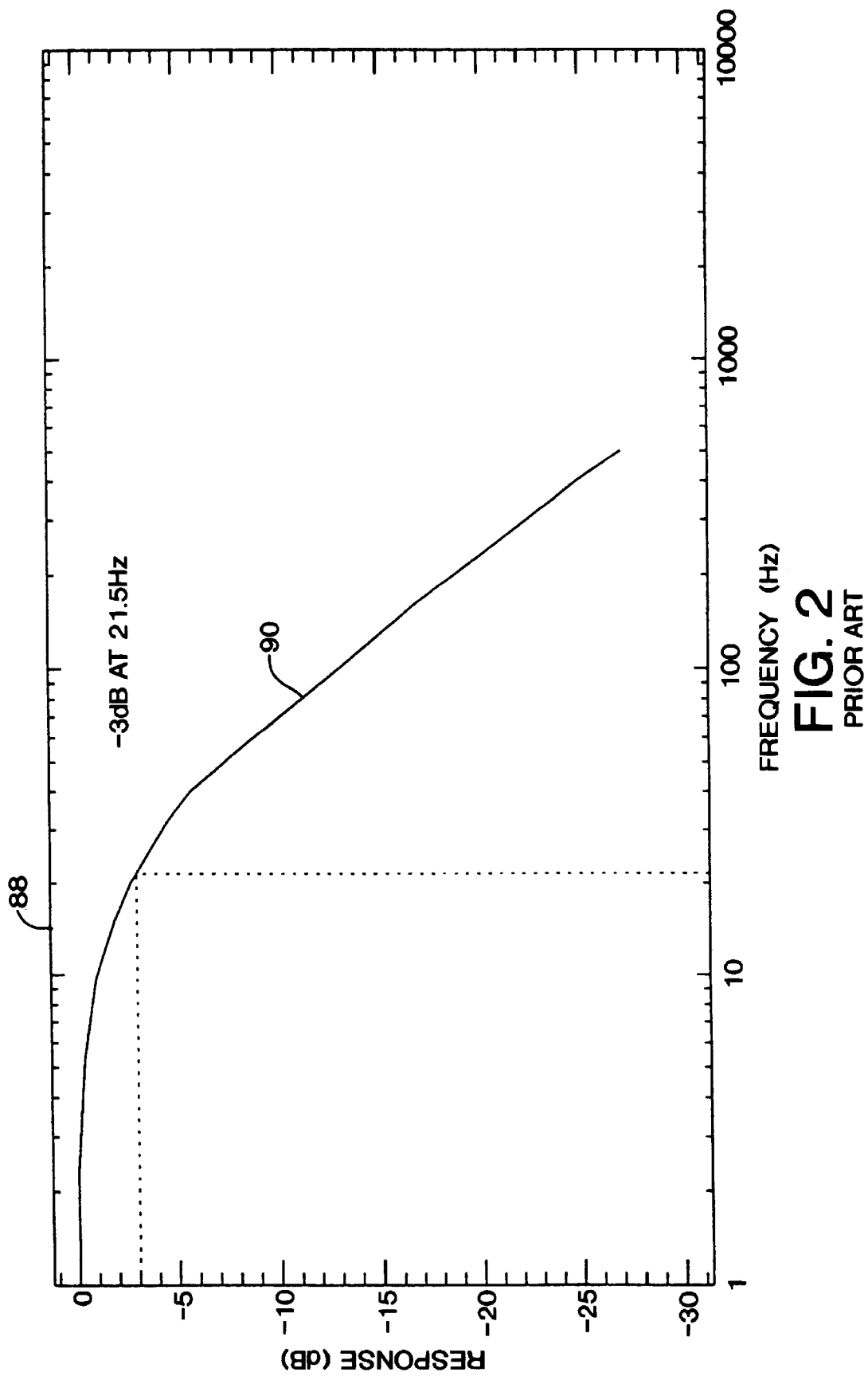
FIG. 2 is a graph showing the frequency response of a low-pass filter used in the prior-art EEG recording system of FIG. 1.

Drowsiness monitoring system 100 preferably comprises suitable anti-aliasing low-pass filter means 164 for attenuating signal components above the maximum frequencies desired for drowsiness detection, thereby providing a band-limited signal for digitization. Filter means 164 is shown in FIG. 5 as an integral part of EEG signal acquisition means 132, but it may be located elsewhere provided that it operates on the EEG signal before sampling, and could be, for example, integrated with the EEG signal amplifier 118. It is conventional to employ a low pass filter 70 (FIG. 1) in an EEG recording system, and a variety of such filters are commercially available. However, the commercially available filters designed for conventional EEG recording applications are not preferred for anti-aliasing because they employ a low-order design (such as first-order Butterworth) resulting in a shallow filter roll-off (see FIG. 2).

If the previously mentioned exemplary frequency band of 80–475 Hz were selected for use with the first and second preferred embodiments discussed herein, a minimum sampling rate $f_s$ of 950 Hz could be used. A low-pass (anti-aliasing) filter providing 50 dB of attenuation in the stop band would be sufficient. A sixth order Butterworth filter having a −3 dB point selected at 182.1 Hz provides at least 50 dB of attenuation at 475 Hz and above and can be affordably implemented with commercially available components. This type of filter has a more rapid transition from the pass band to the stop band than the shallower first-order response of filters typically implemented in EEG equipment.

Figure 6A:
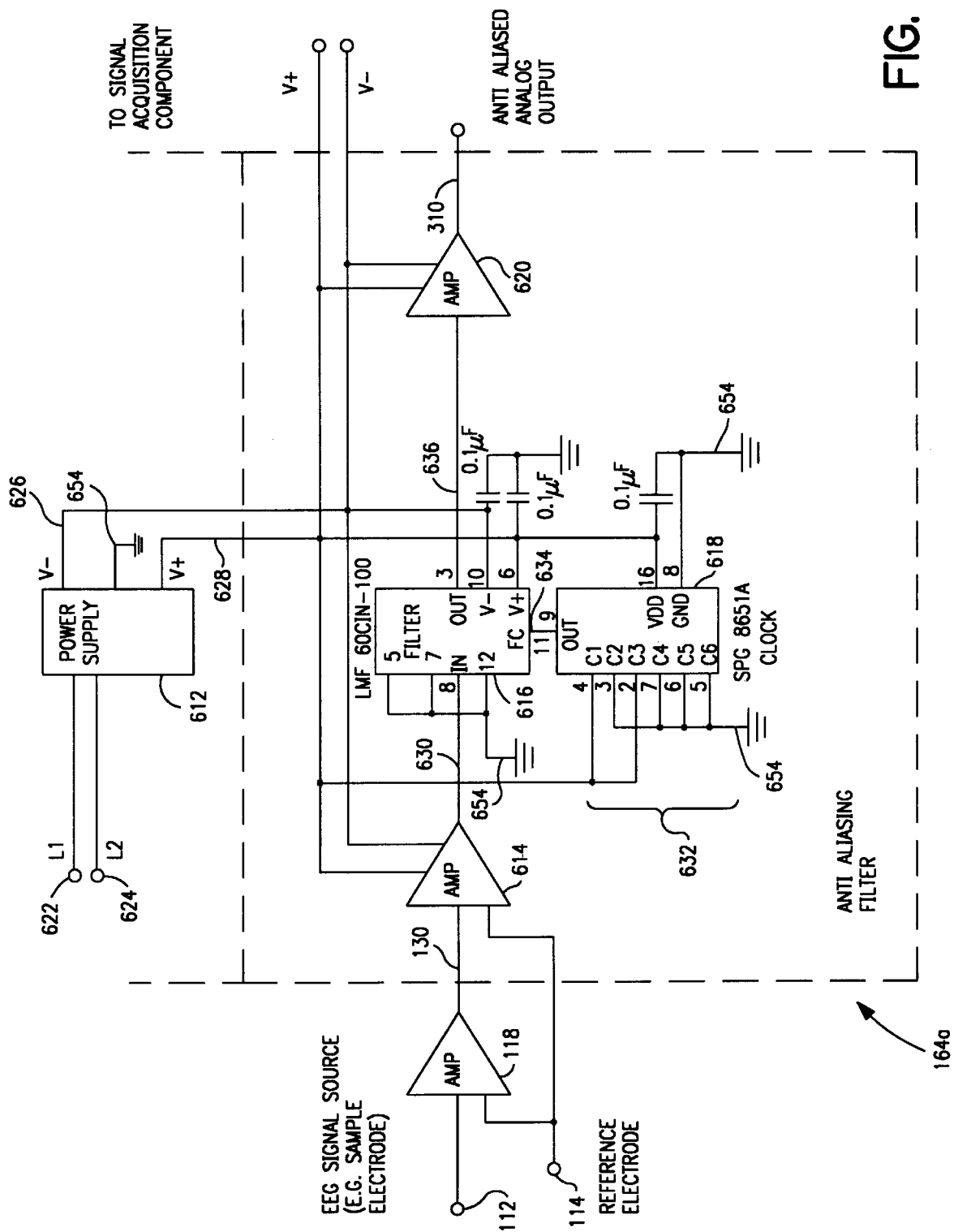
FIG. 6a is a simplified schematic diagram showing a low-pass filter which may be used for anti-aliasing in the inventive EEG-based drowsiness monitoring system of FIG. 5.
Figure 6B:
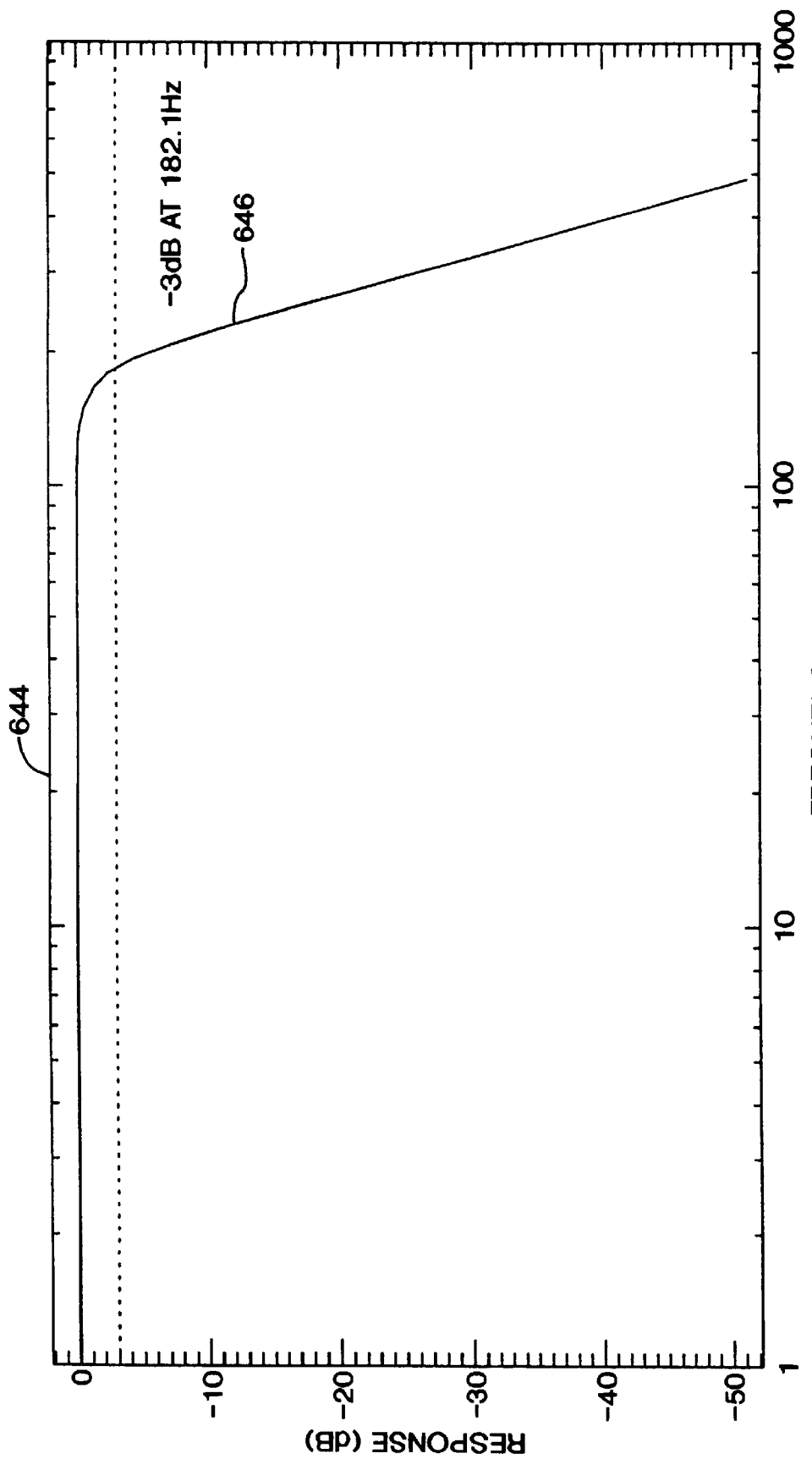
FIG. 6b is a graph showing the frequency response of the low-pass filter of FIG. 6a, for use in the inventive EEG-based alertness monitoring system of FIG. 5.

FIG. 6a is a schematic diagram of a low-pass anti-aliasing filter means 164a which has these characteristics and which is suitable for use in conjunction with the drowsiness monitoring system 100 (FIGS. 5, 14, 15) of the present invention. FIG. 6b is a graph 644 showing the frequency response 646 of the low-pass filter of FIG. 6a. As best seen in FIG. 6b, the attenuation of the filter 164a begins within the frequency band of interest. However, subsequent processing may be used to compensate for this attenuation (see filter compensation means 230, FIGS. 14 and 15), or a higher sampling rate could be used to allow the filter's −3 dB point to be moved beyond 182.1 Hz, thereby extending the pass band of the filter.

As best seen in FIG. 6a, anti-aliasing filter means 164a comprises a suitable power supply 612 (which may be shared with other signal acquisition equipment), an optional input buffer amplifier 614, an optional output buffer amplifier 620, a filter module or circuit 616, and an oscillator module 618 for determining the cut-off frequency of the filter module 616. Power supply 612 may be any suitable regulated DC power supply providing at least a first output "V–" 626 at approximately –5 volts, and a second output "V+"628 at approximately +5 volts, referenced to a common ground 654. Power supply 612 is preferably of the "linear" type which generally provides reduced noise at the power supply outputs (compared to "switching" power supplies).

A suitable power supply 612 is commercially available from Power-One, Inc., 740 Colte Piano, Camarillo, Calif. 93012, under the designation "International Series, Model HCC5–6/OVP-A," but other power supplies could also be used. The power supply outputs 626, 628, and ground reference 654 may be supplied to other data acquisition components, such as analog-to-digital conversion means 212 (see FIGS. 14 and 15) to allow the analog-to-digital conversion means 212 access to a low-noise source of power without providing an additional power supply. The power supply 612 may receive power from any suitable source, such as leads 622 and 624 connected to a domestic AC power source. In a vehicular application, a suitable DC-DC power supply could be used, and leads 622 and 624 could be connected to the vehicle electrical system. In an application where portability is desired, power supply 612 could be replaced with a suitable battery.

Any suitable high-performance low-pass filter circuit 616 providing sufficient attenuation could be used to implement the filtering function of filter means 164a. In a preferred embodiment of the invention, a sixth-order Butterworth-type switched capacitor low-pass filter may be used as the filter circuit 616. Such a filter is commercially available, packaged in a single integrated circuit (IC), from National Semiconductor Corporation, Santa Clara, Calif. under the designation "LMF60CIN-100." However, other filter circuits could also be used.

The LMF60 switched capacitor filter circuit advantageously provides a high-performance filter and requires few external components. The filter circuit 616 uses an externally derived clock signal supplied on lead 634 to determine its cut-off frequency. The cut-off frequency is obtained by dividing the clock signal by 100. The LMF60's sixth-order Butterworth design provides a minimum stop-band attenuation rate of approximately 36 dB per octave. In an embodiment which employs a sampling rate $f_s$ of 950 Hz, the resulting sampling system upper limit frequency $f_s/2$ is 475 Hz. A cut-off frequency of 200 Hz is suitable for use with this filter to provide at least 50 dB attenuation at 475 Hz. Accordingly, a 20 KHz filter clock signal may be provided on lead 634 to select a 200 Hz cut-off. One of skill in the art will appreciate that filters having different cut-off frequencies and stop-band attenuation rates could also be used as desired provided that sufficient attenuation is provided at the sampling system upper limit frequency $f_s/2$.

Filter means 164a comprises an appropriate oscillator circuit 618 which provides the clock signal for filter circuit 616. Any suitable 20 KHz oscillator could be used. In a preferred embodiment of the invention, a crystal-controlled oscillator having an integrated externally-programmable divider chain may be used to provide the 20 KHz clock signal. An integrated crystal oscillator and divider circuit 618 which may be used in the filter means 164 of the present invention is commercially available from Epson America, Inc. under the designation "SPG-8651B." As best seen in FIG. 6a, oscillator 618 has a plurality of control inputs 632 by which operation of the internal divider chain may be programmed. In order to produce an output of 20 KHz with the SPG-8651B integrated circuit, control inputs C1 and C3 must be connected to V+ via lead 628, and control inputs C2 and C4–C6 must be connected to ground via lead 654. The output signal from oscillator 618 is supplied to filter 616 on lead 634. The use of a programmable divider advantageously allows a variety of different clock frequencies to be selected as desired for a particular application. Other suitable oscillator/divider circuits which can produce different selections of output frequencies are commercially available.

With reference once again to FIG. 5, the EEG signal from EEG amplifier 118 is provided to filter means 164 on lead 130. The anti-aliased EEG output signal from anti-alias filter means 164, is supplied to signal sampling and conversion means 212 (FIGS. 5, 14, 15) on lead 310. As best seen in FIG. 6a, the EEG signal is preferably buffered by an input buffer amplifier 614. Lead 130 is connected to the input of the input buffer amplifier 614. The output of the buffer amplifier 614 is connected to the input of the filter means via lead 630. The input impedance of the filter circuit 616 may be undesirably low. The input buffer amplifier 614 may be used to present a higher input impedance to the EEG signal supplied on lead 130. Any suitable amplifier could be used for input buffer amplifier 614. The LMF60 filter IC includes two uncommitted operational amplifiers, of which one could be used as a buffer amplifier 614. However, another commercially available operational amplifier could also be used. Alternately, lead 130 may be connected directly to the input of filter circuit 616.

An output buffer amplifier 620 is preferably provided to isolate the filter circuit 616 from the filter means output lead 310. The filter circuit output lead 636 is connected to the input of the output buffer amplifier 620; and the output of amplifier 620 is connected to the filter means output lead 310. Any suitable amplifier could be used for output buffer amplifier 620. The LMF60 filter IC includes two uncommitted operational amplifiers, of which one could be used as an output buffer amplifier 620. However, another commercially available operational amplifier could also be used. Alternately, filter means output lead 310 may be connected directly to the output of the filter circuit 616.

The anti-aliased EEG signal output from filter means 164 is provided to signal sampling and conversion means 212 (FIGS. 5, 14, and 15) on lead 310. Signal sampling and conversion means 212 may be implemented using any suitable analog-to-digital converter system capable of sampling at the desired rate and providing sufficient resolution (or precision). Analog-to-digital conversion at a resolution of 12 bits (i.e. 4096 discrete values) is adequate, but conversion at higher resolution (such as 16 bits) may result in greater overall performance of the drowsiness detection system.

In clinical or laboratory applications, such as the environment in which the first preferred embodiment 700 (see FIGS. 12a, 12b) of the invention may be used, a general purpose computer system may be employed as an acuisition control and processing means 216a (FIG. 12b) for EEG data collection. The computer system is preferably equipped with an interface card or accessory containing one or more analog-to-digital converters and suitable control software to drive the converters and save the converted samples. The EEG signal is converted into digital samples for subsequent analysis using digital signal processing techniques. For example, many small "personal computers" may be used.

A suitable analog-to-digital interface card for use in a general-purpose computer is commercially available from Keithley MetraByte, Inc., 440 Myles Standish Boulevard, Taunton, Mass., 02780, under the designation "DAS1802HR." As noted above, when processed and analyzed according to the present invention, a single channel of EEG data is sufficient to reliably detect the onset of extreme drowsiness in a human subject. In addition, a sampling rate of 950 samples per second appears to be adequate to acquire an exemplary range of frequencies of interest in drowsiness detection. However, it may be advantageous to collect EEG signal data obtained from a plurality of electrode locations, or to collect data at higher rates. The aforementioned interface card is capable of sampling and converting up to 8 fully differential analog channels to digital data at a resolution of 16 bits at an aggregate rate of 100,000 samples per second. If all eight channels are used, the interface card can accommodate a sampling rate of approximately 12,500 samples per second, which allows signals up to 6,250 Hz to be sampled. Other analog-to-digital interface cards could also be used.

In a stand-alone application, such as the environment in which the second preferred embodiment 800 (see FIGS. 13a, 13b) of the invention may be used, it may be a priority to implement a drowsiness detection system 840 in an inexpensive and highly portable package. Signal sampling and conversion means 212 may be implemented using a small general-purpose computer, which may be equipped with an analog-to-digital interface card as described above.

As an alternative, signal sampling and conversion means 212 could be implemented using any appropriate single-board computer which is equipped for signal processing applications, of which several are commercially available. For example, Texas Instruments produces several board-level products for digital signal processing applications which may be used. A suitable single-board computer for use in this application would provide: at least one channel of analog-to-digital conversion capable of a sampling rate of at least 950 samples per second; a digital signal processor or other high-performance microprocessor to control data acquisition; sufficient memory for storing control software and acquired data; and means for presenting the acquired data for analysis.

Another alternative would be to implement signal sampling and conversion means 212 using a single-chip microcomputer having suitable on-chip facilities for analog-to-digital conversion. For example, a single-chip microcomputer commercially available from Motorola, Inc., Austin, Tex. 85284, under the designation "MC68HC11A8" includes an analog-to-digital converter which can sample and convert up to four analog signal inputs at approximately 15,000 samples per second, producing 8-bit results. Although higher resolution A-D conversion results would be desirable, 8 bits of A-D resolution may be adequate for some drowsiness detection applications.

Once EEG signal data is acquired and converted by the signal sampling and conversion means 212 (FIGS. 5, 14, 15), the data is provided to the drowsiness analysis means 136 (FIGS. 5, 14, 15), which analyzes the data and produces therefrom an output signal on lead 138 which serves as a "measure" of a subject's state of alertness, drowsiness, or sleep. The operation of the drowsiness analysis means is described in greater detail in connection with FIGS. 14–16. Any suitable general-purpose computer, or a special-purpose digital signal processing system, may be used to implement the drowsiness analysis means 136. A general purpose computer may be used to control EEG signal acquisition means 132 and to perform all of the other processing functions of signal analysis means 120, including those of the drowsiness analysis means 136, threshold means 126, and artifact detection means 128.

If a general-purpose computer is used, capabilities required of the computer will depend on the sampling rate, the number of EEG signal channels to be analyzed, and whether the results of the analysis are required in an on-line mode. In some applications, such as in clinical diagnostics, it may be appropriate to collect a large batch of EEG data for subsequent analysis. In other applications, and particularly in stand-alone environments in which a drowsiness detection system is used to provide a warning when a subject performing a task becomes unable to perform the task safely, it is essential to analyze the data and produce a real-time result. For a single EEG signal sampled at approximately 1000 samples per second, a medium performance personal computer having an Intel "i486"or equivalent central processor is suitable for implementing the functions of the drowsiness analysis means 136 in real time; lower performance computers, such as a single-chip microcomputer, may also be usable. For a plurality of EEG signals sampled at higher rates (e.g., 4 signals sampled at 12,000 samples per second), a mid-range workstation or high-performance personal computer may be suitable, such as personal computer models having Intel Pentium brand processors.

Figure 20A:
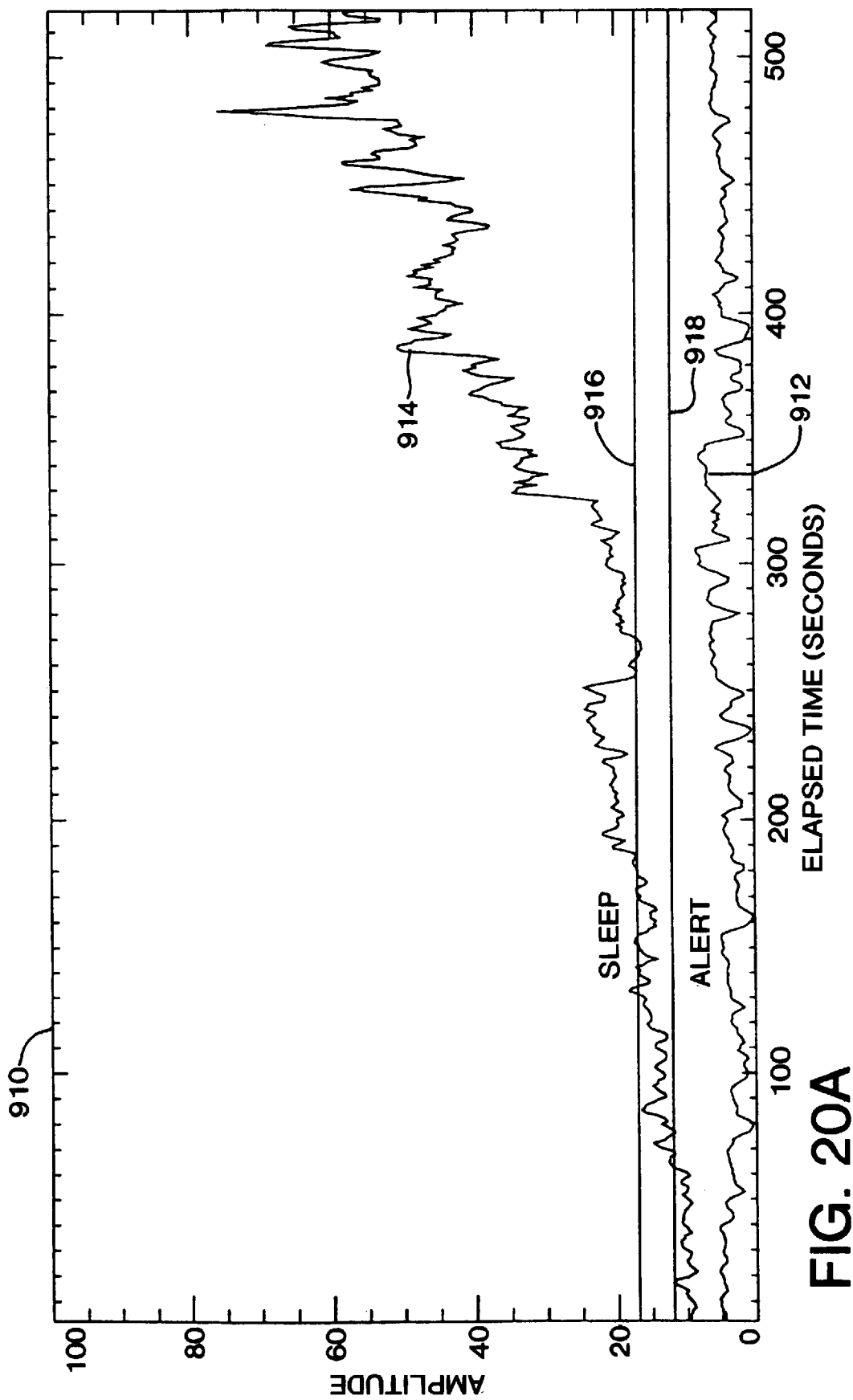
FIG. 20a is a graph depicting the output measure produced by an experimental embodiment of the inventive drowsiness monitoring system during two separate periods of an examination of a human subject, during the first of which the subject was alert and performing a visual test, and during the second of which the subject was in bed going to sleep.
Figure 20B:
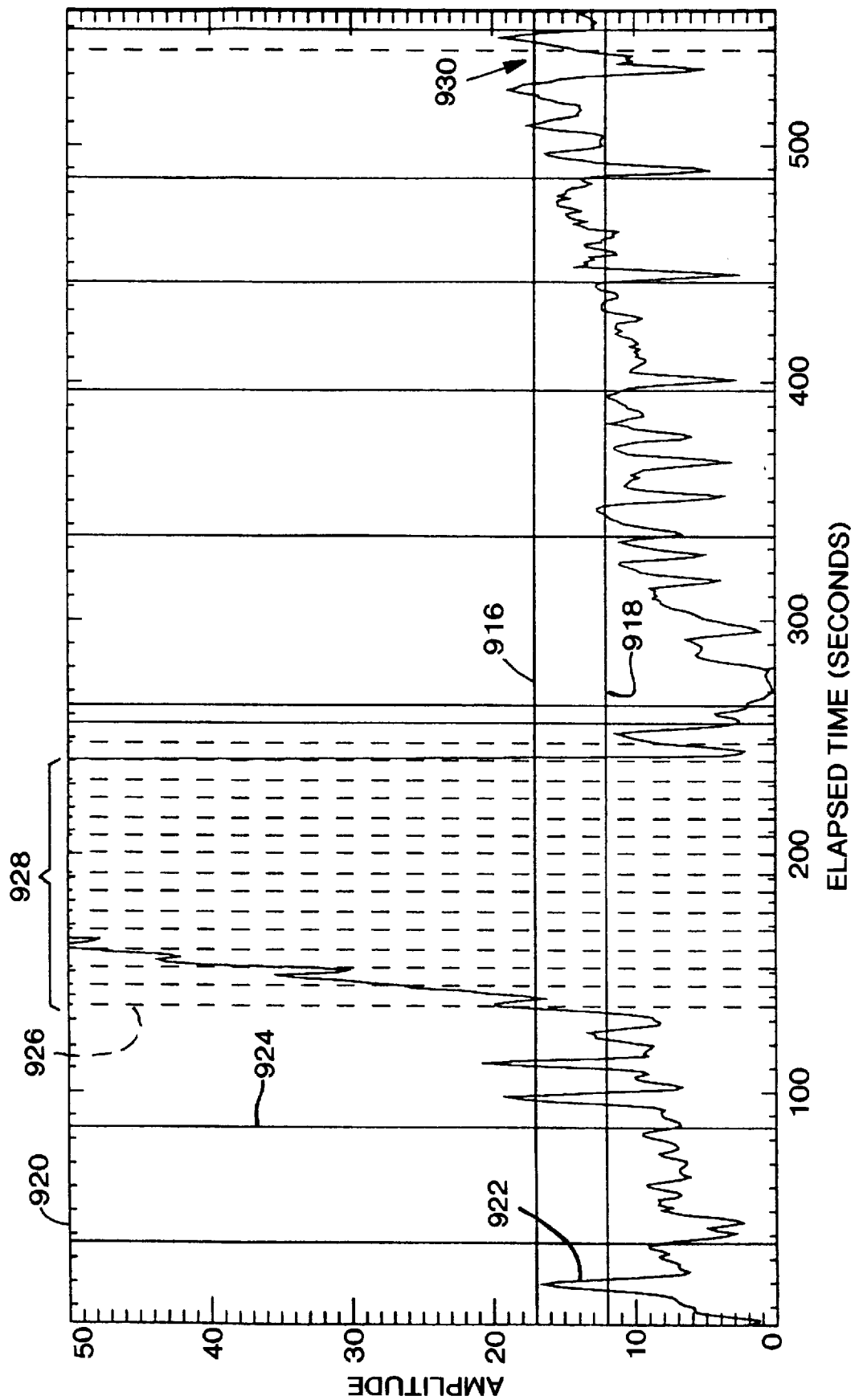
FIGS. 20b and 20c are graphs depicting the output measure produced by an experimental embodiment of the inventive drowsiness monitoring system during an examination of a human subject, in which the output measure accurately predicted the subject's performance failures.
Figure 20C:
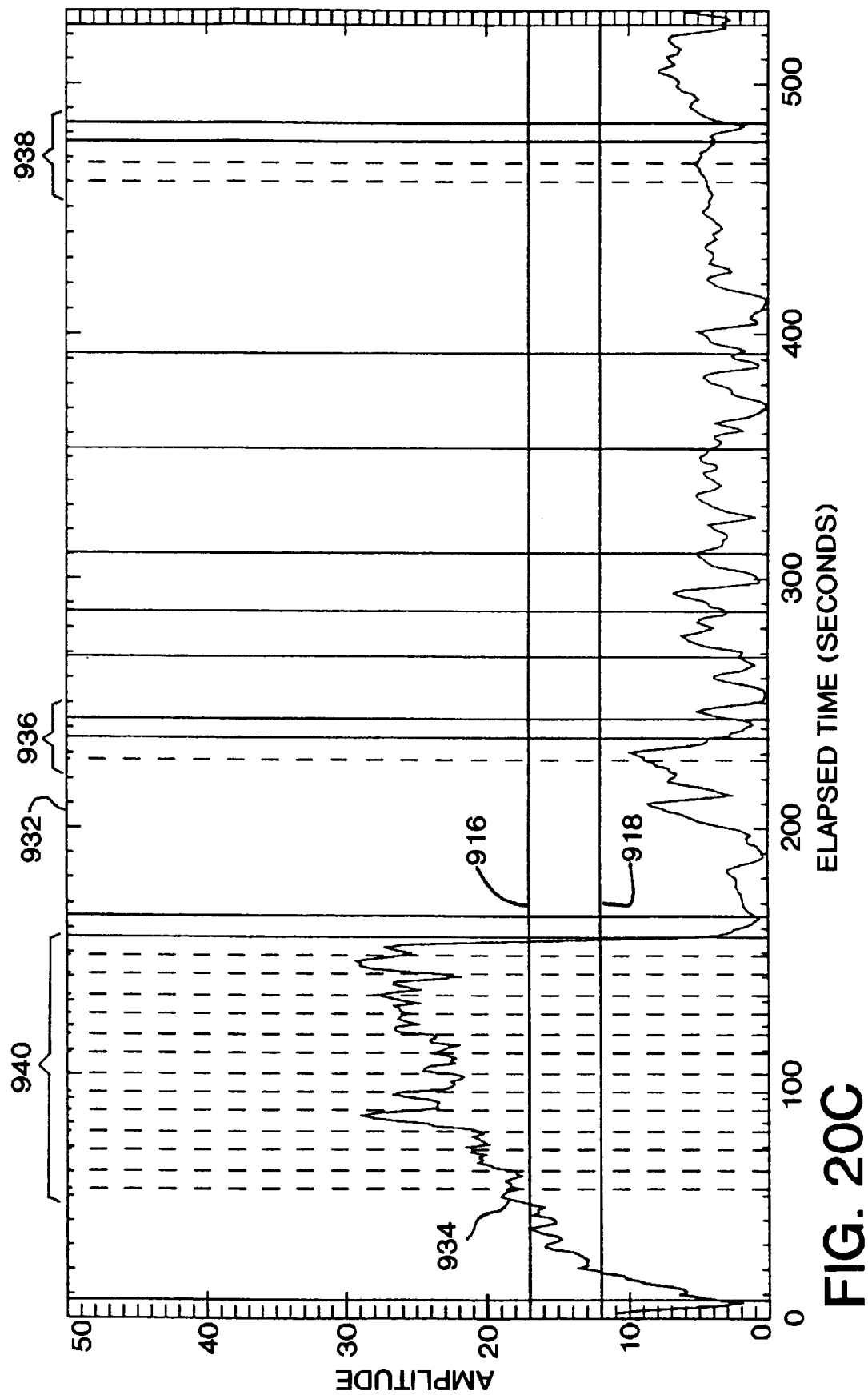

As best seen in FIG. 5, the signal analysis means 120 preferably also comprises a threshold means 126 responsive to the value of an output measure 138 produced by the EEG signal processor means 124 to produce an output signal 142. This output signal 142 would indicate the level of alertness, drowsiness, or sleep of the subject relative to the threshold. As best seen in FIGS. 20a, 20b, and 20c (discussed further in greater detail), the output measure 138 is preferably a continuous quantity representing the instantaneous drowsiness of the subject. An exemplary method of determining the output measure is discussed further in greater detail in connection with FIGS. 14–16, but it may be briefly characterized as a weighted sum of the inverse of the energy of a subject's EEG signal in selected frequency bands.

Figure 19:
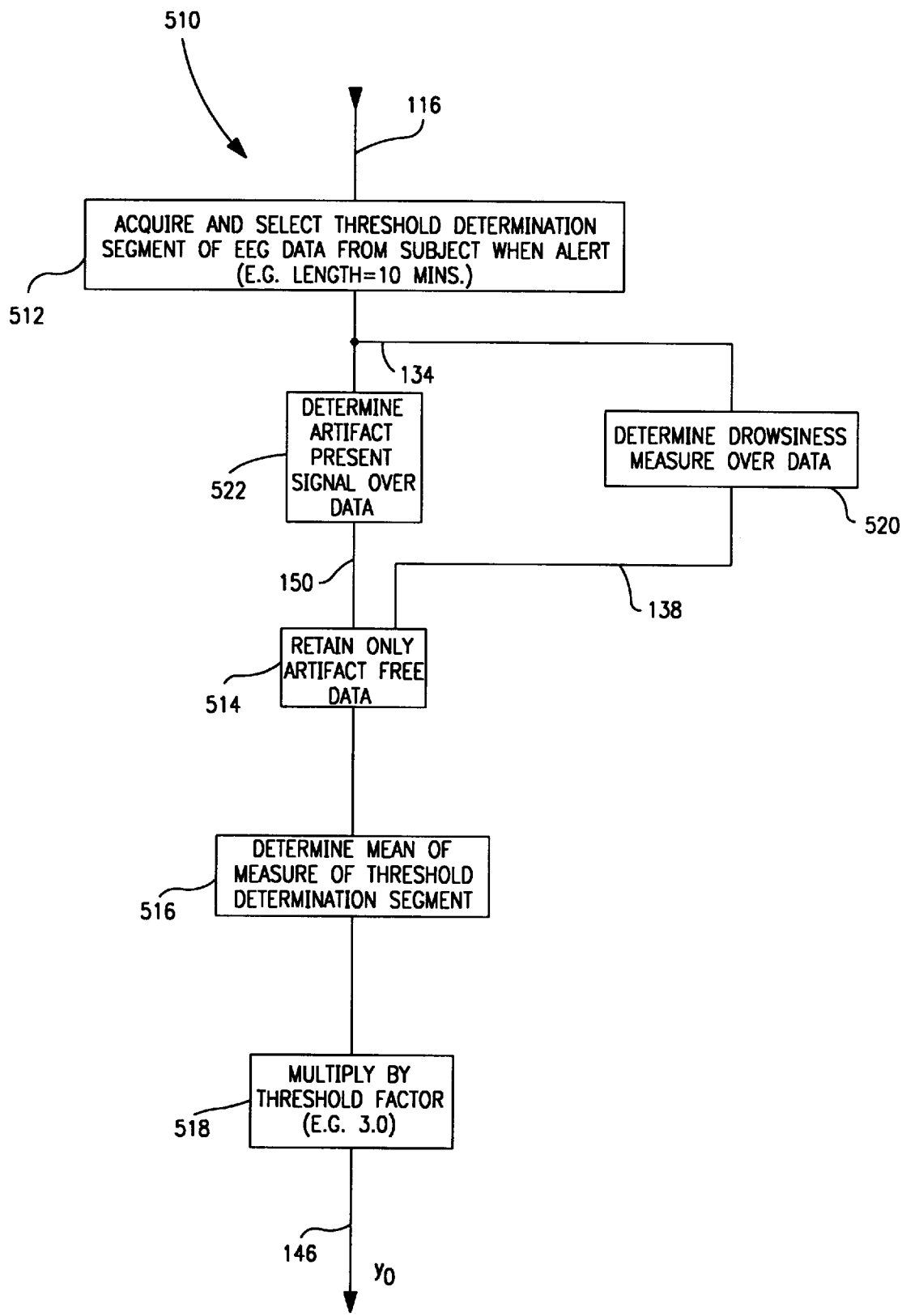
FIG. 19 is a block diagram of a method for use in conjunction with the inventive drowsiness detection system of FIG. 5 for determining a drowsiness threshold against which a drowsiness measure of a subject may be compared to determine when the subject's performance is likely to be impaired.

We have determined experimentally that for any particular subject, the output measure 138 is useful as a relative indicator of drowsiness. The measure increases in magnitude in response to the increased drowsiness of the subject. According to one aspect of the present invention, EEG data may be collected from an alert individual and used to establish a threshold such that values of the measure which exceed the threshold reliably indicate excessive drowsiness in that individual. As best seen in FIG. 5, threshold value generator means 144 preferably receives on lead or data path 134 certain baseline EEG data which was collected by EEG signal acquisition means 132, and provides a drowsiness output measure threshold value or signal on lead 146. A process 510 for use in connection with threshold value generator means 144 for determining a subject's drowsiness threshold from baseline EEG data acquired from the subject is shown in FIG. 19, and is discussed further in greater detail. However, it may not always be desirable or convenient to obtain baseline EEG data from the subject. It is believed that a predetermined universal threshold value, which has been determined experimentally, may be used with most of the population to provide acceptable drowsiness detection results.

Threshold means 126 preferably includes comparison means 140 for comparing the output measure 138 produced by the EEG signal processor means 124 with the threshold value on lead 146 to produce a simplified output signal on lead 142 indicating that the subject has reached or passed a threshold of drowsiness or sleep. Comparison means 140 preferably also receives a signal on lead 150 from artifact detection means 128 indicating that the EEG signal currently being analyzed appears to be contaminated by artifact and one may choose not to use this data in determining the subject's drowsiness.

Any appropriate comparison device or process could be used to implement comparison means 140, depending on the form of the signals or data to be compared and on the desired form of the output. In an embodiment which employs digital signal processing, the values of the output measure, the threshold value, and the artifact detection signal may be stored in locations which are updated from time to time. In that case, the comparison means 140 may be implemented using a software comparison routine. However, in other implementations, the output measure, the threshold signal, and the artifact detection signal, could appear as individual digital signals, or as three separate analog signals, and any suitable comparator hardware, such as magnitude comparators or analog comparators, could be used to implement comparison means 140. The output signal on lead 142 may be used to drive an appropriate display or alarm 122 device to indicate that the subject being monitored by the drowsiness detector is excessively drowsy.

As best seen in FIG. 5, the signal analysis means 120 preferably comprises artifact detection means 128 for determining whether the EEG samples acquired from the subject are apparently contaminated by artifact. Artifact detection means 128 preferably provides an output signal on lead 150 to comparison means 140. In this case, comparison means 140 may responsively inhibit drowsiness indications produced from artifact-contaminated data. This process can effectively ignore or discard the EEG data acquired during intervals when artifact-contaminated data is present.

Figure 18:
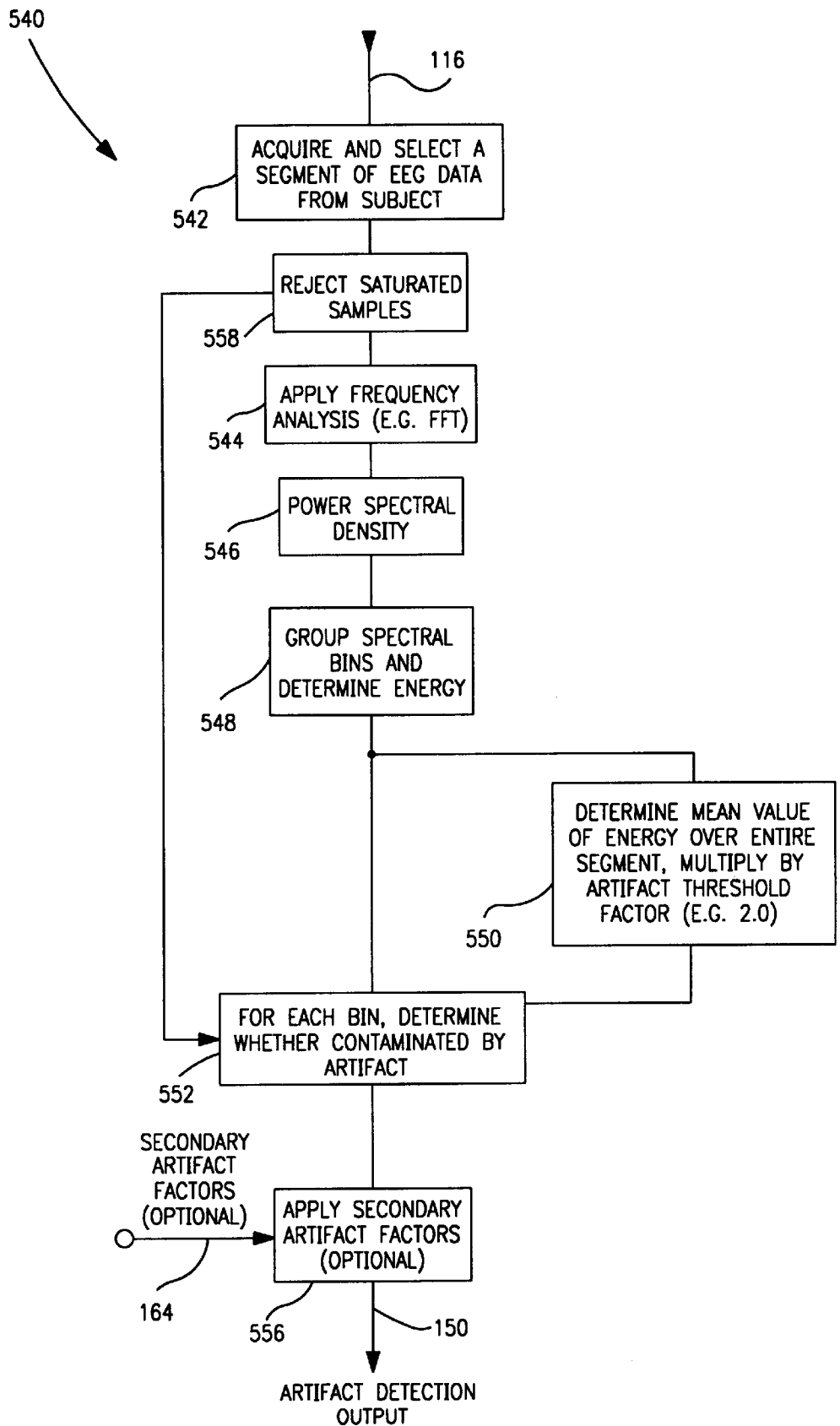
FIG. 18 is a block diagram of a method for use in conjunction with the inventive drowsiness detection system of FIG. 5 for detecting artifacts in EEG signal data collected from a subject.

Artifact detection means 128 preferably comprises means 148 for analyzing EEG data, and optionally, information obtained from non-EEG sources which may indicate that artifact may be present. A process 540 for use in conjunction with artifact analysis means 148 for evaluating whether artifact is likely to be present from the actual EEG data acquired from a subject is shown in FIG. 18, and is discussed further in greater detail. The artifact analysis means 148 may be implemented using any suitable hardware and/or software components. In the first and second preferred embodiments, which employ digital signal processing techniques, and in which sampled EEG data is readily available, the artifact analysis means 148 may be implemented using the same general purpose computer used to implement the drowsiness analysis means 136 and may operate concurrently with the drowsiness analysis components thereof.

However, according to an aspect of the present invention, any artifact-related information which can be conveniently acquired and analyzed may be used to assist in determining that artifact is present in the EEG signals. Thus, artifact detection may also be performed by analyzing signals (shown generally as secondary artifact indicators 824, 176; FIGS. 5, 13a, and 13b) representing external observations of the subject's movement or behavior, such as signals produced by an external motion detector.

In some applications, it may be unnecessary to explicitly provide artifact detection means 128, including means for implementing the artifact detection method 540 of FIG. 18. In general, many types of artifact produce a broadband increase in the energy of a subject's EEG signal. In prior-art EEG-based drowsiness or sleep monitoring systems, which rely on increases in low frequency energy as an indication of drowsiness, the presence of artifact may be perceived as an indication of drowsiness, so that artifact tends to produce a false positive alarm. In the present invention, which relies on a change in energy at higher frequencies as an indication of drowsiness, the presence of artifact produces a response opposite that of drowsiness, and therefore, the inventive system provides substantial immunity to many types of artifact.

FIGS. 12a and 12b are block diagrams showing the configuration of a first embodiment 700 of a drowsiness detection system which is constructed according to the present invention and adapted for use in a clinical or research environment, such as a sleep laboratory. The first embodiment 700 is an implementation based on the general structure of the drowsiness detection system 100 shown in FIG. 5, and employs primarily digital signal processing and related techniques. FIG. 12a is a block diagram showing the configuration of a portion 710 of the first embodiment directed to the function of interfacing with a subject to be monitored. FIG. 12b is a block diagram showing the configuration of a portion 712 of the first embodiment directed to acquiring EEG signals and other signals relating to examination of the subject, processing the data, displaying and recording results, and performing certain control tasks. FIGS. 12a and 12b are shown separately because the interface portion 710 and processing portion 712 may be functionally distinct. It may be convenient to locate the processing and analysis equipment in a location sufficiently remote from the subject so that its routine operation does not disturb or distract the subject. However, some components of the subject interface portion 710 and the processing portion 712 could be physically integrated if desired.

As best seen in FIG. 12a, an exemplary application environment for the first embodiment 700 may be a clinical or research laboratory in which a subject's alertness, drowsiness, or sleep stage is being monitored. The application environment shown in FIGS. 12a and 12b is similar to one which was used in the development of the present invention for the detection of the onset of extreme drowsiness. A brief description of the experimental work may aid in understanding the configuration of the first embodiment and how the invention could be advantageously used in a research or clinical setting. The experiments were directed to obtaining EEG signal information from a subject while performing an assigned vigilance task, and subsequently while resting and falling asleep.

Initially, "baseline" EEG signal information was recorded from a wakeful subject over a period of several minutes. Next, a performance test was conducted. The subject was seated in front of a stimulus display and input device. The stimulus display had several diffuse stimuli which appeared temporarily as dimly illuminated portions of an otherwise blank display field. The subject was provided with an input device to respond when the stimuli were observed. A computer was used to present stimuli at random intervals and the subject was instructed to activate the input device when each stimulus appeared. The stimuli were physically spaced on the display field so that a subject monitoring the stimuli would have to visually scan the display field to observe each stimulus. If the subject failed to respond to a stimulus, subsequent stimuli were presented more frequently until the subject successfully responded. Video cameras, EOG data, and other external indicators were used to determine whether a performance failure was due to drowsiness or sleep, or non-sleep-related behavior. Subsequent to the performance testing phase, the subject was allowed to rest on a bed and to fall asleep.

EEG, EOG and other information regarding the subject was recorded throughout the testing, and an experimental embodiment of the present invention was used to determine the output measure indicating the subject's drowsiness. Results of the trials on human subjects using the experimental embodiment are discussed further in connection with FIGS. 7–11. The performance test was intended to simulate a task typical of those in which drowsiness is a particular problem, such as monitoring a sonar or radar screen, or controlling the operation of a process. Such tasks are characterized by limited physical activity and external stimuli, and requires a high level of vigilance and concentration. Successful operation of the experimental embodiment in monitoring the drowsiness of a subject who participated in the aforementioned performance testing is believed to be representative of the performance of the invention in a real-world application.

The interface portion 710 may be located in a suitable room (not shown) which is preferably isolated from spurious noise, lighting, and other subject distractions. A chair 730 is provided for the subject to use while performing the assigned task. A bed 726 is preferably provided for use by the subject when resting or sleeping as part of the test. Appropriate sensors 778, 780, and 782 collect EEG and EOG signals from the subject and transmit them via a group 732 of signal leads to an array of EEG amplifiers 118 (FIG. 12b) (or other suitable amplifiers). Sensors 778, 780, and 782 may be any suitable electrodes, transducers, or other sensors, such as conventional EEG and EOG electrodes. When the subject is using bed 726, sensors 778, 780, and 782 may be connected to the group 732 of signal leads via an alternate connection 728.

A display means 742 facing the subject when in a seated position and an input device 734 are preferably provided for use by the subject during performance testing. The display board 742 and input device 734 are connected to a signal conditioning unit 768 (FIG. 12b) by means of leads 744 and 736, respectively. The signal conditioning unit 768 is connected to a monitoring and control computer 772 using leads 770. The monitoring and control computer 772 is primarily responsible for interacting with the subject in the context of an experiment or test, such as the aforementioned subject performance test. As best seen in FIG. 12b, the examination monitoring and control computer 772 and an acquisition control and processing means 216a may be provided as separate units. However, a single computer could also be used to perform these tasks. Display board 742 may be any suitable display which the subject can observe during a test.

In an experimental embodiment of the invention, the display means 742 was constructed as a planar surface having five spaced indicia 746 which could be illuminated under control of the monitoring and control computer 772. When not illuminated, the indicia 746 were essentially invisible to the subject. The input device 734 may be any device actuatable by the subject in response to an external stimulus including the indicia 746 of display board 742. For example, the input device 734 may be a push-button switch. Other devices could be used to implement the display means 742, indicia 746, and the input device 734. The signal conditioning unit 768 may be any suitable I/O interface for connecting a computer to real-world inputs and outputs. For example, the signal conditioning unit 768 may be implemented using a model CIO-DIO24 digital input/output module coupled using suitable interconnection means to model DCO5-B DC output isolation modules and model DCI5-B DC input isolation modules, all of which are commercially available from Omega Engineering, Inc., P.O. Box 4047, Stamford, Conn., 06907. Other interface equipment could also be used.

In order to observe and record the subject's movements, suitable camera means 714 and 722 may be trained on the chair 730 and the bed 726 respectively. Camera means 714 and 722 may be any suitable cameras providing a recordable output; in a preferred embodiment of the invention, camera means 714 and 722 are CCD video cameras having high sensitivity to visible and infra-red light, and provide a standard NTSC video output on leads 716 and 724, respectively. Leads 716 and 724 are preferably connected to a suitable monitor 750 for viewing by a remote person, such as a nurse or a person supervising the experiment or test. An intercom 740 in the testing room may be connected to the monitor 750 via lead 748 to allow the subject and the remote person to communicate orally.

The monitor 750 preferably includes means to allow an operator to select the camera from which an image is displayed, and provides a video signal corresponding to the signal from selected camera on lead 752 to a recorder 754. Recorder 754 may be any suitable image and sound recording means, such as a conventional VHS-format "video" cassette recorder. The monitor 750 provides a suitable audio output signal on lead 760 to an audio mixer panel 762. The output of the audio mixer panel is provided to recorder 754. A monitor 758, which may be a conventional television receiver or monitor is connected to the recorder to present the recorded video and audio to a user. An infra-red light source 718 supplied with power on lead 720 illuminates the testing room to enable operation of the cameras even when room lighting is subdued or off.

The image information supplied by the cameras 714 and 722 may be useful in the evaluation of the cause of some artifacts in the EEG record, and to determine whether a failure by the subject to respond to a stimulus was due to some cause other than drowsiness or sleep. For example, the subject may be fully alert, but may not be looking at the display board 742. Accordingly, information obtained from the cameras may be supplied to the drowsiness detection system 100 as an optional secondary input to the artifact detection means 148 (see lead 176, FIG. 5). Systems (not shown) which detect motion or change in a video signal are known in the art and could also be used to produce a signal indicating the presence of movement at particular times in the subject's EEG record. Such a signal could be used by artifact detection means 148 (FIG. 5) either alone, or in conjunction with other artifact indicators (such as those derived from the EEG data itself and from EOG signals) for artifact detection as previously discussed.

As best seen in FIG. 12b, EEG and related signals may be provided to an array of EEG amplifiers 118 on signal leads or bus 732. As described previously in connection with FIG. 5, any suitable EEG amplifiers may be used. Suitable anti-aliasing filters 164 are preferably provided for each channel of EEG or related data, and may either be integrated with the EEG amplifiers (as depicted in FIG. 12b), provided as self-contained filters, or provided as a component of the EEG signal acquisition means 132a. A suitable anti-aliasing filter 164a for a single channel has been described previously in connection with FIG. 6a, but other filter designs could also be used. EEG amplifier 118 may be connected to suitable test equipment, such as oscilloscope 786 and signal generator 788 for use by the testing supervisor or other personnel in verifying the operation of the amplifier and in calibration.

Amplified EEG and related signals are provided on signal leads or bus 776 to a monitoring and control computer 772 and a acquisition control and processing means 216a. Each computer preferably cooperates with suitable means for interacting with a testing supervisor, such as displays 790, 792, respectively. The acquisition control and processing means 216a samples EEG signals, converts the sampled signals into representative digital data, and stores the digital signals so that they may be analyzed in real-time or in subsequent processing. An additional computer system 218a may be provided to analyze the digitized EEG signals and present results. Analysis control and processing means 218a preferably also cooperates with suitable means for interacting with a testing supervisor, such as display 798.

Acquisition control and processing means 216a provides the digital data representing the EEG signals to the signal analysis computer 218a on a suitable computer-to-computer interconnection medium 794. The interconnection medium 794 may be implemented using any suitable medium, such as a serial data link or a local area network. If it is desired that the signal analysis computer 218a analyze EEG data in real time, interconnection medium 794 must be capable of relatively high-speed data transfers. For example, a 10 Mbps Ethernet network, or another network providing suitable performance, could be used.

As best seen in FIG. 12b, the first preferred embodiment 700 may comprise separate computers (control and processing means) 772, 216a, and 218a for examination control and monitoring, data acquisition, and signal analysis functions. However, all of these functions could also be implemented using a single computer. In the configuration of FIG. 12b, computer 216a is used to implement the functions of the EEG signal acquisition means 212 of FIG. 5, and computer 218a is used to implement the functions of the drowsiness analysis means 136 of FIG. 5. Computer 218a may also be used to implement the other functions of signal analysis means 120, including those of threshold means 126, and artifact detection means 128. The drowsiness analysis means 136a, is described further in greater detail in connection with FIGS. 14, 15, and 16. In the first preferred embodiment 700, in which several (e.g., 4–8) channels of EEG data may be simultaneously acquired at a sampling rate of 950 samples per second per channel, medium performance personal computers having Intel "i486" or equivalent central processors are suitable for use as computers 772 and 216a, and 218a. However, other computers could also be used, and the minimum performance required of computers 772, 216a, and 218a has not been determined.

The inventive drowsiness detection system may analyze acquired data and produce a result on-line in a "real-time" mode, or may perform these functions off-line. In a clinical or research laboratory environment, it is typically desirable to store a lasting record of the EEG and related signals acquired from a subject for further review and analysis even if analysis is initially performed on-line. If sampled EEG data is to be stored for later review, large amounts of storage may be required in computer 216a. If the data is not compressed, acquisition of 8 channels of EEG data at 950 12-bit samples per second per channel requires approximately 53.4 megabytes of storage per hour. If the sampled EEG data is not stored for later review, only a small amount of data storage is required. As discussed further in greater detail, the drowsiness analysis means 136a operates on successive, overlapping segments of data or "windows" representing the subject's EEG signal during short time intervals. As a minimum, storage must be provided in either the data acquisition means 132a (computer 216a) or in drowsiness analysis means 136a (computer 218a) for at least one complete "current" window of data, plus approximately one half window of new data which may arrive during or after analysis of the "current" window. Additional storage may be required for other functions, such as threshold determination and artifact detection.

A synchronization device 764 is provided to allow correlation of the contents of the video and audio record made by recording means 754 with subject performance test results recorded by computer 772 and EEG data acquired and recorded by computer 216a. Synchronization device 764 may be activated automatically (by monitoring and control computer 772 via signal conditioning unit 768) to supply a synchronization signal on leads 766 to recording means 754 via audio mixer panel 762. A functionally equivalent signal may be supplied to computer 216a. The synchronization signal allows a particular instant in time to be identified in the separately acquired subject performance, video and audio, and EEG records. The synchronization signal may be any suitable signal usable and recording means 754. For example, synchronization signal may be an audio-frequency signal generated by a conventional oscillator or signal generator. Other synchronization signals and methods, such as time stamps derived from a master clock, could also be used.

FIGS. 13a and 13b are block diagrams showing the configuration of a second embodiment 800 of a drowsiness detection system which is constructed according to the present invention and adapted for use in a real-world alertness/drowsiness monitoring and alarm application. For example, the second embodiment might be used to monitor the drowsiness of a person assigned to the operating position of a sonar or radar system, a power or chemical process plant, or a vehicle. In order to be most useful in such environments, the second embodiment 800 is preferably adapted for implementation in a relatively small, portable, configuration 840 which may be assembled into a single enclosure, free of external components except for sensors (e.g. electrodes) for EEG and related signals.

The second embodiment 800 is an implementation based on the general structure of the drowsiness detection system 100 shown in FIG. 5, and employs primarily digital signal processing and related techniques. FIG. 13a is a block diagram showing the configuration of a portion 810 of the second embodiment directed to the function of interfacing with a subject to be monitored. FIG. 13b is a block diagram showing the configuration of a portion 812 of the second embodiment directed to acquiring EEG signals and other signals relating to monitoring of the subject, processing the data, displaying and recording results, and performing certain control tasks. FIGS. 13a and 13b are shown separately because the interface portion 810 and processing portion 812 may be functionally distinct. Preferably, processing portion 812 is integrated in a small equipment package 840 which may be carried on the subject's person or installed in an operator's console or in a vehicle, at a location near the subject. The processing portion 812 may be conceptually divided into an analog signal processing section 842 and a control and processing means 216b which may be conceptually viewed as a digital signal processing section. The conceptual division of processing portion 812 into two functional sections is useful in describing its operation, but when implemented, the processing portion 812 need not have separate corresponding physical components, and could be implemented using a single printed-circuit module or even a single integrated circuit.

As best seen in FIG. 13a, an exemplary application for the second embodiment 800 may be to monitor for drowsiness a subject 110 assigned to the operating position 866 of a sonar system, shown schematically as 818. One of skill in the art would appreciate how the second embodiment 800 could also be used in many other applications with minor or no modification. The sonar system 818 includes a display 820 and operating controls 822 with which the subject is expected to interact. Display 820 is driven by signals on lead 868 from sonar processing equipment (not shown). The operating controls 822 produce signals on lead 870 for use by the sonar processing equipment. A signal on lead 824 may be derived from one or both of the signals on leads 868 and 870 for use as a task-related indication of subject activity, and may be supplied to artifact detection means 128 (FIGS. 13*b* and 5) (discussed further in greater detail). Other means 872, such as a video camera or a motion detector, may be used to provide a secondary subject activity signal to artifact detection means 128 on lead 176.

At least one EEG signal must be collected from the subject. Additional EEG signals, and other physiologically relevant signals, such as EOG signals, may also be collected and used. In the stand-alone environment of the second embodiment 800, because of equipment size, weight, cost, and operator mobility constraints, it may be feasible to collect and process only a few channels, or only a single channel, of EEG data. When processed and analyzed according to the present invention, a single channel of EEG data is sufficient to reliably detect the onset of extreme drowsiness in a human subject. Accordingly, the second embodiment 800 will be described hereafter as acquiring and processing a single EEG signal channel. However, one skilled in the art will appreciate that the second embodiment 800 could be extended to collect and process multiple EEG signal channels, as previously described.

Appropriate sensors 814 collect an EEG signal from the subject and transmit it on leads 816 to a suitable amplifier 118*b*. Sensors 814 may be any suitable electrodes, transducers, or other sensors, such as conventional EEG and EOG electrodes. Amplifier 118*b* provides the amplified EEG signal to a suitable anti-aliasing filter 164. The amplified and filtered EEG signal is then provided to data acquisition, conversion, and storage means 212. Amplifier 118*b* may be implemented using a special purpose, portable EEG amplifier. Alternatively, amplifier 118*b* may be implemented using any suitable operational amplifiers arranged to provide a high input impedance and the desired amplification, which may be in the range of $10^3$–$10^5$. Alternatively, amplifier 118*b* may be implemented using a high-gain amplifier module. A variety of appropriate operational amplifiers and high-gain amplifier modules are commercially available and may be used in the second embodiment 800.

Due to differences among subjects and subject-electrode connections, the amplitude range of the EEG signal acquired from a subject is only predictable to within a range. Because of this variability, in order that the digitized EEG signal data has sufficient resolution for analysis, amplifier 118*b* preferably provides a user-adjustable gain setting. Incorrect gain settings may cause high-amplitude signals to be "clipped" or low-amplitude signals to occupy too small a portion of the analog-to-digital converter data range, resulting in reduced signal quality. Amplifier 118*b* may provide a user-adjustable gain setting which may have a plurality of selectable discrete gain settings or a continuous range of gain settings. However, in the stand-alone environment to which second embodiment 800 is directed, it may be inconvenient to perform such adjustments in the field, as might be required to accommodate multiple subjects at various working times or shifts.

A suitable automatic gain control (AGC) (not shown) may be provided in amplifier 118*b* to ensure that the amplified output signal remains within the dynamic range of down-stream data acquisition, conversion, and storage means 212*b*. The automatic gain control (AGC) preferably provides an output signal indicating the current gain setting which may be recorded with the associated EEG data; when the digitized samples are analyzed, they may be normalized by multiplying them by a corresponding scaling factor so that the numerical value of all samples will have a consistent physical meaning regardless of the amplifier gain used to acquire them.

An alternative to providing an AGC or manual gain adjustment on the amplifier 118*b* is to select a fixed amplifier gain such that the maximum signal amplitude never exceeds the full-scale value of the data acquisition means 212*b* and to provide a greater resolution for the analog-to-digital converter in the data acquisition means 212*b*. If the analog-to-digital converter has sufficient resolution, even signals at the low end of the range of expected signal amplitudes will be represented with sufficient resolution that the drowsiness analysis means can operate effectively. The resolution required in excess of that needed for the analysis means to operate with full-scale signals depends on the difference in amplitudes between the largest and smallest expected EEG signals.

Filter means 164 receives the amplified EEG signal from amplifier 118*b*. Any suitable anti-aliasing filter designed to provide sufficient attenuation and a desired cut-off frequency selected according to the frequency band of interest and the sampling rate of data acquisition, conversion, and storage means 212*b*, may be used to implement filter means 164. The sixth-order Butterworth switched-capacitor filter 164 of FIGS. 6*a* and 6*b* may be a suitable choice.

Data acquisition, conversion, and storage means 212*b* implements the functions of signal sampling and conversion. The data acquisition means 212*b* receives the amplified and filtered EEG signal from filter means 164, and samples the data, converts the data to digital samples, and stores a sufficient quantity of the resulting samples for use by drowsiness analysis means 136*b*. As discussed below in greater detail, the drowsiness analysis means 136*b* operates on successive, overlapping segments of data or "windows" representing the subject's EEG signal during corresponding time intervals. For example, the window time interval might be approximately 2 seconds, and the drowsiness analysis means 136*b* may be configured to determine the output measure approximately once per second, using approximately one second's worth of new data, and one second's worth of "old" data (i.e. overlapping a portion of the data used in the previous determination). The data acquisition means 212*b* must provide sufficient storage for the data required by the drowsiness analysis means 136*b*. For example, if the drowsiness analysis means 136*b* operates on successive overlapping segments of data, then the data acquisition means 852 should provide sufficient storage for at least one complete "current" window, plus approximately one half window of new data which may arrive during or after analysis of the "current" window. Storage may be required for other functions, such as threshold determination and artifact detection, and would certainly be required if a permanent record of the acquired EEG signals is desired.

The EEG signal data acquired by the data acquisition means 212*b* is provided via leads 134 to drowsiness analysis means 136*b*, threshold value generator means 144*b*, and artifact detection means 128*b* on output leads 134, which operate as discussed previously in connection with FIG. 5. Drowsiness analysis means 136*b* will be discussed in greater detail in connection with FIGS. 15 and 16. A process 510 for use in conjunction with threshold value generator means 144b for determining an appropriate drowsiness detection threshold for an individual subject based on EEG signal data acquired from that subject is shown in FIG. 19, and is discussed below in greater detail. A process 540 for use in conjunction with artifact detection means 128b for evaluating whether artifact is likely to be present from the actual EEG data acquired from a subject is shown in FIG. 18, and is discussed below in greater detail.

Drowsiness analysis means provides an output signal on lead 138 which functions as a continuous measure of the subject's state of alertness, drowsiness or sleep. The outputs from drowsiness analysis means 136b, threshold value generator means 144, and artifact detection means 128b are provided to comparison means 140 which compares the output measure with the threshold value 146 to produce a simplified output signal indicating that the subject has reached or passed a threshold stage of drowsiness or sleep. Suitable amplifiers, line drivers, or relays (not shown) may be provided to convert the output signal into a visual alarm output on lead 832 and an audible alarm output on lead 836 for driving a visual alarm 830 and an audible alarm 834 respectively. Alarms 830 and 834 advantageously provide a warning to the subject or to others in the vicinity that the drowsiness detection system 100 has determined that the subject is becoming excessively drowsy before the subject becomes unable to perform their assigned task as intended. The subject or others observing or hearing the alarms can then take appropriate action.

Figure 15:
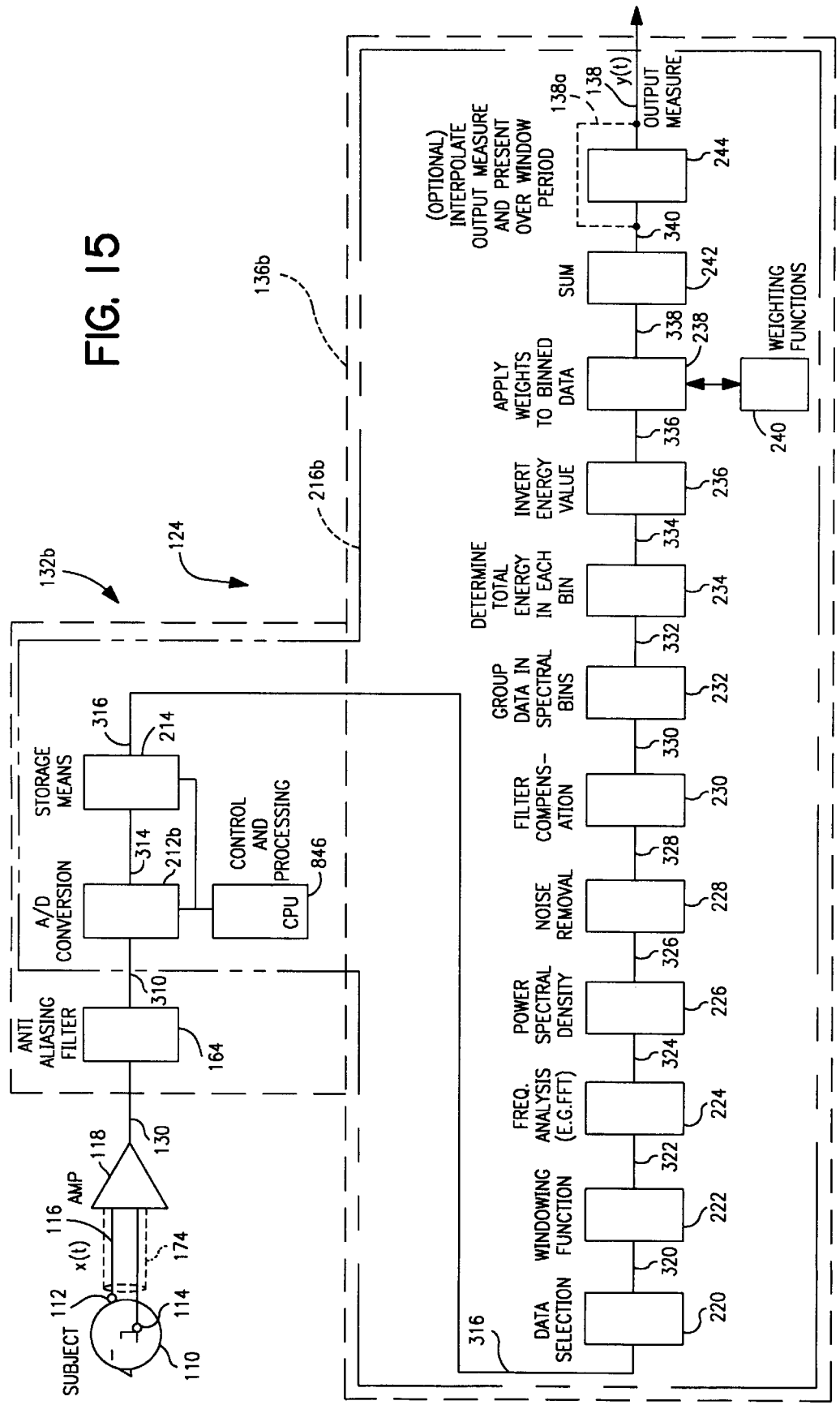
FIG. 15 is a block diagram of a second embodiment of an EEG signal processor component which may be used with the inventive drowsiness detection system of FIG. 5, the signal processor component being arranged to use digital signal processing techniques and in conjunction with the stand-alone or task-based environment of FIGS. 13a–13b.

Any suitable digital signal processing means may be used to implement the functions of the control and processing means 216b (including drowsiness analysis means 136b, threshold value generator means 144b, artifact detection means 128b, and comparison means 140b). For example, as best seen in FIGS. 13b and 15, the control and processing means 216b digital signal processing section may employ a general-purpose central processing unit (CPU) 846 incorporating program and data storage means, input/output means, and associated support components. The CPU 846 may be implemented using a single-board digital signal processing computer, a single-board control computer, or even a high-performance single-chip microcomputer. The central processing unit 846 preferably controls the data acquisition means 212b, which may be incorporated with CPU 846 on the same card or integrated circuit. A single-board control computer having an Intel "i486" or equivalent central processor, and approximately 1 megabyte of storage for program code and data (RAM, ROM, EEPROM, or equivalent), is suitable for use as CPU 846. Such computers are commercially available from numerous sources.

FIG. 14 is a block diagram showing a first embodiment of an EEG signal processor means 124, including EEG signal acquisition means 132a, and drowsiness analysis means 136a, and certain preceding signal acquisition components, configured for use in conjunction with the first embodiment 700 of a drowsiness detection system 100 constructed according to the present invention. FIG. 15 is a block diagram showing a second embodiment of an EEG signal processor means 124, including signal acquisition means 132b and drowsiness analysis means 136b, and certain preceding signal acquisition components, configured for use in conjunction with the second embodiment 800 of a drowsiness detection system 100 constructed according to the present invention. FIG. 16 is a data-flow diagram depicting, in simplified form, the processing of EEG signal information acquired from a subject, as that information is operated upon by the processing means of the embodiments of FIGS. 5 and 14–15. Interconnections between the components of EEG signal processor means 124 are designated herein as signal leads, or in the case of digital data, "data paths." For each such signal lead or data path in FIGS. 14–15, there is a corresponding signal or data element shown in FIG. 16. The elements of FIG. 16 represent the form of the signal or data being transferred over the corresponding signal lead or data path.

The principal difference between the two embodiments of EEG signal processor means 124 shown in FIGS. 14 and 15 is that in the embodiment of FIG. 14, separate control and processing means 216a, 218a are provided for the data acquisition and analysis, respectively, while in the embodiment of FIG. 15, a single control and processing means 216b serves both functions. Accordingly, FIGS. 14–16 will be discussed together, and unless otherwise specified, the embodiments of FIGS. 14 and 15 should be considered to operate similarly.

As best seen in FIGS. 14 and 15, and discussed in detail previously, at least one channel of EEG signal information is acquired from the subject 110 using electrodes 112 and 114 or other suitable sensors, and is supplied to amplifier 118 on leads 116. As best seen in FIG. 16, the signal on leads 116 is an analog, time-domain signal X(t). Amplifier 118 (FIGS. 14 and 15) provides an amplified version of the signal on lead 130 (FIGS. 14, 15, and 16). Anti-aliasing filter 164 (FIGS. 14 and 15) supplies a low-pass-filtered version of the amplified EEG signal on lead 310 (FIGS. 14–16). According to an aspect of the present invention, the cut-off frequency and other characteristics of the filter 164 are selected such that the filtered output signal includes frequency components substantially above 30 Hz. According to traditional EEG doctrine, signal components above 30 Hz have been considered unusable or "noise" and have therefore been discarded or ignored.

Analog-to-digital conversion means 212 (FIGS. 14 and 15) samples the filtered and amplified EEG signal at a selected sampling rate and converts each sample to a "word" or unit of digital data. As discussed above, the sampling rate $f_s$ must be at least twice the maximum frequency $f_{max}$ of the signal being converted. For example, if the maximum frequency $f_{max}$ is 475 Hz, then the sampling rate $f_s$ must be at least 950 samples per second. The resolution of the analog-to-digital conversion means 212—that is, the length, in bits, of the unit of digital data produced by the analog-to-digital conversion means 212 for each sample—determines the smallest difference between analog samples which can be represented by distinct output codes.

It is believed that, in the current state of the A-D converter art, word lengths in the 12-bit range provide adequate precision at moderate cost. A shorter word length might provide insufficient precision, but could be usable if predominant signal components (such as those from approximately 0–30 Hz and a power line noise spike at 50 or 60 Hz), which may not be of interest in the inventive drowsiness detection system 100, are substantially attenuated by appropriate filtering in the analog domain before the EEG signal is presented to the analog-to-digital conversion means.

As best seen in FIGS. 14–15, control and processing means 216 is connected to analog-to-digital conversion means 212 and to storage means 214. Control and processing means 216 controls the A-D conversion process, routes the resulting digital data corresponding to converted digital samples to the storage means 214, and forwards the sampled data to the drowsiness analysis means 136.

As best seen in FIG. 14, in a first embodiment 700 of the invention, two separate control and processing means 216a and 218a may be provided to serve the signal acquisition means 132a and drowsiness analysis means 136 respectively. As best seen in FIG. 15, in a second embodiment 800 of the invention, a single control and processing means 216b may be provided to serve both signal acquisition means 132b and drowsiness analysis means 136b. Each of the control and processing means 216a, 218a, and 216b, could provide additional functions as required in the application, such as artifact detection and thresholding. In the first and second preferred embodiments 700, 800 of the invention, control and processing means 216 and 218 are preferably implemented using a suitable programmable computer having a central processor, such as a commercially-available general-purpose microprocessor or digital signal processor, coupled to appropriate storage means 214 and input/output support components (not shown), or a single-chip microcomputer with storage means 214 and input/output support disposed internally or externally. For example, a personal computer or single-board computer having an Intel "i486" or equivalent central processor could be used.

If separate control and processing means 216 and 218 are provided for data acquisition and analysis, these two systems are preferably interconnected using any suitable computer interconnection medium 794. In the preferred embodiment 800, an Ethernet local area network is used as the interconnection medium, but others, such as a high-speed serial data link, or an IEEE-488-type instrumentation bus, could also be used.

The data from analog-to-digital conversion means 212 corresponding to the sampled EEG signal is supplied via data path (or leads) 314 (FIGS. 14–16) to storage means 214. As discussed previously, the drowsiness analysis means 136 operates on successive, overlapping segments of data or "windows" representing the subject's EEG signal during corresponding time intervals. Storage means 214 should provide sufficient storage for these operations. Storage means 214 may be implemented using any suitable read-write storage or memory. For example, storage means 214 may be implemented using semiconductor "RAM", "EEPROM," or "FLASH" memory, rotating magnetic media, or any other appropriate storage.

In the first and second preferred embodiments 700, 800, the functions of drowsiness analysis means 136 are preferably implemented using known digital signal processing techniques. Thus, as best seen in FIG. 14, in the first preferred embodiment 700, all of the functional blocks or components within the confines of drowsiness analysis means 136, may be implemented using appropriate software components running in analysis control and processing means 218a. As best seen in FIG. 15, in the second preferred embodiment 800, all of the functional blocks or components of drowsiness analysis means 136 are preferably implemented using appropriate software components running in the control and processing means 216a. However, each functional block of drowsiness analysis means 136 could also be implemented using appropriate digital signal processing hardware components.

Interconnections between the components of drowsiness analysis means 136 are designated herein as "data paths." In an embodiment in which the functions of drowsiness analysis means 136 are implemented using software running in a programmable general-purpose digital computer, the data paths discussed herein will typically be regions in memory which are shared by or accessible to the relevant software components. In an embodiment in which the functions of drowsiness analysis means 136 are implemented using digital signal processing hardware, the data paths discussed herein may be any suitable data interconnection between the components, such as a serial data link, a data bus, or shared memory.

Figure 3:
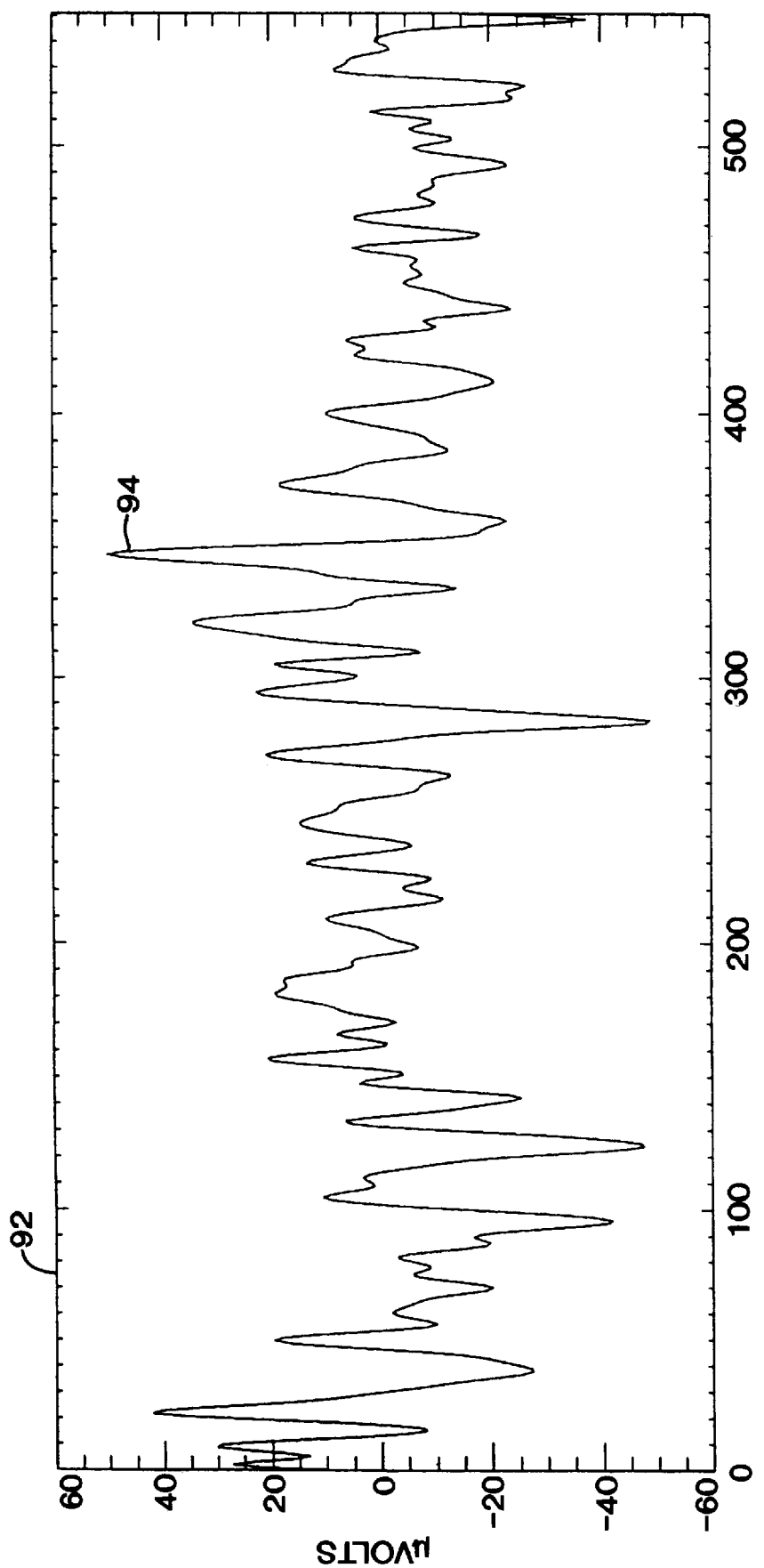
FIG. 3 is a graph showing an excerpt of an EEG waveform acquired using an EEG recording system according to prior-art techniques as shown in FIG. 1, and employing a low-pass filter having the response shown in FIG. 2.
Figure 7:
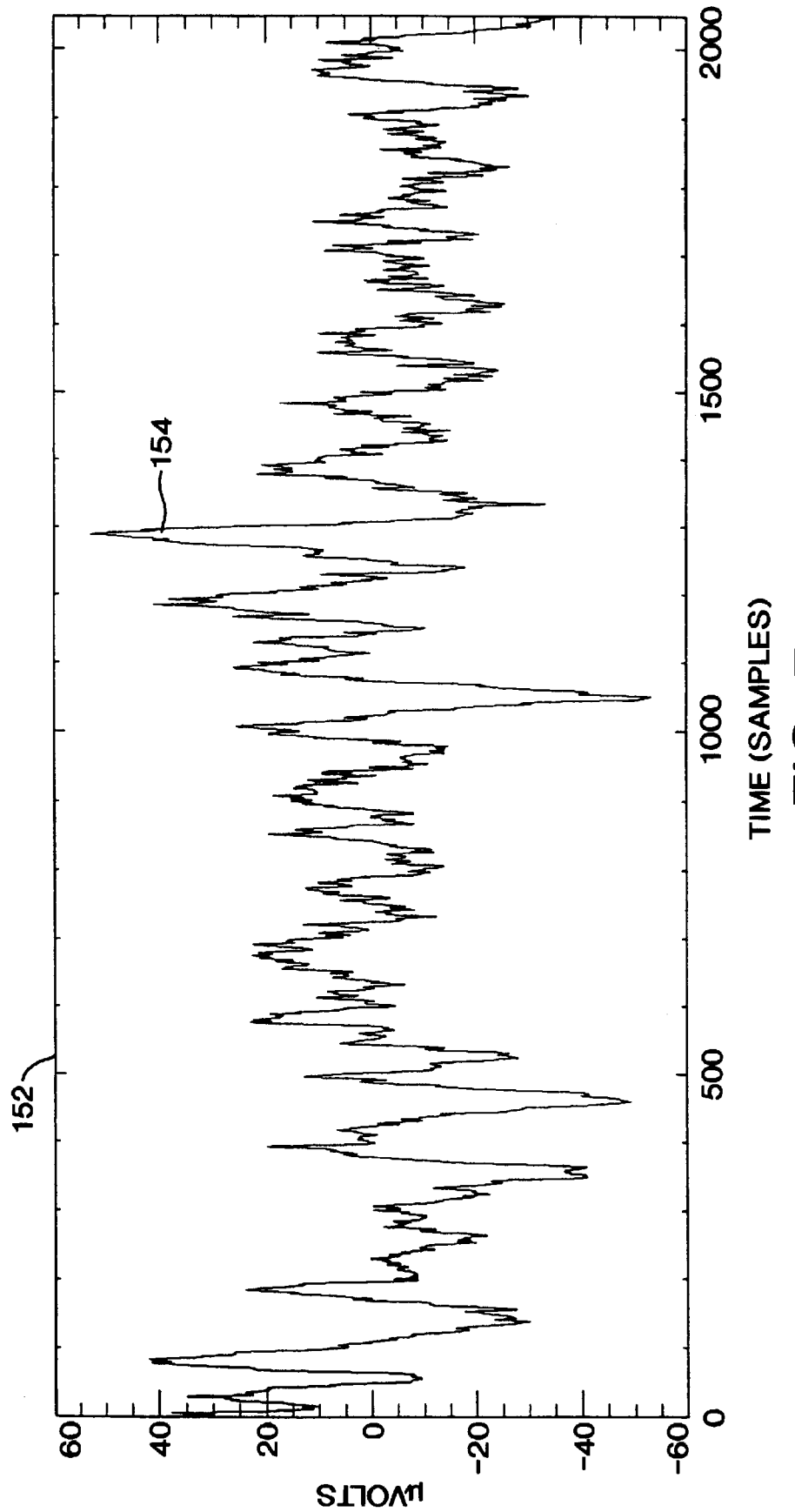
FIG. 7 is a graph showing an excerpt of an EEG waveform acquired using an experimental embodiment of the inventive alertness monitoring system of FIG. 5.

Stored EEG signal data is supplied from storage means 214 to data selection means 220 via a data path 316. The digitized EEG data is stored as a plurality of EEG signal samples corresponding the subject's EEG signal acquired over a time interval of interest, and may be arranged as a contiguous group of the most recently acquired samples. FIG. 7 is a graph 152 showing the time evolution of an exemplary EEG signal 154 which was acquired from a human subject using an experimental embodiment similar to the first preferred embodiment 700 disclosed herein. The graph 152 was plotted from data which had been sampled as disclosed herein and stored in a form corresponding to data element 316 of FIG. 16 (see below). The dependent variable in FIG. 7 is the amplitude of the EEG signal in microvolts. The sampling rate at which this signal was acquired was 950 samples per second. Data corresponding to 2048 samples are plotted. The independent variable in FIG. 7 is an ordinal number corresponding to the position of each data point in the sequence in which the data was acquired. Because the sampling rate was constant, this sample number is equivalent to time. The resulting time interval represented in the graph is approximately 2.16 seconds. A first-order Butterworth filter having a half-amplitude frequency of approximately 100 Hz was used as an anti-aliasing filter in the experimental embodiment. Although acceptable results were achieved using this filter, a higher performance filter, such as filter 610 (FIG. 6a), may provide improved system performance as it does provide improved anti-aliasing performance. Comparing graph 152 with graph 92 (see FIG. 3), which shows an equivalent signal 94 acquired according to prior-art methods, it is apparent that significant high-frequency information is present in signal 154 due to acquisition according to the present invention.

A sufficient quantity of data must be available for processing by drowsiness analysis means 136. In a drowsiness analysis means 136 that operates on successive data batches comprising overlapping segments of data or "windows" representing the subject's EEG signal during a brief corresponding time interval, the window defines the quantity of EEG signal data on which the drowsiness analysis means 136 operates at a particular time. Each successive operation of drowsiness analysis means 136 may operate on a segment of newly obtained data and a segment of previously analyzed data, so that each analysis window overlaps the previous analysis window by a selected amount. In the first and second preferred embodiments 700, 800 of the invention, each window overlaps the previous window by one half of the width of the analysis window, but other amounts of overlap could also be used.

The size and overlap of analysis windows may be selected according to application requirements. The window size should be large enough to provide sufficient resolution for downstream analysis (discussed further in greater detail), but small enough that the analysis can be computed acceptably quickly using affordable computing resources. The window overlap should also be selected to allow the output measure to be frequently determined, so that adequate warning is provided if a subject becomes excessively drowsy.

Data selection means 220 extracts a quantity of data corresponding to one analysis window, and presents it to windowing function means 222 on data path 320. The process of extracting the data may be referred to as "rectangular windowing." The extraction or selection process is equivalent to multiplying all of the data by a function having the value 1 during the window period and zero at all other times. The windowing function means 222 multiplies the data in the selected window by a window function which reduces the amplitude of the samples in the neighborhood of the beginning and end of the window.

A number of windowing functions such as rectangular, Hamming, Hanning, and Blackman, are known in the signal processing art. In the preferred embodiments 700, 800, a Hanning window function, which results in considerably smaller side-lobes than the rectangular function (at the expense of a broader main lobe), may be used. If analysis warrants, other windowing functions may be employed (such as the Dolph-Chebyshev function) to provide improved characteristics over the Hanning function at the expense of some increased complexity. One subsequent processing step performed by drowsiness analysis means 136 is spectral or frequency analysis. The data window type (rectangular, Hanning, Hamming, or Blackman, etc.) influences the resolution of the downstream frequency analysis by "blurring" the results in the frequency domain.

The output of the windowing function means 222 is provided to frequency analysis means 224 via data path 322 as a vector of time-domain digital samples. The length of the vector (i.e., the number of samples) is equivalent to the window width.

Frequency analysis means 224 employs any suitable frequency or spectral analysis technique to determine the amplitude and phase of components of the sampled EEG signal at various frequencies throughout a defined frequency range of interest. For example, in a preferred embodiment of the invention, the Fast Fourier Transform (FFT) may be used.

The FFT is a frequency analysis technique which is well known in the signal processing art, and which converts a vector of N regularly-spaced time-domain samples of a signal into a vector of data representing the signal in the frequency domain. Each element of the FFT vector is a complex number representing the amplitude and phase of the signal component at one of the N regularly-spaced frequencies. The FFT is a good candidate for use in the preferred embodiments of the present invention because its properties are well understood, and there exist high-speed implementations of the algorithm which are commercially and otherwise available in software and hardware. Other suitable frequency analysis techniques could also be used to implement frequency analysis means 224.

The output of the frequency analysis means 224 is provided to power spectral density determination means 226 via data path 324. The frequency analysis output 324 is an output vector in which each element is a complex number representing the amplitude and phase of the signal component at one of the N regularly-spaced frequencies.

The power spectral density determination means 226 determines the power present in the sampled EEG signal at each frequency point by squaring the magnitude of each component of the FFT output vector. The use of frequency or spectral analysis allows the isolation of EEG signals in specific frequency ranges which carry information related to alertness, drowsiness, and sleep. Proper selection of anti-aliasing filter characteristics and sampling rates is essential in order to preserve signal components in these frequency ranges. In previously discussed trials using an experimental embodiment of the invention, a sampling rate of 950 samples per second, with a suitable anti-aliasing filter, was used to capture signal components up to 475 Hz. Frequency components in the range from 80 to 475 Hz were found particularly useful in detecting the onset of extreme drowsiness, and provided improved drowsiness detection performance compared to that reported for prior-art systems. However, it is believed that other frequency ranges above 30 Hz may also produce useful results, and perhaps may provide even better drowsiness detection performance.

Figure 8:
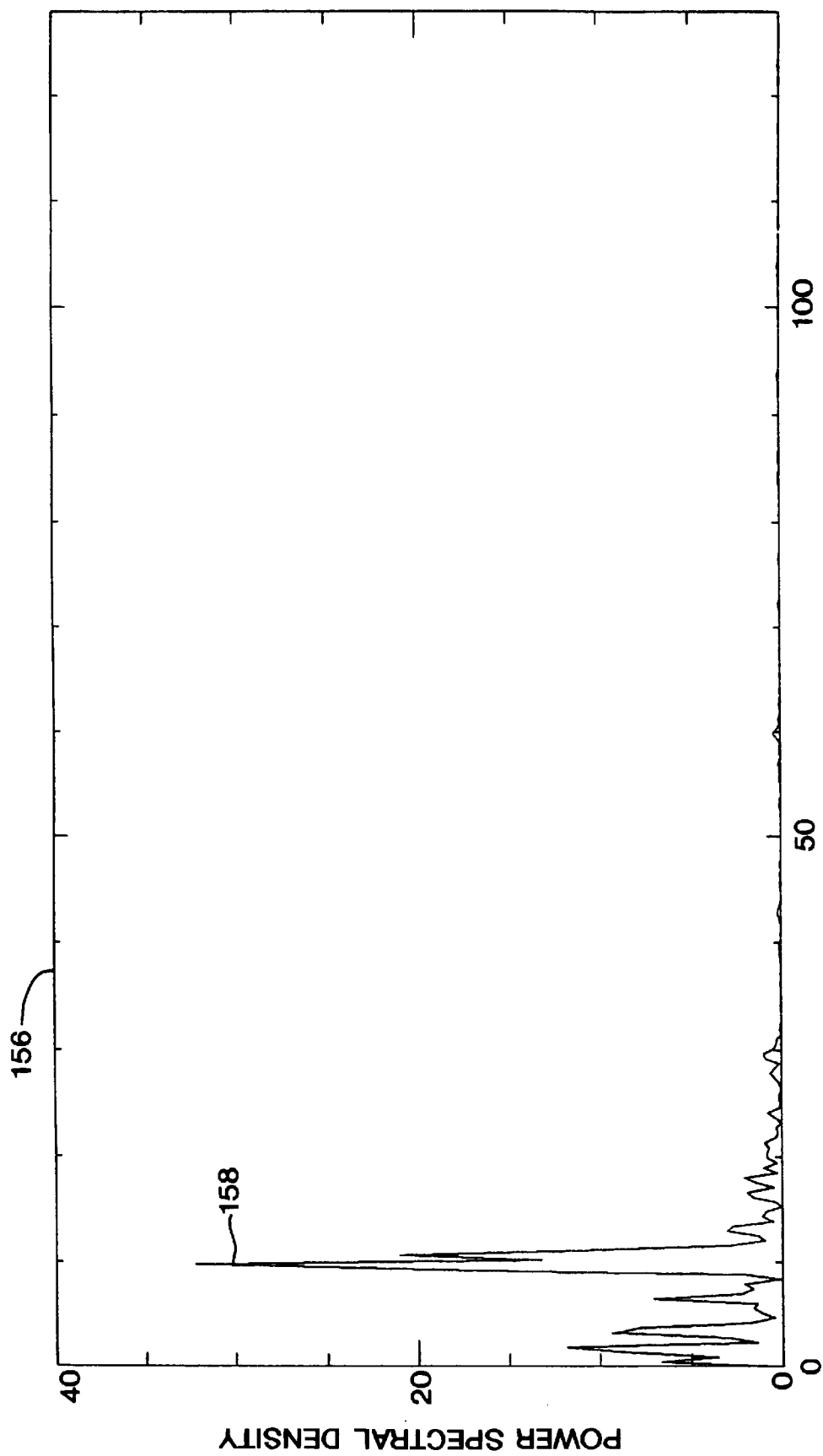
FIG. 8 is a graph showing the power spectral density calculated over the frequency range 0–128 Hz from the EEG waveform which is depicted in FIG. 7 and which was acquired using the inventive alertness monitoring system of FIG. 5.
Figure 9:
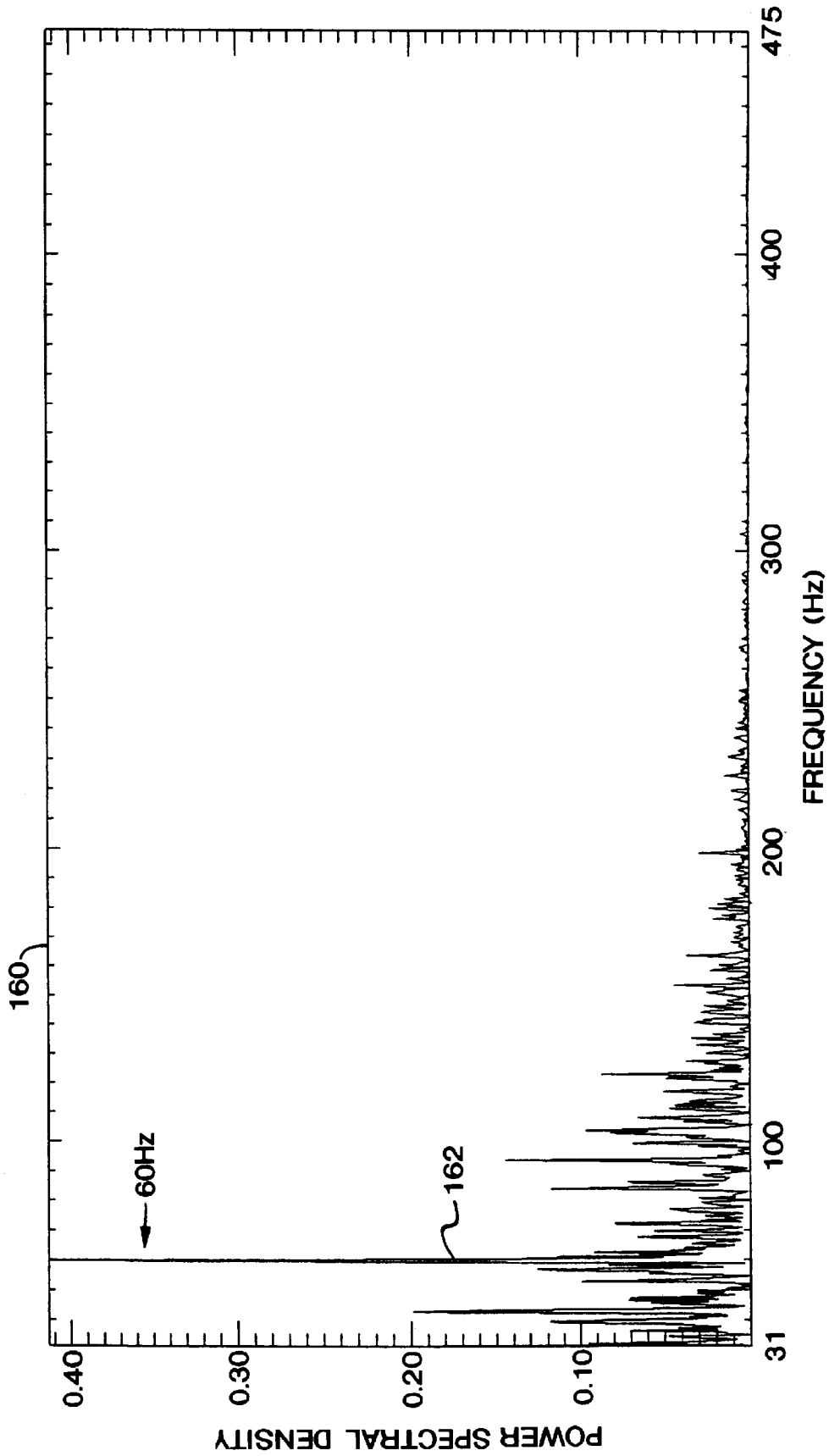
FIG. 9 is a graph showing the power spectral density calculated over the frequency range 31–475 Hz from the EEG waveform which is depicted in FIG. 7 and which was acquired using an experimental embodiment of the inventive alertness monitoring system of FIG. 5.

FIG. 8 is a graph 156 of the power spectral density 158 from 0–128 Hz, determined from the sampled signal 154 shown in FIG. 7. Almost all of the energy in this signal is below 30 Hz, despite the relatively high sampling rate and an appropriately selected anti-aliasing filter which were used to acquire the data from which FIGS. 7–8 were produced. A tiny spike appears at 60 Hz, and represents signals attributable to commercial power line noise acquired with the signal. FIG. 9 is a graph 160 of the power spectral density 162 from 31–475 Hz, determined from the same sampled signal 154 used to produce graph 156 of FIG. 8. Elimination of the frequencies from 0–30 Hz allows the graph to be re-scaled so that the power present at frequencies above 30 Hz is now visible.

FIGS. 10–11 are graphs depicting two power spectrums in the frequency range 100–475 Hz, derived from EEG signal data obtained from a human subject using an experimental embodiment of the present invention. Table 2, represents in numerically analyzed form, relevant aspects of the data shown graphically in FIGS. 10–11. A comparison of the data in Table 2, and the graphs of FIGS. 10–11, will provide insight into the drowsiness-related information contained in higher-frequency components of a subject's EEG signal. In FIG. 10, the power spectrum corresponds to EEG data obtained during "hits" —that is, intervals during which the subject successfully responded to a visual stimulus presented according to the experiment. In FIG. 11, the power spectrum corresponds to EEG data obtained during "misses" —that is, intervals during which the subject failed to respond to a visual stimulus. Table 2 shows, for several selected frequency ranges and subranges, the amount of energy in the EEG signals attributable to the frequencies in each range, for hits and misses. The "Change in Energy" column presents a factor for each selected frequency range indicating the relative amount of energy in that range for EEG signals acquired during "hit" events, compared to the energy in the range for signals acquired during "miss" events. If the entry for a frequency range in the "Change in Energy column is positive, then it represents the quotient formed by the energy in the "miss" column divided by the energy in the "hits" column. If the entry for a frequency range in the "Change in Energy column is negative, then it represents the quotient formed by energy in the "hits" column divided by the energy in the "miss" column.

TABLE 2

RESULTS OF TESTS USING EXPERIMENTAL EMBODIMENT

| Frequency Range | Hits | | Misses | | Change in Energy |
|---|---|---|---|---|---|
| | Energy | Fraction of Total | Energy | Fraction of Total | |
| delta (0.5–2) | 2.001e+02 | 46.545% | 1.875e+02 | 41.601% | −1.067 |
| theta (3–7) | 4.496e+01 | 10.462% | 1.155e+02 | 25.619% | +2.568 |
| alpha (8–12) | 9.870e+01 | 22.965% | 4.138e+01 | 9.180% | −2.385 |
| beta (13–30) | 2.303e+01 | 5.358% | 2.241e+01 | 4.972% | −1.028 |
| 0 to 30 Hz | 4.083e+02 | 94.991% | 4.439e+02 | 98.481% | +1.087 |
| 0 to 40 Hz | 4.135e+02 | 96.197% | 4.469e+02 | 99.141% | +1.081 |
| 0 to 475 Hz | 4.298e+02 | 100.000% | 4.508e+02 | 100.000% | +1.049 |

TABLE 2-continued

RESULTS OF TESTS USING EXPERIMENTAL EMBODIMENT

| Frequency Range | Hits Energy | Fraction of Total | Misses Energy | Fraction of Total | Change in Energy |
|---|---|---|---|---|---|
| 31 to 100 Hz | 1.547e+01 | 73.521% | 5.965e+00 | 91.672% | −2.593 |
| 100 to 200 Hz | 4.239e+00 | 20.146% | 4.701e−01 | 7.224% | −9.017 |
| 100 to 300 Hz | 5.249e+00 | 24.946% | 5.225e−01 | 8.029% | −10.046 |
| 100 to 475 Hz | 5.571e+00 | 26.479% | 5.419e−01 | 8.328% | −10.282 |
| 200 to 475 Hz | 1.333e+00 | 6.333% | 7.180e−02 | 1.103% | −18.559 |
| 300 to 475 Hz | 3.225e−01 | 1.533% | 1.941e−02 | 0.298% | −16.613 |
| 31 to 475 Hz | 2.104e+01 | 100.000% | 6.507e+00 | 100.000% | −3.234 |

To produce the graph of FIG. 10, the EEG data corresponding to 25 hits was selected according to the following criteria:

1. the subject successfully responded to a visual stimulus;
2. no muscle or movement artifact was detected in the record;
3. the event appeared within a string of at least eight consecutive hits; and
4. the event did not occur at a hit/miss transition or boundary.

The power spectrum was calculated for the EEG data corresponding to each selected hit. At each discrete frequency in the power spectrum, the mean of the power spectrum value from the 25 events was determined and this mean was used to produce the graph. Thus, the graph of FIG. 10 represents the mean of the power spectrum calculated from the 25 hits.

To produce the graph of FIG. 11, the EEG data corresponding to 20 misses was selected according to the following criteria:

1. the subject failed to respond to a visual stimulus, and the failure was not attributable to external causes;
2. no muscle or movement artifact was detected in the record;
3. the event appeared within a string of at least eight consecutive misses;
4. the event did not occur at a hit/miss transition or boundary; and
5. the event was not one of the first few misses among a string of misses.

The mean power spectrum was calculated for the misses in a manner similar to that described for the hits.

Activity at 60 Hz and odd harmonics thereof has been eliminated by noise removal means 228 (described further in detail) from the power spectrum data from which the graphs 164, 170 of FIGS. 10 and 11 were produced.

The EEG data shown in FIG. 10 (i.e., the hit events) corresponds, on average, to a subject in an alert state commensurate with good performance. The EEG data shown in FIG. 11 (i.e., the miss events) corresponds, on average, to a subject in a state of extreme drowsiness commensurate with failed performance. The scale of the vertical axis of graph 164 of FIG. 10 is 10 times that of graph 170 of FIG. 11. Comparing the graphs of FIGS. 10–11, it can be observed that the total energy represented in the power spectrum 164 (FIG. 10) corresponding to hits is approximately 10 times greater than the total energy represented in the power spectrum 170 (FIG. 11) corresponding to misses. Thus, in this experimental data, there is a significant correlation between a subject's state of alertness, drowsiness, or sleep, and the energy in the EEG signal in certain frequency bands. The graphs of FIGS. 10–11 illustrate this phenomenon for the frequency range of 100–475 Hz. Based on these and other experimental results, it is believed that this correlation is a general characteristic of the human population that extends across a wide variety of different tasks.

Figure 4:
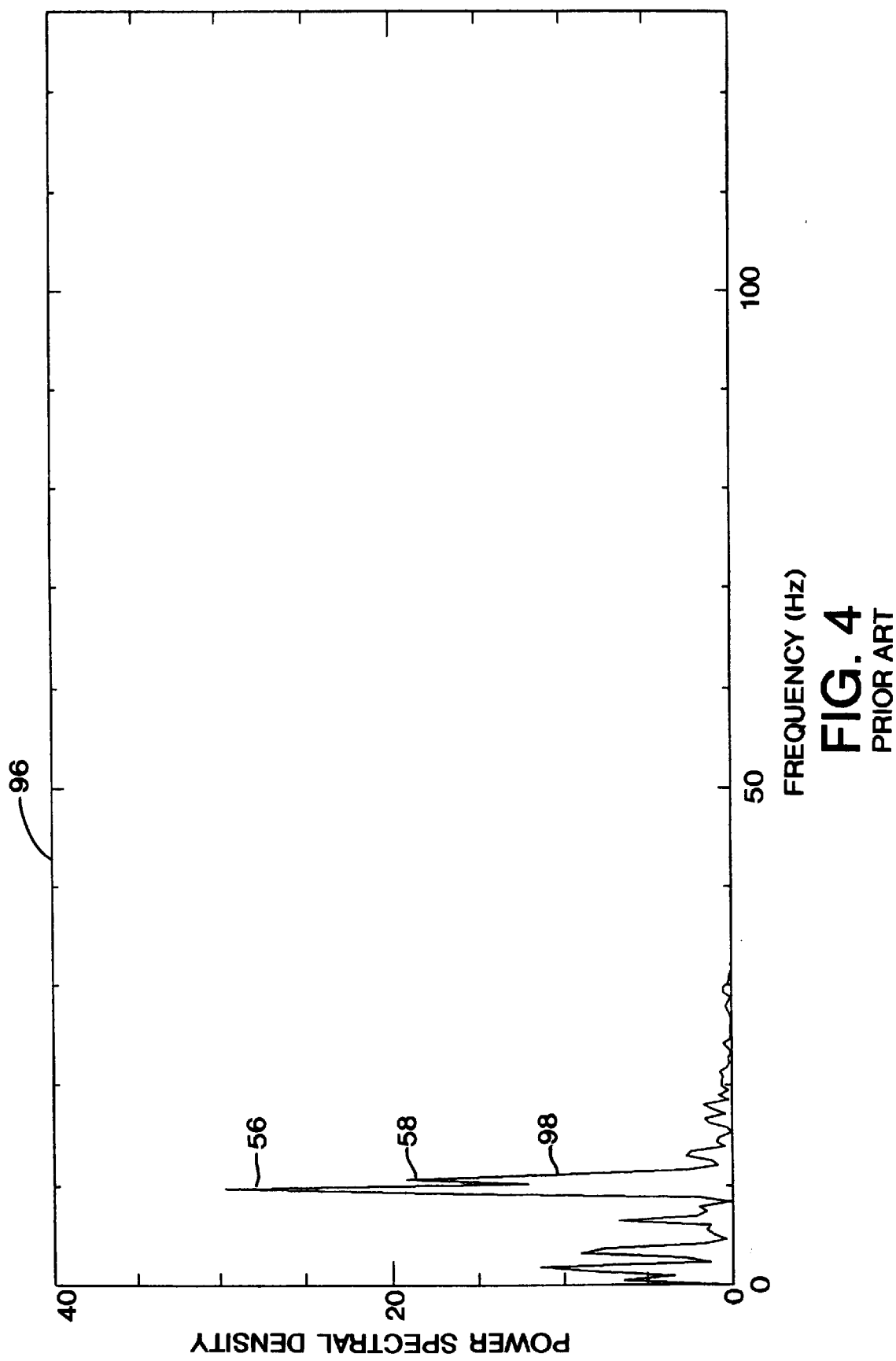
FIG. 4 is a graph showing the power spectral density calculated over the frequency range 0–128 Hz from the EEG waveform which is depicted in FIG. 3 and which was acquired using the prior-art EEG recording system and low-pass filter of FIGS. 1–2.

It is believed that: (1) the recognition of a strong correlation between a subject's state of alertness, drowsiness, or sleep, and the energy or amplitude of the EEG signal at frequencies above 30 Hz; and (2) the exploitation of this correlation in a system for monitoring a subject's state of alertness, drowsiness, or sleep, are novel and nonobvious aspects of the present invention. As best seen in FIGS. 4 and 8, almost all of the energy in the subject's EEG signal is contained in components at frequencies below 30 Hz, regardless of the subject's state of alertness, drowsiness, or sleep. In FIG. 8, the only significant component visible above approximately 30 Hz is a small peak at 60 Hz, which corresponds to noise derived from the commercial electrical power supply system. As best seen in FIG. 9, although the amplitude of the 60 Hz noise peak is minuscule compared to that of the predominant 12–13 Hz peak of FIG. 8, it is many times larger than any of the higher frequency signal components disovered to be useful in drowsiness detection.

Because of the large disparity between the amplitudes of the 0–30 Hz components and any components which may occur at higher frequencies, when displayed at normal scales and resolutions, the 0–30 Hz components effectively mask the presence of higher-frequency components. Thus, neither the presence of useful EEG signal energy at frequencies over 30 Hz, nor the strong correlation between such signal energy and a subject's drowsiness, would have been apparent using normal data visualization and analysis techniques. Further, according to traditional EEG doctrine, rhythmic components in EEG signals at frequencies above approximately 30 Hz have been considered to be noise, and in the prior art, such components have been systematically discarded by filtering or, at best, ignored. Thus, the prior art discouraged practitioners from acquiring or exploiting rhythmic EEG signal components above approximately 30 Hz in drowsiness monitoring and other related applications, effectively teaching away from the present invention.

Components 226–244 are directed to extracting and exploiting information which has been determined to be useful in drowsiness detection from the acquired EEG signal data that has been transformed using frequency analysis techniques.

The output of the power spectral density determination means 226 is supplied to noise removal means 228 via data path 326. The output of the power spectral density determination means 226 is a vector in which each element is a scalar representing the power in the sampled EEG signal at each frequency point produced in the frequency analysis.

The noise removal means 228 replaces elements of the power spectral density vector at or adjacent to known noise frequencies with neighboring values. It is very difficult to avoid infiltration of noise at the commercial power line frequency (and its harmonics) in many real-world applications due to the presence of lighting and electrical equipment in the region in which the data is collected. Even in clinical and research settings, it is nearly impossible to avoid acquiring such noise. Accordingly, for harmonics of the commercial power supply frequency (typically 60 Hz in North America), the noise removal means 228 replaces the power spectral density entries corresponding to that frequency and its upper and lower nearest neighbors with the value of one of the nearest neighbors. It may also be necessary to filter this power line noise in the analog domain, depending on the amplitude of the noise which is present. Other known sources of noise could be similarly eliminated.

The output of the noise removal means 228 is provided to filter compensation means 230 via data path 328. The output 328 of the noise removal means is essentially the same as the power spectral density (PSD) vector 326, with entries in the neighborhood of noise frequencies adjusted.

As discussed previously, the attenuation or cut-off portion of the frequency response of the anti-aliasing filter means 164 may intrude into the frequency range of interest in drowsiness detection, thereby attenuating signal components which may be useful. The filter compensation means 230 compensates for the effect of the anti-aliasing filter means 164 by multiplying the entries of the power spectral density vector 326 by a suitable compensating function. The compensating function depends on the characteristics of the particular filter used to implement filter means 164. For most filter designs of known characteristics, such as the sixth order Butterworth filter 610 of FIG. 6a, the compensating function is relatively simple. The PSD vector entries corresponding to frequencies in the attenuation region are multiplied by a compensating factor computed from the filter characteristics. The output of the filter compensation means 230 is provided to spectral bin grouping means 232 via data path 330.

According to an aspect of the present invention, components 232–244 determine, responsive to the compensated PSD vector 330, an output measure signal on lead 138 indicating the subject's state of alertness, drowsiness, or sleep. In trials of an experimental embodiment of the invention using human subjects, a high correlation has been observed between values of the output measure which exceed a predefined threshold and the subjects' failures to respond to visual stimuli.

Spectral bin grouping means 232 defines a plurality of selected frequency ranges for which the energy in each range will be determined. For example, in a preferred embodiment, five spectral bins may be defined as: 80–120 Hz; 120–178 Hz; 181–240 Hz; 240–299 Hz; and 301–420 Hz. Although these spectral bins are used in preferred embodiments of the invention, other spectral bin choices could also be used. In fact, it is believed that at least some of the advantages of the present invention may be obtained using one or more reasonably selected subranges of frequencies between approximately 30 Hz and 500 Hz. Further, the spectral bin grouping means could also include a substantially wider range of frequencies than that represented in the spectral bins described above. For example, the spectral bin grouping means 232 could use some frequencies below 30 Hz, provided that a substantial contribution to the drowsiness output measure (discussed further in detail) is based on signal information from frequencies above 30 Hz. Although the value to a drowsiness detection system of EEG signal components at frequencies above 500 Hz has not been established, further investigation may reveal that components at frequencies above 500 Hz may enable drowsiness detection systems to provide even better performance. The output 332 of the spectral bin grouping means 232 appears as groups corresponding to each bin, containing the power-spectral density values for the frequencies in that bin. The output of the spectral bin grouping means 232 is provided to bin energy determination means 234 via data path 332.

The bin energy determination means 234 determines the energy in each spectral bin as the arithmetic sum of the power values in each bin. The output of the bin energy determination means 234 is a vector containing an entry for each bin representing the energy in the frequency range associated with that bin. The output of the bin energy determination means 234 is provided to bin energy inversion means 236 via data path 334. The bin energy inversion means 236 determines the inverse of the energy in each spectral bin. The use of the inverse in determining the drowsiness output measure was chosen, in part, because it causes a desired diminution of the output measure in response to increased energy in the frequency bands of interest. Because increases in high-frequency energy tend to indicate wakefulness, the inverse operation produces an output measure having a low value for a wakeful, alert subject, and higher values for drowsy subjects. The use of the inverse also provides a non-linearity in the output measure, which is desirable because very low values of high-frequency energy correspond to extreme drowsiness, and the non-linearity provides increased sensitivity at such low energy values. However, the desired output signal response could be achieved using other functions. In some applications, different types of output signals may be desired, eliminating the need for the inverse, or the energy values in the frequency bands of interest could be used directly without additional processing.

The output of the bin energy inversion means 236 is provided to weighting means 238 via data path 336. A weighting function generator means 240 supplies a weighting function for use by the weighting means 238 in determining how to weight the inverse energy value for each spectral bin in the final output measure. In a currently preferred embodiment of the invention, each bin may be equally weighted—e.g., the function provided by weighting function generator means 240 may be 1, so that the weighting means simply multiplies each inverse energy value by 1. Alternatively, each bin could be weighted by a different scalar value, and these values could be generated by a function. Improved weighting functions may be discovered through additional experimentation.

The weighted, inverted spectral bin energy values are provided by weighting means 238 to summing means 242 via a data path 338. The summing means 242 determines the arithmetic sum of the weighted inverse energy values and optionally presents it to interpolation means 244 via data path 340.

Interpolation means 244 may optionally be provided to generate an output signal 138 (which may be an analog signal, a discrete-valued signal, or values in memory). The interpolation means 244 thus continuously presents an output measure signal 138 which represents the state of the subject's alertness, drowsiness, or sleep, during the period in which the subject's EEG signal was acquired. If the interpolation means 244 is not used, then the output of summing means 242 may be used in a similar manner to produce the drowsiness output measure by connecting lead 340 to output signal lead 138 (as indicated by broken line 138a). If the drowsiness analysis process is performed essentially in "real-time," then the output measure signal 138 will lag the subject's actual drowsiness by an insignificant amount. Thus, the output measure signal 138 may be effectively used to produce an alarm when the output measure signal exceeds a threshold indicating that the subject has become excessively drowsy and may be unable to safely perform a task. As best seen in FIG. 5, the output measure signal 138 may be conditioned by comparison with a threshold and by indications that artifact may be present in the subject's EEG signal, before it is used to produce a display or alarm.

FIGS. 20a–20c are graphs of the output measure produced in an experimental embodiment of the invention using EEG data acquired during trials using human subjects. The output measures shown are equivalent to and determined in substantially the same manner as the output measure supplied on lead 138 from the first and second embodiments 700 and 800 (FIGS. 12–16) of the invention. The dependent variable in each graph is the value of the output measure. Each point on the plots corresponds to the output value determined from a 2048-point data analysis window of the subject's EEG data. As described previously in connection with data selection means 220, adjacent windows of data are offset by 1024 samples, so that each window includes 1024 samples of "new" data and 1024 samples from the previous window. The independent variable in each of FIGS. 20a–20c time in seconds over which the measure was determined.

The graphs of FIGS. 20a–20c each include upper and lower threshold markers 916 and 918, which extend horizontally at 17 and 12 units on the output measure scale, respectively. Output measure values increase with subject drowsiness. Output measure values which exceed the upper threshold 916 indicate that the subject was excessively drowsy (or asleep) during the corresponding time interval. Output measure values which are below the lower threshold 918 indicate that the subject was wakeful or alert during the corresponding time interval. Output measure values which lie between the thresholds 916 and 918 do not definitely indicate either alertness or drowsiness. However, the slope of the output measure can be used to interpret behavioral trends. For example, if the output measure is between the thresholds and the slope is positive, the subject is approaching an excessively drowsy condition. If the slope is negative, the subject is approaching a wakeful condition.

The thresholds 916, 918 were selected based on results from experimental examinations of several subjects, and are believed to be generally applicable for drowsiness detection. As best seen in FIG. 19 (described further in detail), a suitable method for determining an appropriate drowsiness threshold, which is tailored to a particular individual using EEG signal data acquired from that individual, could also be used in conjunction with the drowsiness detection system of the present invention.

FIG. 20a is a graph 910 showing two superimposed output measure plots 912 and 914 which were determined using EEG signals acquired from a human subject during two different examination periods. Each of the segments shown represents approximately 8.62 minutes. A first plot 912 was derived from data acquired while the subject was observed to be in a state of wakefulness, based on the subject's physical behavior while performing a visual task. A second plot 914 was derived from data acquired later, while the subject was resting on a bed and allowed to fall asleep. In the first plot 912, the output measure never exceeds the lower threshold 918. In the second plot 914, the output measure exhibits several initial episodes in which the measure crosses the upper threshold, followed by a period during which the measure continuously exceeds the upper threshold 916 and tends to increase over time. Plot 912 is believed to be representative of the behavior of the output measure for wakeful human subjects. Plot 914 is believed to be representative of the behavior of the output measure for a human subject who becomes drowsy and falls asleep. The output measure is believed to be a sensitive indicator of the drowsiness of a human subject.

FIG. 20b is a graph 920 showing an output measure plot 922 determined using EEG signals acquired from a human subject during approximately 9.29 minutes of an examination period. The EEG signals were acquired during subject performance trials conducted as previously described in connection with an experimental embodiment of the invention. The subject was instructed to respond to a series of visual stimuli presented at random intervals. If the subject failed to respond to a stimulus within a predetermined period of time, additional stimuli were presented at regular time intervals until the subject responded to two consecutive stimuli. Each stimulus is represented on the graph 920 as a solid vertical line (such as line 924) if the subject responded successfully, or as a broken vertical line (such as line 926) if the subject failed to respond. Graph 920 reveals excellent agreement between the subject's actual drowsiness, as indicated by test performance, and that predicted by the output measure 922. In general, adequate subject performance, which is indicated by solid vertical lines, is accompanied by values of the output measure below the lower threshold 918. Response failures 928 and 930, including a group 928 of 15 contiguous response failures attributed to a sleep episode lasting approximately 90 seconds, are predicted by excursions of the output measure above the upper threshold 916, prior to the actual failure.

FIG. 20c is a graph 932 showing an output measure plot 934 determined using EEG signals acquired from a human subject during approximately 8.83 minutes of an examination period. EEG signals were acquired during subject performance trials conducted as previously described in connection with an experimental embodiment of the invention. Graph 932 also shows excellent agreement between the subject's actual drowsiness, as indicated by test performance, and that predicted by the value of the output measure 934. Graph 932 suggests that even if the output measure does not exceed the upper threshold 916, performance failures due to drowsiness may be predicted prior to a failure when the value of the output measure is both above the lower threshold and increasing (i.e., the output measure has positive slope). Graph 932 also includes two performance failure episodes which were not the result of excessive drowsiness; instead, these failures occurred because the subject was not paying attention to the visual stimulus display.

FIG. 18 is a flow diagram showing the steps of a method 540 for determining whether a segment or window of sampled EEG data likely contains artifact. According to an aspect of the present invention, the method 540 may be used in conjunction with artifact detection means 148 of drowsiness detection system 500, including the first or second preferred embodiments 700, 800. The artifact detection method 540 may be implemented using data acquisition and processing hardware and software in common with that used to implement the first or second preferred embodiments 700, 800. Alternatively, separate data acquisition and processing hardware and software could also be used. The artifact detection method may also be used in other applications in which it is desired to analyze only artifact-free EEG data.

In step 542, appropriate EEG data is acquired from a subject, and a window of data of appropriate length is selected therefrom. If the artifact detection method is operating in conjunction with one of the first or second preferred embodiments 700, 800 of the invention discussed previously, the selected data may, for example, be obtained from the output of the data selection means 220 of FIGS. 14 and 15. Thus, step 542 may represent all of the data acquisition and related functions and steps performed up to and including data selection means 220 of FIGS. 14 and 15. However, if it is desired to use the artifact detection method 540 in conjunction with an embodiment which does not itself require these data acquisition and selection functions, then means for acquiring and selecting the data may be separately provided.

In step 558, if any samples contained in the selected data window appear to be saturated, the data window is rejected. A sample may be considered to be saturated if its value is the largest or smallest value which can be produced by the analog-to-digital conversion means 212, or if the analog-to-digital conversion means 212 provides an overflow, or similar out-of-range indication.

In step 544, a suitable transform or process is applied to the selected data to convert it from a time-domain representation to a frequency-domain representation. Any suitable frequency analysis method may be used. Several usable frequency analysis methods are discussed in connection with the frequency analysis means 224 of FIGS. 14–15, and step 544 may be implemented using the same frequency analysis technique as used to implement frequency analysis means 224.

In step 546, the power spectral density of the selected data segment is determined using the results of the frequency analysis step. The power spectral density may be determined as described previously in connection with power spectral density determination means 226 of FIG. 14–15.

In step 548, one or more spectral bins, which correspond to selected frequency ranges, are defined. For each spectral bin, the energy contained in that bin is determined using the power spectral density of all frequency components within that bin. In a preferred embodiment of the invention, a single spectral bin, corresponding to the frequency range 30–60 Hz, was defined. This frequency range appears to have adequate sensitivity for use in an artifact detection algorithm. However, a different number of spectral bins, covering other frequency ranges, could also be used. If multiple spectral bins are defined, the energy in all spectral bins may be combined to produce an aggregate energy value.

In step 550, the mean value of the energy determined in step 548 over all windows in the current segment of EEG data is determined. This mean value is then multiplied by an artifact threshold factor to obtain an artifact threshold value. The artifact threshold factor may be experimentally determined. In an experimental embodiment of the invention, an artifact threshold factor of 2.0 was used.

In step 552, the aggregate energy values, which were determined in step 548, are compared to the artifact threshold value. For all of the windows in a particular EEG data segment, if the aggregate energy in any window exceeds the artifact threshold value determined in step 550, that window is considered to be contaminated by artifact, and is indicated accordingly in the artifact output measure on lead 150.

In step 556, which is optional, inputs 164 representing certain secondary artifact detection factors or indicators may be considered in determining whether EEG data is contaminated by artifact. For example, signals or other information may be derived from a video camera or a motion detector which could be useful for artifact detection. Thus, the artifact detection method 540 may produce an artifact present signal 150 if artifact is detected in either the comparison step 552 or the secondary artifact consideration step 556.

In some applications, it may be unnecessary to explicitly provide artifact detection means 128, including means for implementing the artifact detection method 540 of FIG. 18. Implementations which produce an output measure as described in connection with the first and second preferred embodiments 700, 800 are tolerant of artifact, in that the presence of artifact is accompanied by a significant increase in EEG signal energy across all frequencies, which causes a decrease in the value of the output measure. Artifact resulting from sustained movement or other activity indicating wakefulness changes the output measure in the direction of wakefulness, and does not detract from the performance of the drowsiness detection system.

FIG. 19 is a flow diagram showing the steps of a method 510 for determining a drowsiness threshold for an individual based on EEG signals acquired from the individual while alert. According to an aspect of the present invention, the method 510 may be used in conjunction with the threshold value generator means 144 of drowsiness detection system 500, including the first or second preferred embodiments 700, 800. The individual threshold determination method 510 may be implemented using data acquisition and processing hardware and software in common with that used to implement the first or second preferred embodiments 700, 800. Alternatively, separate data acquisition and processing hardware and software could also be used.

In step 512, EEG data is acquired for use in the method from an alert or wakeful subject. To obtain sufficient EEG signal information from an individual to determine an appropriate threshold, data is preferably acquired over a threshold determination period of approximately 10 minutes, although adequate results may be obtained even if a substantial deviation from this period is used. The EEG signal information needed for use with the threshold determination method 510 may be acquired and stored for subsequent processing, or may be used in real time. If the threshold determination method 510 is operating in conjunction with one of the first or second preferred embodiments 700, 800 of the invention discussed previously, the data may, for example, be obtained from the output of storage means 214 of FIGS. 14 and 15. Thus, step 512 may represent all of the data acquisition and related functions and steps performed up to and including storage means 214 of FIGS. 14 and 15.

In step 520, the drowsiness output measure is determined using the data collected during the threshold determination period. The output measure may be determined as previously disclosed in connection with the drowsiness analysis means 856, 136. In some applications, one of the drowsiness analysis means 136, 756, 856 of FIGS. 14 or 15 may be operated during the threshold determination period, and the output measure produced therefrom may be recorded for subsequent use. In step 522, an artifact indication signal is preferably determined over the same threshold determination period. For example, the artifact detection means 148 may be operated in conjunction with the artifact determination method 540 of FIG. 18 during the threshold determination period, and the artifact indication signal produced therefrom may be recorded for subsequent use.

In step 514, the results of artifact detection step 522 are used to condition the results of the output measure determination step 520, so that only output measure information produced during artifact-free periods is retained. In step 516, the mean of the output measure over the artifact-free portion of the threshold determination period is determined. The mean output measure value determined in step 516 establishes an alert baseline value of the output measure for the individual subject being examined. Because artifact in EEG data tends to reduce the output measure, removal of output measure values determined during artifact-contaminated periods avoids an artificial reduction of the baseline value, thereby reducing the potential for false positive drowsiness indications.

In step 518, the subject's alert baseline output measure value determined in step 516 is multiplied by an appropriate threshold factor to determine a threshold value for that individual. The threshold value may be supplied on lead 146 for use by comparison means 140 (FIG. 5). When the output measure produced by the drowsiness analysis means 136, 756, 856 exceeds the threshold value determined in step 518, the individual may be considered to be excessively drowsy. For an experimental embodiment of the invention similar to the first preferred embodiment 700 disclosed herein, a threshold factor of 3.0 was found appropriate for advance detection of extreme drowsiness likely to affect performance. Other threshold factors may be appropriate for different applications. For example, a smaller threshold factor could be used to increase sensitivity to detect even mild drowsiness. Larger threshold factors may be appropriate for use in detecting particular sleep stages, or for monitoring aspects of a subject's state of consciousness or response to anesthesia.

FIG. 17 is a simplified block diagram showing the general structure of a third embodiment 400 of an EEG signal processor means 124 for use in an EEG-based drowsiness monitoring system 100 which is constructed according to the present invention and which is adapted for use with analog signal processing and related techniques. Analog signal processing techniques can often be efficiently implemented at very low cost. As best seen in FIG. 17, the third embodiment 400 receives amplified analog EEG signals as input data on lead 130, analyzes the signals, and responsively produces an output measure on lead 138 indicating the subject's state of alertness, drowsiness, or sleep.

The third embodiment 400 provides functions similar, and largely analogous, to those of the first and second embodiments 700, 800, but employs a different configuration of functional components suitable for analog signal processing. Like the first and second embodiments 700, 800, the third embodiment comprises means for selecting particular EEG signal components which have heretofore been discarded or ignored in accord with the teachings of the prior art, and means for exploiting the information contained in these components to provide a reliable measure of a subject's alertness or drowsiness. In general, the third embodiment 400 defines several frequency ranges of interest (denoted a–m) and independently processes the selected frequency ranges in respective analog signal processing channels 408a–408m. The reference numbers referring to the components of each channel are denoted with a suffix letter indicating the channel to which they belong; like reference numbers (excluding the suffix letter) generally denote equivalent components in each channel. A reference lacking a suffix letter made to a component common to all channels is intended to refer to the respective equivalent components in all channels. Any suitable number of frequency ranges and associated separate processing channels 408, may be used (such as the five frequency ranges defined in the first and second embodiments 700, 800). For this discussion, and the diagram of FIG. 17, the choice of subscripts is not meant to imply the presence of a particular number of frequency ranges or processing channels.

In each channel 408a–408m, amplified analog EEG data received on lead 130 is presented to frequency selection means 410. For each channel, the frequency selection means 410 allows signals within the channel's predefined frequency range for that channel to pass, while substantially attenuating signals outside of the channel's frequency range. Frequency selection means 410 may be implemented using any appropriate filter design, of which many suitable ones are well known in the signal processing art. The selection of the frequency range of each channel is preferably done cooperatively with the design of the corresponding frequency selection means. Depending on cost, availability, and other practical aspects of filter design, the frequency ranges to which respective channels are directed may overlap or be mutually exclusive.

The output of frequency selection means 410, which appears as a band-pass filtered version of the original analog EEG input signal, is provided via lead 412 to energy determination means 414. For each channel, energy determination means 414 integrates the instantaneous power of the bandpass-filtered signal over a time interval T preceding the current time t: $\int_{t-T}^{t} \hat{X}^2_{ch}(\tau) d\tau$. Energy determination means 414 may be implemented using any suitable integrator, designs for which are well known in the art.

The output of energy determination means 414 is supplied via lead 416 to energy value inversion means 418. Inversion means 418 determines the inverse of the energy in the band-pass filtered signal (for each channel). As discussed above in connection with bin energy inversion means 236 of FIGS. 14–15, the use of an inversion in producing the drowsiness output measure was selected because it produces an output measure having a particular desired response characteristic. However, the desired output signal response could be achieved using other functions. In some applications, different types of output signals may be desired, eliminating the need for the inversion, or the energy values in the frequency bands of interest could be used directly without additional processing.

The output of the energy value inversion means 418 is provided via lead 420 to weighting function means 422. For each channel, the weighting function means 422 applies a respective predetermined weighting function to the inverted energy value. In a preferred embodiment of the invention, the energy from each channel may be equally weighted using the weighting function $f_{ch}(u) = ku$. In this case, the weighting function is multiplication by the same constant value k. In a preferred embodiment, k may be set to 0.2. However, each bin could be weighted by a different scalar value, and more generalized weighting functions could also be used. The weighting function means may be implemented using a commercially available operational amplifier or a multiplier.

The outputs of the weighting function means 422a–422m for all channels are preferably provided via leads 424a–424m to a single summation means 426, which determines the sum of the weighted inverse energy values over all channels. The summation means 426 may be implemented using a commercially available analog summer or adder, or a network of operational amplifiers. The resulting sum is provided as the drowsiness output measure signal on lead 138.

The above-described embodiments of the invention are merely examples of ways in which the invention may be carried out. Other ways may also be possible, and are within the scope of the following claims defining the invention.

BIBLIOGRAPHY

Akerstedt, T. and M. Gillberg (1990), "Subjective and Objective Sleepiness in the Active Individual," Int. J. of Neuroscience, Vol. 52, pp. 29–37.

Akerstedt, T., G. Kecklund, and A. Knutsson (1991), "Manifest Sleepiness and the Spectral Content of the EEG during Shift Work," Sleep, Vol. 14, No. 3, pp. 221–225.

Carskadon, M. A., A. Rechtschaffen (1987), "Chapter 73: Monitoring and Staging Human Sleep,"—from: Principles and Practice of Sleep Medicine—section 7 methodology, by W. B. Saunders, Philadelphia, Pa.

Chiu U.S. Pat. No. 4,875,030.

Daniel, R. S. (1967), "Alpha and Theta EEG in Vigilance," Percept. Mot. Skills, Vol. 25, pp. 697–703.

Dinges, D. F. (1988), "The Nature of Sleepiness: Causes, Contexts, and Consequences," Perspectives in Behavioral Medicine, A. Baum and A. Stunkard, eds., New Jersey, Erlbaum.

Dingus, T. A., H. L. Hardee, and W. W. Wierwille (1987), "Development of Models for On-Board Detection of Driver Impairment," Accident Analysis and Prevention, Vol. 19, No. 4.

Duff, G. W., unpublished observations (referenced in Mitler et al., 1988).

Estrada U.S. Pat. No. 3,953,831.

Fruhstorfer, H., P. Langanke, K. Meinzer, J. H. Peter, and U. Pfaff (1977), "Neurophysiological Vigilance Indicators and Operational Analysis of a Train Vigilance Monitoring Device: A Laboratory and Field Study," in Vigilance, edited by R. R. Mackie, Plenum Press, New York, pp. 147–162.

Gaillard, J. M. (1987), "EEG Fitting: A New Method for Numerical Analysis of EEG," Neuropsychobiology, Vol. 17, pp. 9–14.

Gale, A. (1977), "Some EEG Correlates of Sustained Attention," in Vigilance, edited by R. R. Mackie, Plenum Press, New York, pp. 263–283.

Horvath, M., E. Frantik, K. Kopriva, and J. Meissner (1976), "EEG Theta Activity Increase Coinciding with Performance Decrement in a Monotonous Task," Activ. Nerv. Sup. (Praha), Vol. 18, pp. 207–210.

Kishi U.S. Pat. No. 5,311,877.

Langlois, P. H., M. H. Smolensky, B. P. Hsi, and F. W. Weir (1985), "Temporal Patterns of Reported Single-Vehicle Car and Truck Accidents in Texas, U.S.A., during 1980–1983," Chronobiology Int., Vol. 2, pp. 131–140.

Lavie, P., M. Wollman, and I. Pollack (1986), "Frequency of Sleep Related Traffic Accidents and Hour of the Day," Sleep Research, Vol. 15, p. 275.

Makeig, S. and M. Inlow (1993), "Lapses in Alertness: Coherence of Fluctuations in Performance and EEG Spectrum," Electroencephalography and Clinical Neurophysiology, 86(1993)23–35.

Mitler, M. M., M. A. Carskadon, C. A. Czeisler, W. C. Dement, D. F. Dinges, and R. C. Graeber (1988), "Catastrophes, Sleep, and Public Policy: Consensus Report," Sleep, Vol. 11, No. 1, pp. 100–109.

Molodofsky, H. (1992), "Evaluation of Daytime Sleepiness," Clinics in Chest Medicine, Vol. 13, No. 3, pp. 417–425.

O'Hanlon, J. F. and J. Beatty (1977), "Concurrence of Electroencephalographic and Performance Changes During a Simulated Radar Watch and Some Implications for the Arousal Theory of Vigilance," in Vigilance, edited by R. R. Mackie, Plenum Press, New York, pp. 189–202.

O'Hanlon, J. F. and G. R. Kelley (1977), "Comparison of Performance and Physiological Changes Between Drivers Who Perform Well and Poorly During Prolonged Vehicular Operation," in Vigilance, edited by R. R. Mackie, Plenum Press, New York, pp. 87–110.

Olsen et al. U.S. Pat. No. 5,311,876.

Planque, S., D. Chaput, C. Petit, and C. Tarriere (1991), "Analysis of EOG and EEG Signals to Detect Lapses of Alertness in Car Simulation Driving,"Presented at the 13th ESV Conference, Paris France, November 4–7, 1991 (referenced in Wierwille (1994)).

Pritchard, W. S. (1995), "Measuring 'Chaos' in the Brain: A Tutorial Review of EEG Dimension Estimation," Brain and Cognition, Vol. 27, pp. 353–397.

Santamaria, J. and K. H. Chiappa (1987), "The EEG of Drowsiness in Normal Adults," J. of Clinical Neurophysiology, Vol. 4, pp. 327–382.

Seko et al. U.S. Pat. No. 4,564,833.

Seko et al. U.S. Pat. No. 4,604,611.

Slansky U.S. Pat. No. 4,617,559.

Smith, J. R. (1987), "Computer Analysis of Sleep Data," in Clinical Applications of Computer Analysis of EEG and other Neurophysiological Signals, Handbook of EEG and Clinical Neurophysiology (revised series, Vol. 2), F. H. Lopes da Silva, W. Storm van Leeuwen, and A. Remond, Eds., Amsterdam: Elsevier, pp. 131–145.

Stanford Sleep Disorders Clinic and Research Center (1991), "Why Should We Care About Sleep? The Toll of Daytime Sleepiness and Sleep Disorders on Society."

Torsvall, L. and T. Akerstedt (1987), "Sleepiness on the Job: Continuously Measured EEG Changes in Train Drivers," Electroen. and Clinical Neurophy., Vol. 66, pp. 502–511.

Torsvall, L., T. Akerstedt, K. Gillander, and A. Knutsson (1989), "Sleep on the Night Shift: 24-Hour EEG Monitoring of Spontaneous Sleep/Wake Behavior," Psychophysiology, Vol. 26, No. 3, pp. 353–358.

Trejo, L. J., and M. J. Shensa (1993), "Linear and Neural Network Models for Predicting Human Signal Detection Performance from Event-Related Potentials: A Comparison of the Wavelet Transform with Other Feature Extraction Methods," Navy Personnel Research and Development Center (San Diego, Calif.), and Naval Command Control and Ocean Surveillance Center, RDT&E Division (San Diego, Calif.).

U.S. Department of Health and Human Services (1992), Wake Up America: A National Sleep Alert, Vol. 1: Executive Summary and Executive Report, Report of the National Commission on Sleep Disorders Research.

Wierwille, W. W., S. S. Wregitt, and M. W. Mitchell (1992), "Research on Vehicle-Based Driver Status/Performance Monitoring,", First Semiannual Research Report, DTNH22-91-Y-07266.

Wierwille, W. W., S. S. Wreggit, C. L. Kirn, L. A. Ellsworth, R. J. Fairbanks (1994), "Research on Vehicle-Based Driver Status/Performance Monitoring: Development, Validation, and Refinement of Algorithms for Detection of Driver Drowsiness," Final Report, Report # DOT HS 808 247.

Wilkinson, R. T. and D. Houghton (1975), "Portable Four-Choice Reaction Time Test with Magnetic Memory," Behav. Res. Meth. Instru. Comp., Vol. 7, p. 441.

Yoshimi et al. U.S. Pat. No. 4,928,090.

What is claimed is:

1. A system adapted to measure in a human subject a state along a continuum relating to alertness, drowsiness, sleep, unconsciousness, or anesthesia comprising:

means for acquiring a brain-wave signal having rhythmic components from the subject;

means for selecting components of said brain-wave signal lying in a predetermined range of frequencies including frequencies above 30 Hz;

means responsive to said selecting means for determining a contribution to said brain-wave signal due to said components lying in said range; and means responsive to said contribution-determining means for producing an output-measure signal indicative of said state of the subject.

2. A system adapted to measure in a human subject a state along a continuum relating to alertness, drowsiness, sleep, unconsciousness, or anesthesia comprising:

means for acquiring a brain-wave signal having rhythmic components from the subject;

means for defining a range of frequencies including frequencies above 30 Hz;

means for analyzing frequency content of said acquired brain-wave signal responsive to said defined range of frequencies for defining a plurality of frequencies or frequency bands within said range, and for determining for each of said defined frequencies or frequency bands a contribution due to a component of said acquired brain-wave signal at such frequency or within such frequency band; and output-measure-determining means responsive to said frequency analysis means for producing an output signal indicative of said state of the subject.

3. A system adapted to measure in a human subject a state along a continuum relating to alertness, drowsiness, sleep, unconsciousness, or anesthesia comprising:

means for acquiring a brain-wave signal having rhythmic components from the subject;

means for defining a range of frequencies including frequencies above 30 Hz;

means for analyzing frequency content of said acquired brain-wave signal responsive to said defined range of frequencies for defining a plurality of frequencies or frequency bands within said range, and for determining for each of said defined frequencies or frequency bands an amplitude or distribution of amplitudes corresponding to a component or components of said acquired brain-wave signal at such frequency or within such frequency band;

power determination means for determining for each of said defined frequencies the power contained in said corresponding component or for each of said defined frequency bands the distribution of power contained in said corresponding components; and spectral-grouping means for defining a limited number of spectral groups, each of said spectral groups defining a subrange of said range and including at least one of said defined frequencies or frequency bands;

group-energy-determining means responsive to said power determination means and said spectral-grouping means for determining for each of said spectral groups an aggregate energy represented in a plurality of said components corresponding to the defined frequencies or frequency bands included in such group; and output-measure-determining means responsive to said group-energy-determining means for producing an output signal indicative of said state of the subject.

4. A system adapted to measure in a human subject a state along a continuum relating to alertness, drowsiness, sleep, unconsciousness, or anesthesia comprising:

means for acquiring a brain-wave signal having rhythmic components from the subject;

anti-aliasing filter means for substantially removing from said brain-wave signal components outside a first predefined frequency range;

means responsive to said brain-wave signal-acquiring means for converting said brain-wave signal into a sequential plurality of digital data elements representing amplitude of said brain-wave signal at a corresponding plurality of discrete times;

means for selecting for analysis a limited number of said data elements;

means for defining a second range of frequencies including frequencies above 30 Hz;

means for analyzing frequency content of said acquired brain-wave signal, said means being operative to define a plurality of frequencies or frequency bands within said second range, and said means also being responsive thereto and to said selected data elements to determine for each such defined frequency or frequency bands an amplitude or distribution of amplitudes of a component or components of said acquired brain-wave signal at that frequency or within that frequency band;

power determination means for determining for each of said defined frequencies the power contained in said corresponding component or for each of said defined frequency bands the distribution of power contained in said corresponding components;

spectral-grouping means for defining a limited number of spectral groups, each of said spectral groups defining a subrange of said second range and including at least one of said defined frequencies or frequency bands;

group-energy-determining means responsive to said power determination means for determining for each of said spectral groups an aggregate energy represented in a plurality of said components corresponding to the defined frequencies or frequency bands included in such group; and output-measure-determining means responsive to said group-energy-determining means for producing an output signal indicative of said state of the subject.

5. The system of claim 4 wherein said power-determining means further comprises:

noise-removal means for identifying frequencies or frequency bands at which noise is expected, and for substituting for the power value or power distribution at each such identified frequency or frequency band a power value or power distribution corresponding to a neighboring frequency or frequency band.

6. The system of claim 4, further comprising means for causing said output-measure determination to occur at repeated predefined intervals, and wherein said output-measure-determining means further comprises interpolation means for continuously presenting an output signal representing a current value of said output measure until a next-determined value of said output measure becomes available.

7. A system adapted to measure in a human subject a state along a continuum relating to alertness, drowsiness, sleep, unconsciousness, or anesthesia comprising:

means for obtaining a brain-wave signal from the subject;

subject state analysis means responsive to said brain-wave signal obtained from the subject for:

(a) selecting components of said brain-wave signal lying in a first predetermined range of frequencies including frequencies above 30 Hz;

(b) determining a contribution to said brain-wave signal due to said components lying in said range; and (c) producing, responsive to at least said determined contribution, an output-measure signal indicative of said state of the subject.

8. The system of claim 7 further comprising threshold means responsive to said output-measure signal for producing a non-continuous-valued output signal indicating that the subject is drowsy.

9. The system of claim 8 wherein said threshold means comprises:

means for determining a threshold value relating to said output-measure signal whereby said threshold value defines a range of output-measure-signal values corresponding to a defined physiological state of the subject; and means for comparing said output-measure signal with said threshold value to produce a non-continuous-valued output signal indicating that the subject is in said defined physiological state.

10. The system of claim 9 wherein said threshold-value-determining means employs a preselected threshold value believed to be generally applicable to human subjects.

11. The system of claim 10 wherein said threshold-value-determining means employs a threshold determined for the subject responsive to a brain-wave signal obtained from the subject while in a known state along said continuum.

12. The system of claim 8 wherein said threshold means comprises:
   means for determining a threshold value relating to said output-measure signal whereby said threshold value defines a range of output-measure-signal values indicating that the subject is drowsy; and
   means for comparing said output-measure signal with said threshold value to produce a non-continuous-valued output signal indicating that the subject is drowsy.

13. The system of claim 7 further comprising threshold means responsive to said output-measure signal for producing a non-continuous-valued output signal indicating said state of the subject.

14. The system of claim 7 further comprising artifact detection means for determining whether said brain-wave signal obtained from the subject is apparently contaminated by artifact.

15. The system of claim 14 further comprising means responsive to said artifact detection means for eliminating from said output signal an effect of said brain-wave signal obtained when artifact is determined to be present.

16. The system of claim 14 wherein said artifact detection means is responsive to said brain-wave signal acquired from the subject to determine whether said brain-wave signal obtained from the subject is apparently contaminated by artifact.

17. The system of claim 14 wherein said artifact detection means is responsive to information other than said brain-wave signal obtained from the subject to determine whether said brain-wave signal obtained from the subject is apparently contaminated by artifact.

18. The system of claim 7 further comprising means responsive to an output signal of said system to produce a warning indicating that the subject is not fully alert.

19. The system of claim 18 wherein said warning is an audible alarm.

20. The system of claim 18 wherein said warning is a visual display.

21. The system of claim 7 wherein said subject state analysis means comprises:
   at least one brain-wave signal-processing channel,
   each such brain-wave signal-processing channel being directed to a corresponding range of frequencies and supplying an output representing a contribution to said brain-wave signal obtained from said subject due to components thereof lying substantially within said corresponding range of frequencies; and
   means responsive to said outputs supplied by a plurality of such brain-wave signal-processing channels to produce said output-measure signal indicative of said state of the subject.

22. The system of claim 21 wherein each brain-wave signal-processing channel comprises:
   frequency selection means responsive to said obtained brain-wave signal for passing substantially exclusively brain-wave signal components within said corresponding range of frequencies; and
   energy-determination means responsive to an output of said frequency selection means for determining energy contained in said brain-wave signal components within said corresponding range of frequencies during a predefined time interval.

23. The system of claim 22 wherein each brain-wave signal processing channel further comprises:
   means responsive to an output of said energy-determination means for determining an inverse of said energy contained in said brain-wave signal components within said corresponding range of frequencies.

24. The system of claim 23 wherein each brain-wave signal processing channel further comprises:
   weighting-function means responsive to an output of said inverse-energy-determining means for applying a predetermined weight to said inverse of said energy.

25. The system of claim 24 wherein said means responsive to said outputs supplied by a plurality of such brain-wave signal-processing channels to produce said output-measure signal comprises a summation means responsive to an output from said weighting function means of each brain-wave signal-processing channel.

26. The system of claim 7 further comprising brain-wave signal acquisition means, said brain-wave signal acquisition means including:
   filter means for receiving a representation of said brain-wave signal obtained from the subject, and for substantially attenuating signal components above a predefined cutoff frequency and substantially preserving signals in said range above 30 Hz; and
   conversion means responsive to said brain-wave signal obtained from the subject for producing a digital representation of said brain-wave signal.

27. The system of claim 26 wherein said subject state analysis means comprises:
   means for analyzing frequency content of said acquired brain-wave signal responsive to said digital representation of said brain-wave signal and said first predefined range of frequencies for defining a plurality of frequencies or frequency bands within said range, and for determining for each of said defined frequencies or frequency bands an amplitude or distribution of amplitudes corresponding to a component or components of said brain-wave signal at such frequency or within such frequency band;
   power determination means for determining for each of said defined frequencies a power represented in said corresponding components or for each of said defined frequency bands a power distribution represented in said corresponding components; and
   spectral-grouping means for defining a limited number of spectral groups, each of said spectral groups defining a group of frequencies within said first predefined range of frequencies and including at least one of said defined frequencies or frequency bands;
   group-energy-determining means responsive to said power determination means and said spectral-grouping means for determining for each of said spectral groups an aggregate energy represented in a plurality of said components corresponding to the defined frequencies or frequency bands included in such spectral group; and
   output-measure-determining means responsive to said group-energydetermining means for producing said output-measure signal indicative of said state of the subject.

28. The system of claim 27 wherein said brain-wave signal acquisition means includes a first digital control and processing means and said subject state analysis means includes a second digital control and processing means.

29. The system of claim 27 wherein said system includes a digital control and processing means operatively connected to said brain-wave signal acquisition means and to said subject state analysis means, whereby said digital control and processing means performs at least some processing functions for each of said brain-wave signal acquisition means and said subject state analysis means.

30. The system of claim 7 further comprising brain-wave signal acquisition means, said brain-wave signal acquisition means including:

filter means for receiving a representation of said brain-wave signal obtained from the subject, and for substantially attenuating signal components outside a second predefined frequency range and substantially preserving signals in said range above 30 Hz; and conversion means responsive to said brain-wave signal obtained from said subject for converting said brain-wave signal into a sequential plurality of digital data elements representing amplitude of said brain-wave signal at a corresponding plurality of discrete times.

31. The system of claim 30 wherein said subject state analysis means further comprises:

means for selecting for analysis a limited number of said data elements;

means for analyzing frequency content of said acquired brain-wave signal, said means being operative to define a plurality of frequencies or frequency bands within said first predefined range, said means also being responsive thereto and to said selected data elements to determine for each such defined frequency or frequency band an amplitude or distribution of amplitudes corresponding to a component or components of said acquired brain-wave signal at that frequency or within that frequency band;

power determination means for determining for each of said defined frequencies a power represented in said corresponding component or for each of said defined frequency bands a distribution of power represented in said corresponding components;

spectral-grouping means for defining a limited number of spectral groups, each of said spectral groups defining a group of frequencies within said first predefined range and including at least one of said defined frequencies or frequency bands;

group-energy-determining means responsive to said power determination means and said spectral-grouping means for determining for each of said spectral groups an aggregate energy represented in a plurality of said components corresponding to the defined frequencies or frequency bands included in such spectral group; and output-measure-determining means responsive to said group-energydetermining means for producing an output signal indicative of said state of the subject.

32. A system adapted to measure in a human subject a state along a continuum relating to alertness, drowsiness, sleep, unconsciousness, or anesthesia comprising:

means for obtaining a brain-wave signal having rhythmic components from the subject over at least a first predetermined range of frequencies including a second predefined range of frequencies including frequencies above 30 Hz;

brain-wave signal acquisition means including: (a) filter means for receiving a representation of said brain-wave signal obtained from said subject, and for substantially attenuating signal components outside a third predefined frequency range and substantially preserving signals within said second predefined subrange; and (b) conversion means responsive to a representation of said brain-wave signal obtained from the subject for producing a digital representation of said brain-wave signal; and subject state analysis means responsive to said digital representation of said brain-wave signal for:
(a) selecting components of said brain-wave signal lying in said first predetermined range of frequencies including said second predefined range;
(b) determining a contribution to said brain-wave signal due to said components lying in said second predefined range; and
(c) producing, responsive to at least said determined contribution, an output-measure signal indicative of said state of the subject.

33. The system of claim 32 wherein said subject state analysis means comprises:

means for analyzing frequency content of said acquired brain-wave signal responsive to said first predefined range of frequencies for defining a plurality of frequencies or frequency bands within said range, and for determining for each of said defined frequencies or frequency bands an amplitude or distribution of amplitudes corresponding to said component or components of said acquired brain-wave signal at such frequency or within such frequency band;

power determination means for determining for each of said defined frequencies a power represented in said corresponding components or for each of said defined frequency bands a distribution of power represented in said corresponding components; and spectral-grouping means for defining a limited number of spectral groups, each of said spectral groups defining a group of frequencies within said first predefined range and including at least one of said defined frequencies or frequency bands;

group-energy-determining means responsive to said power determination means and said spectral-grouping means for determining for each of said spectral groups an aggregate energy represented in a plurality of said components corresponding to the frequencies or frequency bands included in such spectral group; and output-measure-determining means responsive to said group-energy-determining means for producing said output-measure signal indicative of said state of the subject.

34. The system of claim 33 wherein said brain-wave signal acquisition means includes a first digital control and processing means and said subject state analysis means includes a second digital control and processing means.

35. The system of claim 33 wherein said system includes a digital control and processing means operatively connected to said brain-wave signal acquisition means and to said subject state analysis means, whereby said digital control and processing means performs at least some processing functions for each of said brain-wave signal acquisition means and said subject state analysis means.

36. The system of claim 32 wherein said conversion means converts said brain-wave signal into a sequential plurality of digital data elements representing amplitude of said brain-wave signal at a corresponding plurality of discrete times.

37. The system of claim 36 wherein said subject state analysis means further comprises:
- means for selecting for analysis a limited number of said data elements;
- means for analyzing frequency content of said acquired brain-wave signal, said means being operative to define a plurality of frequencies or frequency bands within said first predefined range, and said means also being responsive thereto and to said selected data elements to determine for each such defined frequency or frequency band an amplitude or distribution of amplitudes corresponding to a component or components of said acquired brain-wave signal at such frequency or within such frequency band;
- power determination means for determining for each of said frequencies the power represented in said corresponding component or for each of said frequency bands the distribution of power represented in said corresponding components;
- spectral-grouping means for defining a limited number of spectral groups, each of said spectral groups defining a group of frequencies within said first predefined range and including at least one of said frequencies or frequency bands;
- group-energy-determining means responsive to said power determination means and said spectral-grouping means for determining for each of said spectral groups an aggregate energy represented in a plurality of said components corresponding to the frequencies or frequency bands included in such spectral group; and
- output-measure-determining means responsive to said group-energy-determining means for producing an output signal indicative of said state of the subject.

38. For use with a system adapted to measure in a human subject a state along a continuum relating to alertness, drowsiness, sleep, unconsciousness, or anesthesia, said system having means for obtaining a brain-wave signal including rhythmic components from the subject, and conversion means responsive to said brain-wave signal for converting the subject's brain-wave signal into a sequential plurality of digital data elements representing amplitude of said brain-wave signal at a corresponding plurality of discrete time intervals, and producing therefrom an output-measure signal indicating said state of the subject; the method of determining a threshold value which defines a range of output-measure signal values indicating that the subject is not fully alert, comprising the steps of:
- (a) obtaining a sequential plurality of digital data elements representing amplitude of said brain-wave signal of the subject over a period of time, said signal including rhythmic components;
- (b) selecting a threshold-determination segment of said digital data elements obtained in step (a) corresponding to a period during which the subject is in a state of wakefulness;
- (c) determining a value of said output-measure signal at each of said plurality of discrete time intervals represented in said threshold-determination segment;
- (d) determining, for each of said plurality of discrete time intervals represented in said threshold-determination segment, whether said output-measure signal is contaminated by artifact during said discrete time interval;
- (e) discarding from said output-measure-signal values substantially all output-measure-signal values corresponding to said discrete time intervals during which said output-measure-signal value is contaminated by artifact;
- (f) determining a known-state baseline output-measure value for the subject as a combined value of substantially all undiscarded output-measure-signal values corresponding to said discrete time intervals represented in said threshold-determination segment; and
- (g) multiplying said known-state baseline output-measure value for the subject by a predetermined threshold factor to obtain a drowsiness-output-measure threshold value for the subject.

39. For use with a system adapted to measure in a human subject a state along a continuum relating to alertness, drowsiness, sleep, unconsciousness, or anesthesia, said system having means for obtaining a brain-wave signal including rhythmic components from the subject, and conversion means responsive to said brain-wave signal for converting said brain-wave signal into a sequential plurality of digital data elements representing amplitude of said brain-wave signal at a corresponding plurality of discrete time intervals, and producing therefrom an output-measure signal indicating said state of the subject; the method of determining a threshold value which defines a range of output-measure-signal values corresponding to a selected physiological state of the subject, comprising the steps of:
- (a) obtaining a sequential plurality of digital data elements representing amplitude of said brain-wave signal of the subject over a period of time, said signal including rhythmic components;
- (b) selecting a threshold-determination segment of said digital data elements obtained in step (a) corresponding to a period during which the subject is in a known state along said continuum;
- (c) determining a value of said output-measure signal at each of said plurality of discrete time intervals represented in said threshold-determination segment;
- (d) determining, for each of said plurality of discrete time intervals represented in said threshold-determination segment, whether said output-measure signal is contaminated by artifact during said discrete time interval;
- (e) discarding from said output-measure-signal values substantially all output-measure-signal values corresponding to said discrete time intervals during which said output-measure-signal value is contaminated by artifact;
- (f) determining a known-state baseline output-measure value for the subject as a combined value of substantially all undiscarded output-measure-signal values corresponding to said discrete time intervals represented in said threshold-determination segment;
- (g) multiplying said known-state baseline output-measure value for the subject by a predetermined threshold factor to obtain an output-measure threshold value for the subject corresponding to said selected physiological state.

40. For use in analyzing brain-wave signal information acquired from a human subject, said brain-wave signal information being presented as a sequential plurality of digital data elements representing amplitude of the subject's brain-wave signal at a corresponding plurality of discrete time intervals, and producing therefrom an output-measure signal indicating the subject's state along a continuum relating to alertness, drowsiness, sleep, unconsciousness, or anesthesia; the method of determining a threshold value which defines a range of output-measure-signal values indicating that the subject is not fully alert, comprising the steps of:
- (a) obtaining a sequential plurality of digital data elements representing amplitude of a brain-wave signal of the subject over a period of time, said signal including rhythmic components;

(b) selecting a threshold-determination segment of said digital data elements obtained in step (a) corresponding to a period during which the subject is in a state of wakefulness;

(c) determining a value of said output-measure signal at each of said plurality of discrete time intervals represented in said threshold-determination segment;

(d) determining, for each of said plurality of discrete time intervals represented in said threshold-determination segment, whether said output-measure signal is contaminated by artifact during said discrete time interval;

(e) discarding from said output-measure-signal values substantially all output-measure-signal values corresponding to said discrete time intervals during which said output-measure-signal value is contaminated by artifact;

(f) determining a known-state baseline output-measure value for the subject as a combined value of substantially all undiscarded output-measure-signal values corresponding to said discrete time intervals represented in said threshold-determination segment; and (g) multiplying said known-state baseline output-measure value for the subject by a predetermined threshold factor to obtain a drowsiness output-measure threshold value for the subject.

41. For use in analyzing brain-wave signal information acquired from a human subject, said brain-wave signal information being presented as a sequential plurality of digital data elements representing amplitude of the subject's brain-wave signal at a corresponding plurality of discrete time intervals, and producing therefrom an output-measure signal indicating the subject's state along a continuum relating to alertness, drowsiness, sleep, unconsciousness, or anesthesia; the method of determining a threshold value which defines a range of output-measure-signal values corresponding to a selected physiological state of the subject, comprising the steps of:

(a) obtaining a sequential plurality of digital data elements representing amplitude of a brain-wave signal of the subject over a period of time, said signal including rhythmic components;

(b) selecting a threshold-determination segment of said digital data elements obtained in step (a) corresponding to a period during which the subject is in a known state along said continuum;

(c) determining a value of said output-measure signal at each of said plurality of discrete time intervals represented in said threshold-determination segment;

(d) determining, for each of said plurality of discrete time intervals represented in said threshold-determination segment, whether said output-measure signal is contaminated by artifact during said discrete time interval;

(e) discarding from said output-measure-signal values substantially all output-measure-signal values corresponding to said discrete time intervals during which said output-measure-signal value is contaminated by artifact;

(f) determining a known-state baseline output-measure value for the subject as a combined value of substantially all undiscarded output-measure-signal values corresponding to said discrete time intervals represented in said threshold-determination segment;

(g) multiplying said known-state baseline output-measure value for the subject by a predetermined threshold factor to obtain an output-measure threshold value for the subject corresponding to said selected physiological state.

42. For use with a system adapted to measure in a human subject a state along a continuum relating to alertness, drowsiness, sleep, unconsciousness, or anesthesia, said system having means for obtaining a brain-wave signal including rhythmic components from the subject, and conversion means responsive to said brain-wave signal for converting said brain-wave signal into a sequential plurality of digital data elements representing amplitude of said brain-wave signal at a corresponding plurality of discrete time intervals, and producing therefrom an output-measure signal indicating said state of the subject; the method of detecting whether said brain-wave signal is contaminated by artifact during a selected time period, comprising the steps of:

(a) obtaining an artifact determination segment of data comprising a sequential plurality of digital data elements representing amplitude of selected rhythmic components of said brain-wave signal of the subject over a period of time, said signal including rhythmic components;

(b) selecting in turn for further processing a plurality of data windows, each comprising a subset of said artifact determination segment corresponding to an adjacent predefined window interval within said period of time;

(c) rejecting as saturated and in its entirety any data window containing a digital data element having at least one value equal to the maximum value which may be produced by said conversion means;

(d) analyzing frequency content of said brain-wave signal using said data elements of said data window, thereby determining for each of a plurality of defined frequencies or frequency bands an amplitude or distribution of amplitudes corresponding to a component or components of said brain-wave signal at such defined frequency or within such frequency band;

(e) determining for each of said defined frequencies power represented in said corresponding components or for each of said defined frequency bands a distribution of power represented in said corresponding components;

(f) defining at least one spectral group, each of said spectral groups comprising a group of frequencies which may be present in said brain-wave signal and including at least one of said defined frequencies or frequency bands;

(g) determining for each of said spectral groups an aggregate energy represented in a plurality of said components corresponding to the frequencies included in such group;

(h) determining a combined value of said aggregate energy present in a plurality of said spectral groups over a plurality of said data windows in said artifact determination segment;

(i) multiplying said combined value of said aggregate energy by a predetermined artifact threshold factor to produce an artifact threshold value; and (j) comparing said aggregate energy for each data window to said artifact threshold value, and identifying as contaminated by artifact each window interval in which the corresponding aggregate energy exceeds said artifact threshold value.

43. The method of claim 42 further comprising the step of:

(k) inhibiting use of said output-measure signal corresponding to each window interval identified as contaminated by artifact in step (j).

44. The method of claim 42 further comprising the step of:

(k) further identifying as contaminated by artifact each window interval in which said corresponding data window was rejected in step (c).

45. The method of claim 42 further comprising the steps of:

(k) receiving at least one additional signal, other than said brain-wave signal, providing information concerning whether said brain-wave signal is contaminated by artifact; and (l) further identifying as contaminated by artifact each window interval in which said additional signal indicates said brain-wave signal is contaminated by artifact.

46. For use in analyzing brain-wave signal information acquired from a human subject, said brain-wave signal information being presented as a sequential plurality of digital data elements representing amplitude of the subject's brain-wave signal at a corresponding plurality of discrete time intervals, said digital data elements being derived from said brain-wave signal through a conversion process, and producing therefrom an output-measure signal indicating the subject's state along a continuum relating to alertness, drowsiness, sleep, unconsciousness, or anesthesia; the method of detecting whether said brain-wave signal data corresponding to a selected time period is contaminated by artifact, comprising the steps of:

(a) obtaining an artifact determination segment of data comprising a sequential plurality of digital data elements representing amplitude of said brain-wave signal of the subject over a period of time, said signal including rhythmic components;

(b) selecting in turn for further processing a plurality of data windows, each comprising a subset of said artifact determination segment corresponding to an adjacent predefined window interval within said period of time;

(c) rejecting as saturated and in its entirety any data window containing a digital data element having at least one value equal to a maximum value which may be produced in said conversion process;

(d) analyzing frequency content of said brain-wave signal using said data elements of said data window, thereby determining for each of a plurality of defined frequencies or frequency bands an amplitude or distribution of amplitudes corresponding to a component or components of said brain-wave signal at such defined frequency or within such frequency band;

(e) determining for each of said defined frequencies power represented in said corresponding components or for each of said defined frequency bands a distribution of power represented in said corresponding components;

(f) defining at least one spectral group, each of said spectral groups comprising a group of frequencies which may be present in said brain-wave signal and including at least one of said defined frequencies or frequency bands;

(g) determining for each of said spectral groups an aggregate energy represented in a plurality of said components corresponding to the frequencies included in such group;

(h) determining a combined value of said aggregate energy present in a plurality of said spectral groups over a plurality of said data windows in said artifact determination segment;

(i) multiplying said combined value of said aggregate energy by a predetermined artifact threshold factor to produce an artifact threshold value; and (j) comparing said aggregate energy for each data window to said artifact threshold value, and identifying as contaminated by artifact each window interval in which the corresponding aggregate energy exceeds said artifact threshold value.

47. For use with a system adapted to measure in a human subject a state along a continuum relating to alertness, drowsiness, sleep, unconsciousness, or anesthesia, said system having means for obtaining a brain-wave signal including rhythmic components from the subject, and conversion means responsive to said brain-wave signal for converting said brain-wave signal into a sequential plurality of digital data elements representing amplitude of said brain-wave signal at a corresponding plurality of discrete time intervals, and producing therefrom an output-measure signal indicating said state of the subject; the method of producing said output-measure signal, comprising the steps of:

(a) obtaining selected rhythmic components of said brain-wave signal from the subject, said signal including rhythmic components;

(b) defining at least one range of frequencies including frequencies above 30 Hz;

(c) for each such defined range, determining a contribution to said brain-wave signal due to components of said signal at frequencies lying within that defined range; and (d) determining said output-measure signal responsive to said contributions to said brain-wave signal determined for a plurality of said defined ranges in combination.

48. The method of claim 47 wherein step (b) further comprises the step of defining at least one range including frequencies above 30 Hz.

49. The method of claim 47 wherein step (a) further comprises the steps of:

(a1) acquiring said brain-wave signal as an electrical signal;

(a2) amplifying said electrical signal;

(a3) filtering said electrical signal such that signal components outside a second predefined frequency range are substantially attenuated and signals in each of said defined ranges are substantially preserved.

50. The method of claim 47 wherein step (a) further comprises the steps of:

(a1) acquiring said brain-wave signal as an electrical signal;

(a2) converting said electrical brain-wave signal into a sequential plurality of digital data elements representing amplitude of said brain-wave signal at a corresponding plurality of discrete times.

51. The method of claim 47 wherein step (c) further comprises the steps of:

(c1) defining a plurality of data windows, each comprising a subset of said digital data elements corresponding to a predefined window interval;

(c2) selecting each of said windows in turn for further processing;

(c2) applying a windowing function to adjust values of said digital data elements of said selected window;

(c3) analyzing frequency content of said brain-wave signal using said digital data elements of said selected window, thereby determining for each of a plurality of defined frequencies or frequency bands an amplitude or amplitude distribution corresponding to a component or components of said brain-wave signal at such frequency or within such frequency band;

(c4) for each of said plurality of said defined frequencies or frequency bands determining the power or distribution of power contributed by said corresponding component or components of said brain-wave signal;

(c5) defining at least one spectral bin and assigning to each of said defined spectral bins at least one of said defined frequencies or frequency bands;

(c6) for each of said spectral bins, determining a total energy contributed by said components of said EEG signal corresponding to a plurality of said defined frequencies or frequency bands assigned to such spectral bin.

52. The method of claim 51 wherein step (c4) further comprises the steps of:

(c4i) defining at least one of said defined frequencies or frequency bands as an undesired frequency or frequency band; and (c4ii) for each of said undesired frequencies or frequency bands, whenever further processing would require use of said determined contribution due to a component or components corresponding to such frequency or frequency band, substituting therefor a value derived from said determined contribution due to a component or components corresponding to at least one nearby frequency or frequency band.

53. The method of claim 51 wherein:

step (a) further comprises the step of (a1) applying an anti-aliasing filter to said brain-wave signal obtained from said subject; and step (c4) further comprises the step of (c4i) adjusting said determined contribution to compensate for an effect of said filtering step in at least one of said subranges.

54. The method of claim 47 wherein step (d) further comprises the steps of:

(d1) for each such defined range, determining an inverse of energy contained in said brain-wave signal by signal components corresponding to frequencies within that defined range; and (d2) for each such defined range, applying a respective predefined weight to said corresponding inverse-energy value; and (d3) determining a value for said output-measure signal by arithmetically combining said weighted inverse-energy values of a plurality of said defined ranges.

55. For use in analyzing brain-wave signal information acquired from a human subject, said brain-wave signal information being presented as a sequential plurality of digital data elements representing amplitude of said subject's brain-wave signal at a corresponding plurality of discrete time intervals, said signal including rhythmic components, said digital data elements being derived from said brain-wave signal through a conversion process, and producing therefrom an output-measure signal indicating the subject's state along a continuum relating to alertness, drowsiness, sleep, unconsciousness, or anesthesia; the method of producing said output-measure signal, comprising the steps of:

(a) analyzing frequency content of said brain-wave signal including rhythmic components using said digital data elements, thereby determining for each of a plurality of defined frequencies or frequency bands an amplitude or amplitude distribution corresponding to a component or components of said brain-wave signal at such frequency or within such frequency band;

(b) defining at least one range of frequencies including frequencies above 30 Hz;

(c) for each such defined range, determining a contribution to said brain-wave signal due to components of said signal at frequencies lying within that defined range; and (d) determining said output-measure signal responsive to said contributions to said brain-wave signal determined for a plurality of said defined ranges in combination.

56. The method of claim 55 wherein step (b) further comprises the step of defining at least one range including frequencies above 30 Hz.

57. A system adapted to measure in a human subject a state along a continuum relating to alertness, drowsiness, sleep, unconsciousness, or anesthesia comprising:

means for acquiring an electrical brain-wave signal including rhythmic components from the subject;

at least one signal-processing channel means;

each such signal-processing channel means being associated with a respective predefined range of frequencies;

at least one of said signal-processing channel means being associated with a range of frequencies including frequencies above 30 Hz;

each such signal-processing channel means having: means for receiving said acquired brain-wave signal; means for substantially limiting response of said signal-processing channel to its associated predefined range of frequencies; and means for determining a contribution to said brain-wave signal due to components thereof lying within said associated predefined range of frequencies;

and means for receiving from a plurality of such signal-processing channel means respective signals representing said determined contributions and for responsively determining an output-measure signal indicative of said state of the subject.

58. The system of claim 57 wherein said means for substantially limiting response of said signal-processing channel comprises a band-pass filter.

59. The system of claim 57 wherein each such signal-processing channel means further comprises:

means for determining power contributed to said brain-wave signal due to components lying within said associated predefined range of frequencies.

60. The system of claim 59 wherein each such signal-processing channel means further comprises:

means responsive to said power-determining means for determining energy contributed to said brain-wave signal over a predefined time interval due to components lying within said associated predefined range of frequencies.

means responsive to said energy-determining means for determining an inverse value of said energy contribution; and weighting means responsive to said inverse-value-determining means for applying a weighting function to said determined inverse value.

61. The system of claim 60 wherein said energy-determining means comprises an integrator.

62. The system of claim 60 wherein said weighting means comprises means for establishing a weighting parameter, means for receiving a signal representing said inverse-energy value, and multiplier means for multiplying said signal by said inverse-energy value.

63. The system of claim 57 wherein each such signal-processing channel means further comprises:

means for determining energy contributed to said brain-wave signal over a predefined time interval due to components lying within said associated predefined range of frequencies.

64. The system of claim 57 wherein said output-measure-determining means comprises a summer.

65. A system adapted to measure in a human subject a state along a continuum relating to alertness, drowsiness, sleep, unconsciousness, or anesthesia comprising:

means for acquiring a brain-wave signal including rhythmic components from the subject;

means for selecting components of said brain-wave signal lying in a predetermined range of frequencies including frequencies above 30 Hz; and means responsive to components of said signal corresponding to frequencies lying in said range for producing an output-measure signal indicative of said state of the subject;

said means for producing said output-measure signal being adapted to modify its response when artifact is present in said brain-wave signal.

66. The system of claim 65 wherein:

said means for producing said output-measure signal causes said output-measure signal to change in a first direction when said state of the subject approaches alertness; and said means for producing said output-measure signal causes said output-measure signal to change in said first direction responsive to presence of artifact in said brain-wave signal.

67. The system of claim 65 wherein:

said means for producing said output-measure signal causes said output-measure signal to change in a first direction when said state of the subject deviates from alertness; and said means for producing said output-measure signal to change in a direction opposite from said first direction responsive to presence of artifact in said brain-wave signal.

* * * * *